US008404436B1

(12) United States Patent
Kostenis et al.

(10) Patent No.: US 8,404,436 B1
(45) Date of Patent: Mar. 26, 2013

(54) METHODS OF IDENTIFYING MODULATORS OF GPR17

(75) Inventors: Evi Kostenis, Bonn (DE); Andreas Spinrath, Munich (DE); Stephanie Hennen, Saarburg (DE); Lucas Peters, Bad Honnef (DE); Christa E. Muller, Bonn (DE); Rhalid Akkari, Pantin (FR); Younis Baqi, Bonn (DE); Kirsten Ritter, Jena (DE)

(73) Assignee: Rheinische Friedrich-Wilhelms-Universitat Bonn, Bonn (DE)

(*) Notice: Subject to any disclaimer, the term of this patent is extended or adjusted under 35 U.S.C. 154(b) by 0 days.

(21) Appl. No.: 13/407,512

(22) Filed: Feb. 28, 2012

(30) Foreign Application Priority Data

Jul. 9, 2011 (EP) .................................. 11180467

(51) Int. Cl.
*C12Q 1/00* (2006.01)
*G01N 33/53* (2006.01)
*C07D 209/04* (2006.01)
(52) U.S. Cl. .............................. 435/4; 435/7.1; 548/469
(58) Field of Classification Search ............... 435/4, 7.1; 548/469
See application file for complete search history.

(56) References Cited

U.S. PATENT DOCUMENTS 4,960,786 A  10/1990  Salituro et al.
7,833,722 B2  11/2010  Fujii et al.

FOREIGN PATENT DOCUMENTS

| EP | 1 741 792 A1 | 1/2007 |
|---|---|---|
| GB | 2360586 A * | 9/2001 |
| WO | 2005/103291 A1 | 11/2005 |
| WO | 2006/045476 A2 | 5/2006 |
| WO | WO 2006045476 A2 * | 5/2006 |
| WO | 2008/130970 A1 | 10/2008 |

OTHER PUBLICATIONS

Wright et al. (Biorg. Med. Chem. Lett. 2003, 13, 2055-2058).*
Salituro et al., "3-(2-Carboxyindol-3-yl)prpionic Acid-Based Antagonists of the N-Methyl-D-aspartic Acid Receptor Associated Glycine Binding Site", Journal of Medicinal Chemistry, 1992, 35(10), 1791-1799, XP-001199577.
Norregaard et al., "EB12, GPR18, and GPR17—Three Structurally Related but Biologically Distinct 7TM Receptors", Current Topics in Medicinal Chemistry, 2011, 11(6), 618-628, XP009154371.
Eberini et al., "In silico identification of new ligands for GPR17: a promising therapeutic target for neurodegenerative diseases", Journal of Computer-Aided Molecular Design, 2011, 25(8), 743-752, XP019955577.
Ciana et al., "The orphan receptor GPR17 identified as a new dual uracil nucleotides/cysteinyl-leukotrienes receptor", The EMBO Journal, 2006, 25(19), 4615-4627.
Blasius et al., "A novel orphan G protein-coupled receptor primarily expressed in the brain is localized on human chromosomal band 2q21", Journal of Neurochemistry, 1998, 70(4), 1357-1365.
Benned-Jensen et al., Distinct expression and ligand-binding profiles of two contitutively active GPR17 splice variants, British Journal of Pharmacology, 2010,159(5), 1092-1105.
Chen et al., "The oligodendrocyte-specific G protein-coupled receptor GPR17 is a cell-intrinsic timer of myelination", Nature Neuroscience, 2009, 12(11), 1398-1406.
Ceruti et al., "The P2Y-like receptor GPR17 as a sensor of damage and a new potential target in spinal cord injury", Brain: A Journal of Neurology, 2009,Vol. 132(Pt 8), 2206-2218.
Pugliese et al., "Functional characterization of two isoforms of the P2Y-like receptor GPR17: [35S]GTPγS binding and eletrophysiological studies in 1321N1 cells", Am J Physiol Cell Physiol, 2009, vol. 297, C1028-C1040.
Maekawa et al., "GPR17 is a negative regulator of the cysteinyl leukotriene 1 receptor response to leukotriene D4", PNAS, 2009, 106(28), 11685-11690.
Wright et al, "3-(2-Carboxy-ethyl)-4,6-dichloro-1H-indole-2-carboxylic Acid: An allosteric inhibitor of fructose-1,6-bisphosphatase at the AMP site", Bioorganic & Medicinal Chemistry Letters, 2003, vol. 13, 2055-2058.
Maggio et al., "Reconstitution of functional muscarinic receptors by co-epxression of amino- and carboxyl-terminal receptor fragments", FEBS Letters, 1993, 319(1,2), 195-200.
Schöneberg et al, "Plasma membrane localization and functional rescue of truncated forms of a G protein-coupled receptor", The Journal of Biological Chemistry, 1995, 270(30), 18000-18006.
Dayhoff et al., "Matrices for detecting distant relationships", Atlas of Protein Sequence and Structure, 5, Suppl. 3, 353-358.
Dufresne et al., "Patent searches for genetic sequences: How to retrieve relevant records from patented sequence databases", Nature Biotechnology, 2002, vol. 20, 1269-1271.
Andree et al., "A comparative study of patent sequence databases", World Patent Information, 2008, 30(4), 300-308.
Tatusova et al., "Blast 2 Sequences, a new tool for comparing protein and nucleotide sequences", FEMS Microbiology Letters, 1999, vol. 174, 247-250.
Altschul et al, "Basic local alignment search tool", J. Mol. Biol., 1990, vol. 215, 403-410.
Wheeler et al., "Database resources of the national center for biotechnology information", Nucleic Acids Research, 2007, vol. 35, D5-D12.
Pearson, "Rapid Sequence Comparison: Rapid and sensitive sequence comparison with FASTP and FASTA", Methods in Enzymology, 1990, vol. 183, 63-98.
Smith et al., "Identification of common molecular subsequences", Journal of Molecular Biology 1981, vol. 147, 195-197. Takahashi et al., "Novel Indonline-Based Acyl-CoA: Cholesterol Acyltransferase Inhibitor with Antiperoxidative Activity: Improvement of Physicochemical Properties and Biological Activities by Introduction of Carboxylic Acid", Journal of Medicinal Chemistry, 2008, vol. 51, 4823-4833.

* cited by examiner

*Primary Examiner* — Jeffrey S. Lundgren
*Assistant Examiner* — Michael Schmitt
(74) *Attorney, Agent, or Firm* — McDonnell Boehnen Hulbert & Berghoff LLP

(57) ABSTRACT

The present invention is related to a method of determining a test compound's ability to modify the biological activity of a GPR17. Said method comprises, among others, the step of contacting the test compound with a GPR17, or a functional GPR17 fragment in the presence of a suitable amount of a GPR17 agonist of formula I.

7 Claims, 7 Drawing Sheets

SEQUENCE LISTING

<160> NUMBER OF SEQ ID NOS: 4

<210> SEQ ID NO 1
<211> LENGTH: 339
<212> TYPE: PRT
<213> ORGANISM: human

<400> SEQUENCE: 1

```
Met Asn Gly Leu Glu Val Ala Pro Pro Gly Leu Ile Thr Asn Phe Ser
1               5                   10                  15

Leu Ala Thr Ala Glu Gln Cys Gly Gln Glu Thr Pro Leu Glu Asn Met
            20                  25                  30

Leu Phe Ala Ser Phe Tyr Leu Leu Asp Phe Ile Leu Ala Leu Val Gly
        35                  40                  45

Asn Thr Leu Ala Leu Trp Leu Phe Ile Arg Asp His Lys Ser Gly Thr
    50                  55                  60

Pro Ala Asn Val Phe Leu Met His Leu Ala Val Ala Asp Leu Ser Cys
65                  70                  75                  80
```

```
Val Leu Val Leu Pro Thr Arg Leu Val Tyr His Phe Ser Gly Asn His
                85                  90                  95
Trp Pro Phe Gly Glu Ile Ala Cys Arg Leu Thr Gly Phe Leu Phe Tyr
            100                 105                 110
Leu Asn Met Tyr Ala Ser Ile Tyr Phe Leu Thr Cys Ile Ser Ala Asp
        115                 120                 125
Arg Phe Leu Ala Ile Val His Pro Val Lys Ser Leu Lys Leu Arg Arg
    130                 135                 140
Pro Leu Tyr Ala His Leu Ala Cys Ala Phe Leu Trp Val Val Val Ala
145                 150                 155                 160
Val Ala Met Ala Pro Leu Leu Val Ser Pro Gln Thr Val Gln Thr Asn
                165                 170                 175
His Thr Val Val Cys Leu Gln Leu Tyr Arg Glu Lys Ala Ser His His
            180                 185                 190
Ala Leu Val Ser Leu Ala Val Ala Phe Thr Phe Pro Phe Ile Thr Thr
        195                 200                 205
Val Thr Cys Tyr Leu Leu Ile Ile Arg Ser Leu Arg Gln Gly Leu Arg
    210                 215                 220
Val Glu Lys Arg Leu Lys Thr Lys Ala Val Arg Met Ile Ala Ile Val
225                 230                 235                 240
Leu Ala Ile Phe Leu Val Cys Phe Val Pro Tyr His Val Asn Arg Ser
                245                 250                 255
Val Tyr Val Leu His Tyr Arg Ser His Gly Ala Ser Cys Ala Thr Gln
            260                 265                 270
Arg Ile Leu Ala Leu Ala Asn Arg Ile Thr Ser Cys Leu Thr Ser Leu
        275                 280                 285
Asn Gly Ala Leu Asp Pro Ile Met Tyr Phe Phe Val Ala Glu Lys Phe
    290                 295                 300
Arg His Ala Leu Cys Asn Leu Leu Cys Gly Lys Arg Leu Lys Gly Pro
305                 310                 315                 320
Pro Pro Ser Phe Glu Gly Lys Thr Asn Glu Ser Ser Leu Ser Ala Lys
                325                 330                 335
Ser Glu Leu

<210> SEQ ID NO 2
<211> LENGTH: 367
<212> TYPE: PRT
<213> ORGANISM: human

<400> SEQUENCE: 2

Met Ser Lys Arg Ser Trp Trp Ala Gly Ser Arg Lys Pro Pro Arg Glu
1               5                   10                  15
Met Leu Lys Leu Ser Gly Ser Asp Ser Ser Gln Ser Met Asn Gly Leu
                20                  25                  30
Glu Val Ala Pro Pro Gly Leu Ile Thr Asn Phe Ser Leu Ala Thr Ala
            35                  40                  45
Glu Gln Cys Gly Gln Glu Thr Pro Leu Glu Asn Met Leu Phe Ala Ser
        50                  55                  60
Phe Tyr Leu Leu Asp Phe Ile Leu Ala Leu Val Gly Asn Thr Leu Ala
65                  70                  75                  80
Leu Trp Leu Phe Ile Arg Asp His Lys Ser Gly Thr Pro Ala Asn Val
                85                  90                  95
Phe Leu Met His Leu Ala Val Ala Asp Leu Ser Cys Val Leu Val Leu
            100                 105                 110
Pro Thr Arg Leu Val Tyr His Phe Ser Gly Asn His Trp Pro Phe Gly
```

```
            115                 120                 125
Glu Ile Ala Cys Arg Leu Thr Gly Phe Leu Phe Tyr Leu Asn Met Tyr
130                 135                 140

Ala Ser Ile Tyr Phe Leu Thr Cys Ile Ser Ala Asp Arg Phe Leu Ala
145                 150                 155                 160

Ile Val His Pro Val Lys Ser Leu Lys Leu Arg Arg Pro Leu Tyr Ala
                165                 170                 175

His Leu Ala Cys Ala Phe Leu Trp Val Val Ala Val Ala Met Ala
                180                 185                 190

Pro Leu Leu Val Ser Pro Gln Thr Val Gln Thr Asn His Thr Val Val
                195                 200                 205

Cys Leu Gln Leu Tyr Arg Glu Lys Ala Ser His His Ala Leu Val Ser
210                 215                 220

Leu Ala Val Ala Phe Thr Phe Pro Phe Ile Thr Val Thr Cys Tyr
225                 230                 235                 240

Leu Leu Ile Ile Arg Ser Leu Arg Gln Gly Leu Arg Val Glu Lys Arg
                245                 250                 255

Leu Lys Thr Lys Ala Val Arg Met Ile Ala Ile Val Leu Ala Ile Phe
                260                 265                 270

Leu Val Cys Phe Val Pro Tyr His Val Asn Arg Ser Val Tyr Val Leu
                275                 280                 285

His Tyr Arg Ser His Gly Ala Ser Cys Ala Thr Gln Arg Ile Leu Ala
                290                 295                 300

Leu Ala Asn Arg Ile Thr Ser Cys Leu Thr Ser Leu Asn Gly Ala Leu
305                 310                 315                 320

Asp Pro Ile Met Tyr Phe Phe Val Ala Glu Lys Phe Arg His Ala Leu
                325                 330                 335

Cys Asn Leu Leu Cys Gly Lys Arg Leu Lys Gly Pro Pro Ser Phe
                340                 345                 350

Glu Gly Lys Thr Asn Glu Ser Ser Leu Ser Ala Lys Ser Glu Leu
                355                 360                 365

<210> SEQ ID NO 3
<211> LENGTH: 339
<212> TYPE: PRT
<213> ORGANISM: rat

<400> SEQUENCE: 3

Met Asp Gly Leu Glu Thr Ala Leu Pro Ser Leu Thr Asp Asn Ala Ser
1               5                   10                  15

Leu Ala Tyr Ser Glu Gln Cys Gly Gln Glu Thr Pro Leu Glu Asn Met
                20                  25                  30

Leu Phe Ala Cys Phe Tyr Leu Leu Asp Phe Ile Leu Ala Phe Val Gly
            35                  40                  45

Asn Ala Leu Ala Leu Trp Leu Phe Ile Trp Asp His Lys Ser Gly Thr
50                  55                  60

Pro Ala Asn Val Phe Leu Met His Leu Ala Val Ala Asp Leu Ser Cys
65                  70                  75                  80

Val Leu Val Leu Pro Thr Arg Leu Val Tyr His Phe Ser Gly Asn His
                85                  90                  95

Trp Pro Phe Gly Glu Ile Pro Cys Arg Leu Thr Gly Phe Leu Phe Tyr
                100                 105                 110

Leu Asn Met Tyr Ala Ser Ile Tyr Phe Leu Thr Cys Ile Ser Ala Asp
            115                 120                 125

Arg Phe Leu Ala Ile Val His Pro Val Lys Ser Leu Lys Leu Arg Arg
```

```
                    130                 135                 140
Pro Leu Tyr Ala His Leu Ala Cys Ala Phe Leu Trp Ile Val Val Ala
145                 150                 155                 160

Val Ala Met Ala Pro Leu Leu Val Ser Pro Gln Thr Val Gln Thr Asn
                165                 170                 175

His Thr Val Val Cys Leu Gln Leu Tyr Arg Glu Lys Ala Ser His His
            180                 185                 190

Ala Leu Ala Ser Leu Ala Val Ala Phe Thr Phe Pro Phe Ile Thr Thr
        195                 200                 205

Val Thr Cys Tyr Leu Leu Ile Ile Arg Ser Leu Arg Gln Gly Pro Arg
    210                 215                 220

Ile Glu Lys His Leu Lys Asn Lys Ala Val Arg Met Ile Ala Met Val
225                 230                 235                 240

Leu Ala Ile Phe Leu Ile Cys Phe Val Pro Tyr His Ile His Arg Ser
                245                 250                 255

Val Tyr Val Leu His Tyr Arg Gly Gly Gly Thr Ser Cys Ser Ala Gln
            260                 265                 270

Arg Ala Leu Ala Leu Gly Asn Arg Ile Thr Ser Cys Leu Thr Ser Leu
        275                 280                 285

Asn Gly Ala Leu Asp Pro Val Met Tyr Phe Phe Val Ala Glu Lys Phe
    290                 295                 300

Arg His Ala Leu Cys Asn Leu Leu Cys Ser Lys Arg Leu Thr Gly Pro
305                 310                 315                 320

Pro Pro Ser Phe Glu Gly Lys Thr Asn Glu Ser Ser Leu Ser Ala Arg
                325                 330                 335

Ser Glu Leu

<210> SEQ ID NO 4
<211> LENGTH: 339
<212> TYPE: PRT
<213> ORGANISM: mouse

<400> SEQUENCE: 4

Met Asn Gly Leu Glu Ala Ala Leu Pro Ser Leu Thr Asp Asn Ser Ser
1               5                   10                  15

Leu Ala Tyr Ser Glu Gln Cys Gly Gln Glu Thr Pro Leu Glu Asn Met
            20                  25                  30

Leu Phe Ala Cys Phe Tyr Leu Leu Asp Phe Ile Leu Ala Phe Val Gly
        35                  40                  45

Asn Ala Leu Ala Leu Trp Leu Phe Ile Trp Asp His Lys Ser Gly Thr
    50                  55                  60

Pro Ala Asn Val Phe Leu Met His Leu Ala Val Ala Asp Leu Ser Cys
65                  70                  75                  80

Val Leu Val Leu Pro Thr Arg Leu Val Tyr His Phe Ser Gly Asn His
                85                  90                  95

Trp Pro Phe Gly Glu Ile Pro Cys Arg Leu Thr Gly Phe Leu Phe Tyr
            100                 105                 110

Leu Asn Met Tyr Ala Ser Ile Tyr Phe Leu Thr Cys Ile Ser Ala Asp
        115                 120                 125

Arg Phe Leu Ala Ile Val His Pro Val Lys Ser Leu Lys Leu Arg Arg
    130                 135                 140

Pro Leu Tyr Ala His Leu Ala Cys Ala Phe Leu Trp Ile Val Val Ala
145                 150                 155                 160

Val Ala Met Ala Pro Leu Leu Val Ser Pro Gln Thr Val Gln Thr Asn
                165                 170                 175
```

```
His Thr Val Val Cys Leu Gln Leu Tyr Arg Glu Lys Ala Ser His His
            180                 185                 190

Ala Leu Ala Ser Leu Ala Val Ala Phe Thr Phe Pro Phe Ile Thr Thr
            195             200                 205

Val Thr Cys Tyr Leu Leu Ile Ile Arg Ser Leu Arg Gln Gly Pro Arg
    210                 215                 220

Ile Glu Lys His Leu Lys Asn Lys Ala Val Arg Met Ile Ala Met Val
225             230                 235                 240

Leu Ala Ile Phe Leu Ile Cys Phe Val Pro Tyr His Ile His Arg Ser
                245                 250                 255

Val Tyr Val Leu His Tyr Arg Gly Gly Gly Thr Ser Cys Ala Ala Gln
                260                 265                 270

Arg Ala Leu Ala Leu Gly Asn Arg Ile Thr Ser Cys Leu Thr Ser Leu
            275                 280                 285

Asn Gly Ala Leu Asp Pro Val Met Tyr Phe Phe Val Ala Glu Lys Phe
            290                 295                 300

Arg His Ala Leu Cys Asn Leu Leu Cys Ser Lys Arg Leu Thr Gly Pro
305                 310                 315                 320

Pro Pro Ser Phe Glu Gly Lys Thr Asn Glu Ser Ser Leu Ser Ala Arg
                325                 330                 335

Ser Glu Leu
```

METHODS OF IDENTIFYING MODULATORS OF GPR17

BACKGROUND

G-protein coupled receptors (GPCRs) constitute the largest family of membrane receptors in the cell. They transduce extracellular signals to intracellular effector systems and are involved in a large variety of physiological phenomena, therefore representing the most common target of pharmaceutical drugs although only a small percentage of GPCRs are targeted by current therapies.

GPCRs respond to a wide range of ligands. Due to the progress of human genome sequencing, for about 25% out of the more than 400 GPCRs (not including the olfactory GPCRs) that have been identified, a defined physiologically relevant ligand is still lacking. These receptors are known as "orphan GPCRs". "Deorphanization" and identification of their in vivo roles is expected to clarify novel regulatory mechanisms and, therefore, to disclose novel drug targets. Whether GPR17 is such an orphan receptor is still a matter of debate. Phylogenetically, GPR17 is most closely related to the nucleotide P2Y receptors and the cysteinylleukotriene (CysLT1, CysLT2) receptors, with an amino acid sequence identity of between about 30 and about 35%, respectively.

Multiple-tissue Northern blot and RT-PCR analyses indicate a predominant expression of GPR17 in the central nervous system (CNS) (Clana et al., 2006, EMBO J. 25(19): 4615; Blasius et al., 1998, J Neurochem 70(4): 1357) and additionally in heart and kidney, i.e. organs typically undergoing ischemic damage. Two GPR17 isoforms have been identified differing only by the length of their N-terminus. The short GPR17 isoform encodes a 339 amino acid—residue protein with typical rhodopsin type-seven transmembrane motifs. The long isoform encodes a receptor with a 28 amino acid longer N-terminus (Blasius et al., 1998). GPR17 is highly conserved among vertebrate species (~90% identity of amino acid sequence to both mouse and rat orthologs), which may constitute an advantageous feature for development of small molecule ligands and animal models in a drug discovery context.

In the original deorphaning report, GPR17 was identified as dual receptor for uracil nucleotides and cysteinyl-leukotrienes (cysLTs) LTC4 and LTD4, respectively based on $^{35}$SGTPγS binding and cAMP inhibition assays as well as single cell calcium imaging (Clana et al., 2006). Evidence for GPR17 functionality was provided in different cellular backgrounds such as 1321N1, COS7, CHO, and HEK293 cells (Clana et al., 2006). Subsequently, an independent study confirmed activation of GPR17 by uracil nucleotides but failed to recapitulate activation by CysLTs (Benned-Jensen, 2010, Br J Pharmacol, 159(5): 1092). Yet another very recent report (Maekawa et al., 2009) suggested lack of GPR17 responsiveness to both uracil nucleotides and CysLTs across three different cellular backgrounds stably expressing GPR17 (1321N1, CHO, HEK293 cells). Instead a novel regulatory role for GPR17 was proposed: GPR17—upon coexpression with CysLT1—rendered CysLT1 unresponsive to its endogenous lipid mediators LTC4 and LTD4. Clearly, additional in vitro investigations are required to probe GPR17 pharmacology and function in more depth.

Drugs modulating the GPR 17 activity may have neuroprotective, anti-inflammatory and anti-ischemic effects and may thus be useful for the treatment of cerebral, cardiac and renal ischemia, and stroke (WO 2006/045476). WO 2005/103291 disclosed analgetic effects of a GPR 17 agonist and proposed the use of GPR 17 agonists for treating neuropathic pain. Moreover, evidence is accumulating that GPR 17 is involved in myelination processes and that GPR 17 antagonists can be valuable drugs for the treatment or alleviation of myelination disorders such as multiple sclerosis or spinal cord injury (Chen et al, Nature neuroscience 2009, 12(11): 1398-406; Ceruti et al; Brain: a journal of neurology 2009 132(Pt 8):2206-18). The identification of potent and selective GPR 17 modulators could thus be of significant relevance in the treatment of these serious diseases.

Identification of an activating ligand is a prerequisite to search for compounds that modulate GPR17 activity. Although activation by uracil nucleotides and cysteinyl-leukotrienes of GPR17 has been reported (Clana et al., 2006; Pugliese et al., 2009, Am J Physiol Cell Physiol 297: C1028), these endogenous signalling molecules do not display functional activity in different cell lines (1321N1, CHO, HEK) engineered to stably express the short isoform of GPR17 in our laboratory. In agreement with our observations, inactivity of these ligand classes has also been observed in a recent study (Maekawa et al., 2009, PNAS, US, 106(28): 11685). Another independent laboratory was also not able to confirm cysteinyl-leukotrienes as GPR17 agonists (Benned-Jensen, 2010), while depending on the GPR 17 isoform tested some functional activity of uracil nucleotides was seen, although only at low, or high micromolar concentrations, respectively.

WO 2005/103291 suggested the endogenous molecules 5 amino levulinic acid (5-ALA) and porphobilinogen (PBG) as activating ligands for GPR17, and a screening assay using these GPR 17 agonists. However, the reported affinity of 5-ALA and PBG is quite low and the amounts needed in the assays are significant, namely in the three digit micromolar range for 5-ALA or even in the mM range for PBG, which make both compounds not well suited for use in routine screening assays or even high throughput screenings. Moreover, PBG is a chemical unstable, reactive compound which rapidly decomposes after exposure to air and light, making it impractical to handle on a routine basis.

Accordingly, a need exists for the identification of improved GPR 17 agonists, which can be used as an easy and cheep but robust and reliable tool for the identification of GPR17 antagonists in various experimental settings.

3-(2-Carboxyethyl)-4,6-dichloro-1H-indole-2-carboxylic acid and some analogs had been previously described as allosteric inhibitors of fructose-1,6-biphosphatase (Wright et al, MBCL 2003, 13, 2055), and as antagonists of the NMDA receptor associated glycine binding site (Salituro, J Med Chem, 1992, 35, 1791; U.S. Pat. No. 4,960,786). However, these compounds have not yet been described as GPR17 modulators.

SUMMARY OF THE INVENTION

We have now detected that 3-(2-carboxyethyl)-4,6-dichloro-1H-indole-2-carboxylic acid (herein also referred to as RA-II-150) and other compounds of formula I, infra, are agonists for GPR17. In contrast to cysteinylleukotrienes and uracil nucleotides, we have found that RA-II-150 and other compounds of formula I and their salts activate GPR17 irrespective of the cellular background, i.e. they activate the receptor in a number of different cell lines such as 1321N1 astrocytoma cells, human embryonic kidney HEK293 cells, and Chinese hamster ovary (CHO) cells.

Table 1 and FIG. 1 disclose concentration-effect curves for the mobilization of intracellular $Ca^{2+}$ in human GPR17

(hGPR17) transfected 1321 and CHO cells, respectively, by RA-II-150 and other compounds of formula I. None of these identified GPR17 agonists display activity in native cells that lack GPR17.

Table 1. Potencies and efficacies of RA-II-150 and other compounds of formula I in the 1321N1-GPR17 and CHO-GPR17 cell systems were determined from the calcium mobilization assays described in Example 2, below. Data in recombinant 1321N1 and CHO cells are normalized to the response of 30 μM and 0.3 μM RA-II-150 (column 3), respectively. Unspecific effects of active compounds are tested on native 1321N1 or CHO-K1 cells. Here, data are normalized to the response of 100 μM carbachol or 100 μM ATP (column 4) (n=3-4).

TABLE 1

| Chemical structure and internal designation of selected compounds of formula I | $pEC_{50}$ (±SEM) 1321N1-GPR17/ CHO-GPR17 | % of response of 30 μM compound (±SEM) 1321N1-GPR17/ CHO-GPR17 cells | % response of 30 μM compound (±SEM) Native 1321N1 cells/CHO-K1 cells |
|---|---|---|---|
| RA-II-150 | 6.09 (0.06)/ 8.20 (0.08) | 100 (0)/ 100 (0) (0.3 μM compound) | 0 (3)/ 0 (1) (0.1 μM compound) |
| RA-III-40 | 5.28 (0.08)/ 6.73 (0.12) | 80 (6)/ 85 (5) (1 μM compound) | 1 (1)/ 1 (1) (1 μM compound) |
| RA-III-55 | 4.86 (0.10)/ 6.47 (0.05) | 76 (6)/ 68 (2) (1 μM compound) | 1 (1)/ 1 (1) (1 μM compound) |
| KL16-1 | 5.43 (0.14)/ 7.69 (0.10) | 84 (6)/ 94 (7) (1 μM compound) | 4 (3)/ 1 (2) (0.3 μM compound) |

TABLE 1-continued
| Chemical structure and internal designation of selected compounds of formula I | pEC$_{50}$ (±SEM) 1321N1-GPR17/ CHO-GPR17 | % of response of 30 μM compound (±SEM) 1321N1-GPR17/ CHO-GPR17 cells | % response of 30 μM compound (±SEM) Native 1321N1 cells/CHO-K1 cells |
|---|---|---|---|
| 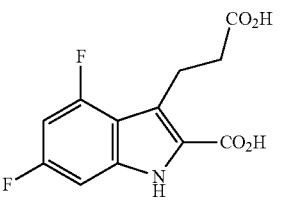 KL28 | 5.13 (0.13)/ 6.79 (0.10) | 77 (2)/ 97 (5) (3 μM compound) | 2 (1)/ 1 (2) (3 μM compound) |
| 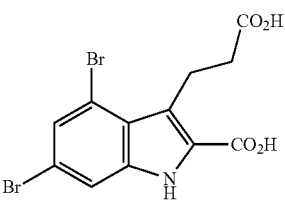 KL126 | 6.71 (0.01)/ 7.87 (0.16) | 106 (1) (10 μM compound)/ 89 (2) (0.3 μM compound) | 0 (1)/ 0 (0) (0.3 μM compound) |
| 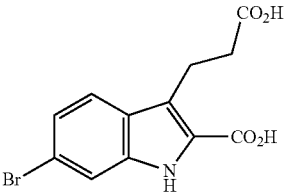 SAL006-1 | 5.50 | | |
| 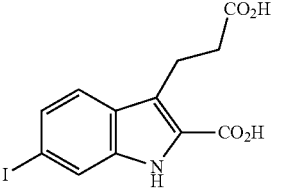 SAL009-1 | 6.15 | | |
| 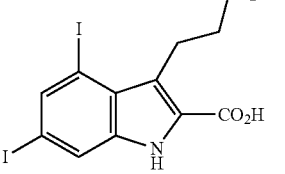 SAL019 | 5.32 | | |

TABLE 1-continued

| Chemical structure and internal designation of selected compounds of formula I | pEC$_{50}$ (±SEM) 1321N1-GPR17/ CHO-GPR17 | % of response of 30 µM compound (±SEM) 1321N1-GPR17/ CHO-GPR17 cells | % response of 30 µM compound (±SEM) Native 1321N1 cells/CHO-K1 cells |
|---|---|---|---|
| SAL016 (4,6-diphenyl indole with CO$_2$H at 2-position and CH$_2$CH$_2$CO$_2$H at 3-position) | 5.52 | | |
| (6-phenyl indole with CO$_2$H at 2-position and CH$_2$CH$_2$CO$_2$H at 3-position) | 6.14 | | |

The following GPR17 agonists which are also structures of formula I also form part of the disclosure:

TABLE 2

| Structure | Name |
|---|---|
| OLE12 | 3-(2-carboxyethyl)-6,7-dichloro-1H-indole-2-carboxylic acid (3-(2-Carboxy-6,7-dichloroindol-3-yl)propionic acid) |
| OLE16 | 3-(2-carboxyethyl)-6-chloro-7-fluoro-1H-indole-2-carboxylic acid (3-(2-Carboxy-6-chloro-7-fluoroindol-3-yl)propionic acid) |

TABLE 2-continued

| Structure | Name |
|---|---|
| OLE33 | 3-(2-carboxyethyl)-6-bromo-2-carboxy-7-fluoro-1H-indole-2-carboxylic acid (3-(6-Bromo-2-carboxy-7-fluoroindol-3-yl)propionic acid) |
| OLE20 | 3-(2-carboxyethyl)-4,6-dimethoxy-1H-indole-2-carboxylic acid (3-(2-Carboxy-4,6-dimethoxyindol-3-yl)propionic acid) |

TABLE 2-continued

| Structure | Name |
|---|---|
| OLE37 | 3-(2-carboxyethyl)-6-phenoxy1H-indole-2-carboxylic acid, (3-(2-Carboxy-6-phenoxyindol-3-yl)propionic acid) |
| OLE41 | 3-(2-carboxyethyl)-6-benzyl-2-carboxy-1H-indole-2-carboxylic acid (3-(6-Benzyl-2-carboxyindol-3-yl)propionic acid) |
| OLE42 | 3-(2-carboxyethyl)-4,6-dihydroxy-1H-indole-2-carboxylic acid (3-(2-Carboxy-4,6-dihydroxyindol-3-yl)propionic acid) |
| OLE44 | 3-(2-carboxyethyl)-6-(4-fluorophenyl)-1H-indol-2-carboxylic acid, (3-[2-Carboxy-6-(4-fluoropheny)indol-3-yl]propionic acid) |
| OLE46 | 3-(2-carboxyethyl)-6-furanyl-1H-indole-2-carboxylic acid, (3-(2-Carboxy-6-furanylindol-3-yl)propionic acid) |
| OLE48 | 3-(2-carboxyethyl)-6-thienyl-1H-indole-2-carboxylic acid, (3-(2-Carboxy-6-thienylindol-3-yl)propionic acid) |
| OLE52 | 3-(2-carboxyethyl)-7-fluoro-6-phenyl-1H-indole-2-carboxylic acid (3-(2-Carboxy-7-fluoro-6-phenylindol-3-yl)propionic acid) |
| OLE52 | 3-(2-carboxyethyl)-6-(4-fluorophenyl)-7-fluoro-1H-indol-2-carboxylic acid, (3-[2-Carboxy-6-(4-fluorophenyl)-7-fluoroindol-3-yl]propionic acid) |
| OLE54 | 3-(2-carboxyethyl)-6-furanyl-7-fluoro-1H-indole-2-carboxylic acid (3-(2-Carboxy-6-furanyl-7-fluoroindol-3-yl)propionic acid) |
| OLE56 | 3-(2-carboxyethyl)-6-thienyl-7-fluoro-1H-indole-2-carboxylic acid, (3-(2-Carboxy-6-thienyl-7-fluoroindol-3-yl)propionic acid) |

A comparison of a representative GPR17 agonist of the present invention, RA-II-150, with the putative GPR 17 agonists 5-ALA and PBG (see WO 2005/103291) revealed a higher affinity and selectivity of the presently disclosed GPR 17 agonists. While the inventors of the present application were able to confirm the activation of GPR17 by 5-ALA, all attempts to activate GPR 17 with porphobilinogen failed. Also, a GPR17-independent inhibition of forskolin stimulated adenylylcyclase activity in GPR17CHO cells was recognized after 5-ALA addition, thus questioning the specificity of GPR17 activation by 5-ALA. Irrespective of the quality of 5ALA to serve as a selective stimulus for GPR17, it is considerably less potent (10.000 fold) as compared with the presently disclosed small molecule agonist RA-II-150 and its structural analogs (FIG. 2).

In summary, we identified small molecules with the ability to activate GPR17 with high specificity and potency and significant superiority over published GPR17 agonists. The GPR17 agonists of the present invention can be used for establishing functional GPR17 assays to search for inhibitors of said receptor to treat/prevent neurodegenerative diseases such as spinal cord injury, multiple sclerosis, cerebral, cardiac and renal ischemia, and preferably multiple sclerosis, ischemic damage and stroke.

Accordingly, one aspect of the present invention relates to small molecule GPR17 agonists, as chemically further defined below, and methods for using the agonists in the identification of and screening for GPR17 modulators, in particular GPR 17 antagonists.

One aspect of the present invention relates to screening assays comprising the GPR17 agonists of the present invention and cells, tissue or membrane fractions expressing the GPR17 receptor and/or functional active fragments thereof. In one embodiment of the invention, such screening assays may be provided, sold or offered in the form of a kit comprising all or substantially all of the components to be used in the assay described herein.

One aspect of the present invention relates to a method of identifying a test compound's ability to modulate the GPR17 activity by contacting a compound with GPR17 (or a functional fragment thereof) in the presence of a GPR17 agonist according to the present invention, and comparing the activity of GPR17 in the presence of the agonist with and without the presence of said test compound.

One aspect of the present invention relates to a method of treating or alleviating a GPR17 mediated disease, said method comprising (a) in a first step identifying a GPR17 modulator, particularly an antagonist via the screening methods and assays disclosed herein, and (b) in a subsequent step administering the GPR17 modulators identified in the 1$^{st}$ step (a) to a patient suffering from such a GPR 17 mediated disease (such as spinal cord injury, multiple sclerosis, cerebral, cardiac and renal ischemia, and preferably stroke or multiple sclerosis), preferably in the form of a pharmaceutical composition comprising one or more pharmaceutically acceptable excipients.

One aspect of the present invention relates to GPR17 modulators, preferably antagonists, identified using the methods and screening assays disclosed herein and methods for use of such modulators in therapy, particularly for the treatment or alleviation of spinal cord injury, multiple sclerosis, cerebral, cardiac and renal ischemia, and preferably of multiple sclerosis, ischemic diseases and stroke.

DETAILED DESCRIPTION OF THE INVENTION

Figure 1A:
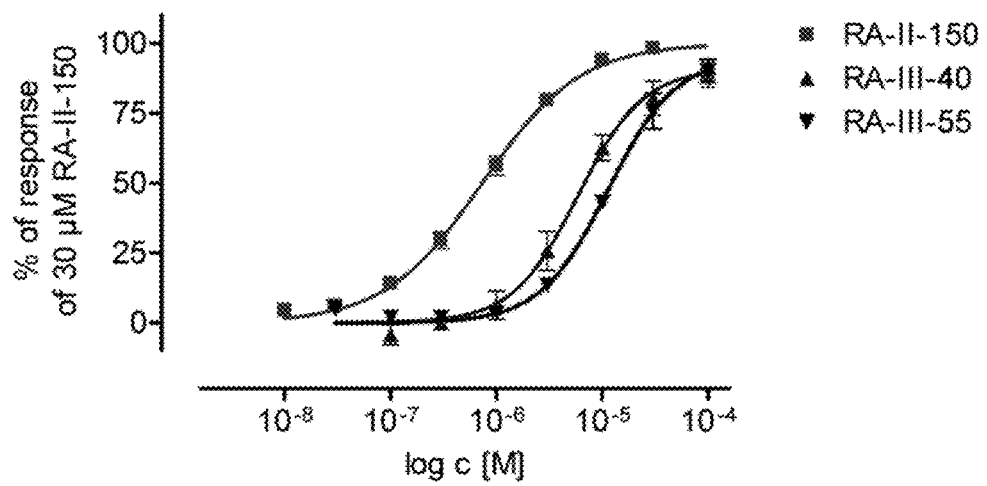
FIG. 1. Dose response curves (DRC) of compounds of formula I being active in the 1321N1 (A, B) and CHO cell systems (C, D) expressing GPR17 recombinantly (n=3-29) determined from the calcium mobilization assays of Example 2. For reference purposes the DRC of the lead compound RA-II-150 is shown in all plots (closed red squares).
Figure 1B:
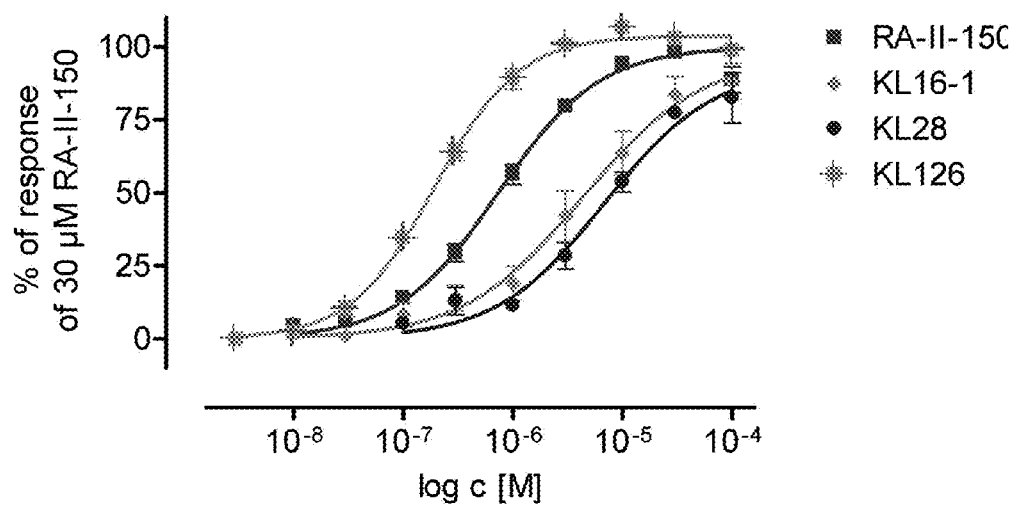
Figure 1C:
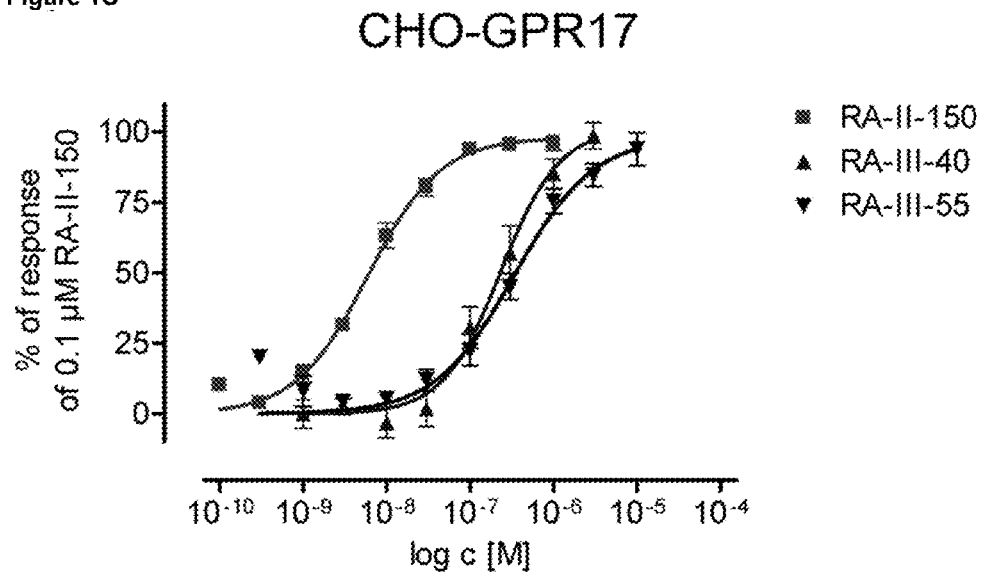
Figure 1D:
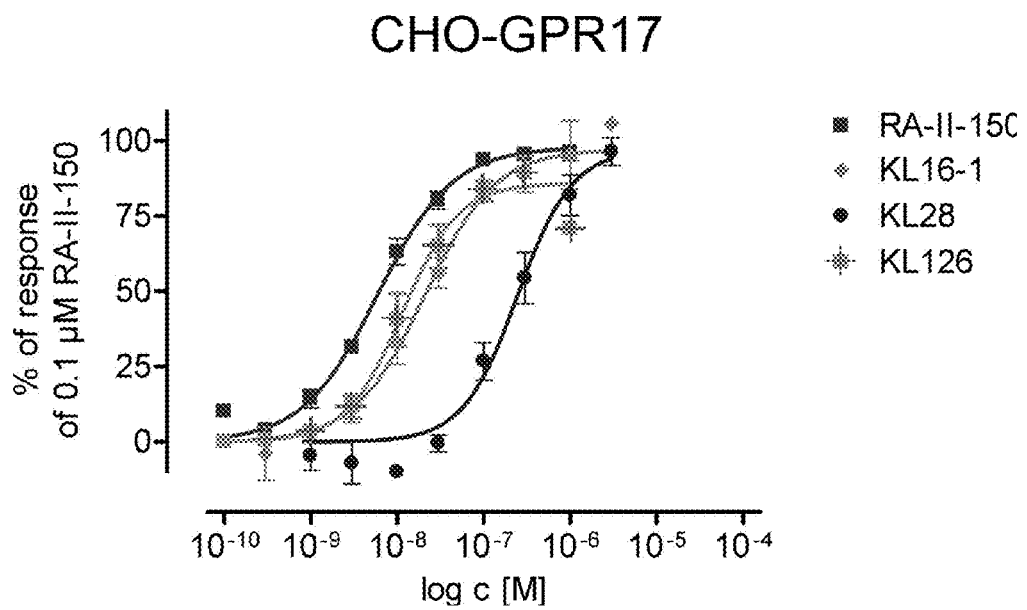
Figure 2A:
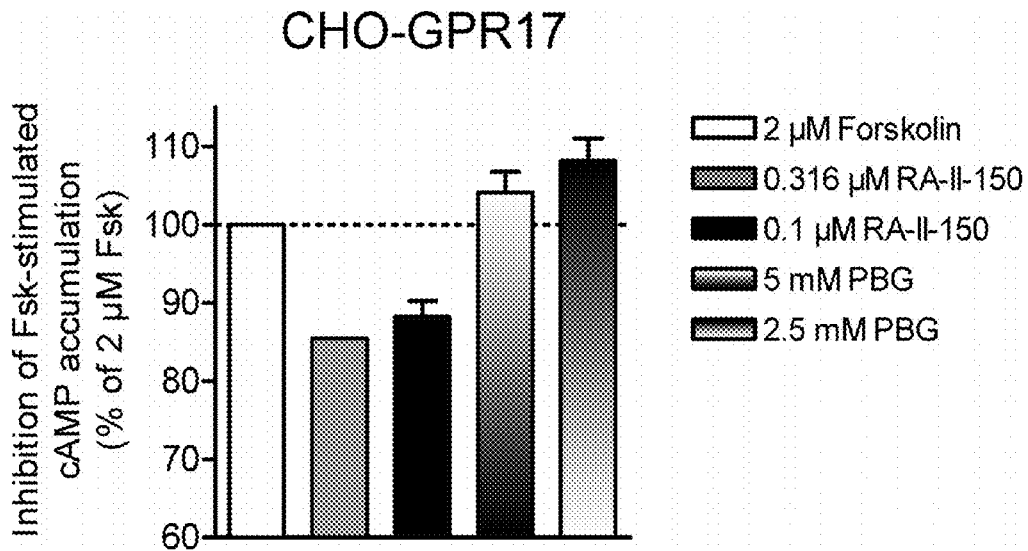
FIG. 2. Effect of RA-II-150, porphobilinogen (PBG) and 5-aminolevulinic acid (5-ALA) on forskolin-stimulated cAMP production, using the assay of Example 3. Individual concentrations of RA-II-150 and PBG were tested in CHO-GPR17 (2A) and CHO cells (2B), respectively. Concentration-response curve of RA-II-150 in CHO-GPR17 (2C). Concentration-response curves of 5-ALA ((A)—stock solved in DMSO, (B)—stock solved in water) in CHO-GPR17 (2D), corrected for the effect seen in CHO) and CHO cells (2E). cAMP levels induced by stimulation with forskolin (Fsk) were set 100%. All data are means (±s.e.m.) of two to six experiments performed in duplicates. In both figures, the left data column corresponds to the uppermost legend and so forth.
Figure 2B:
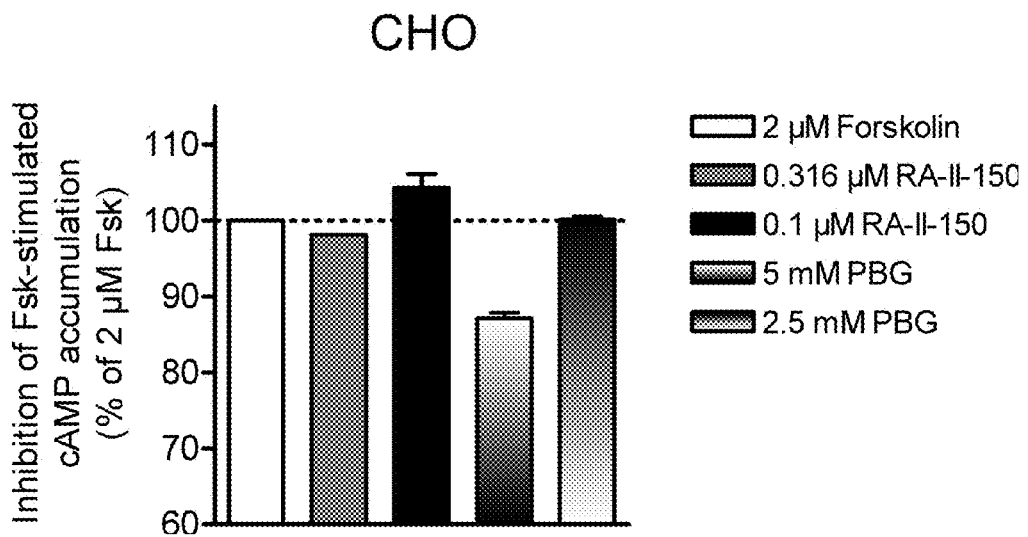
Figure 2C:
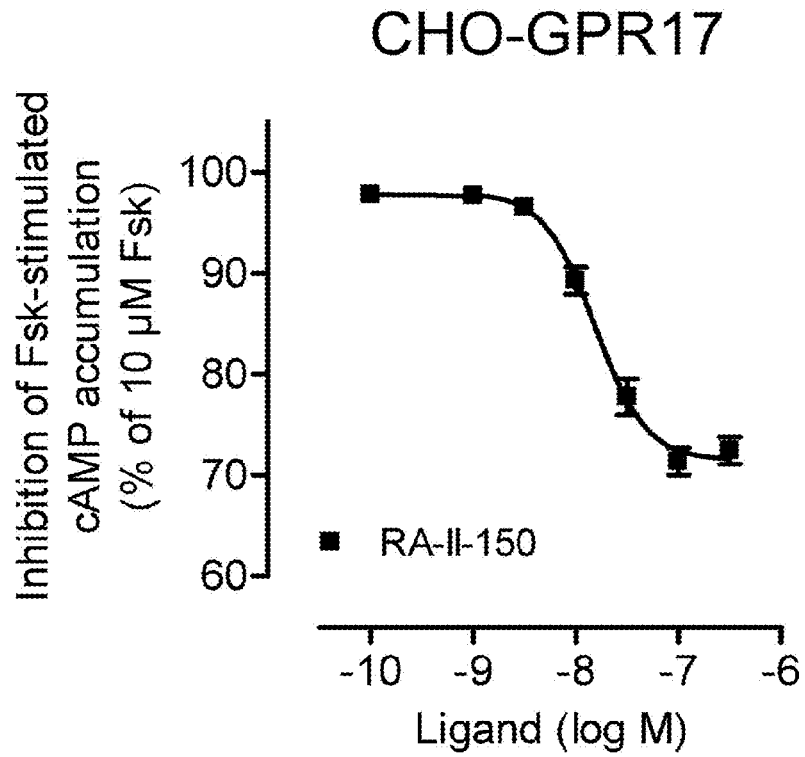
Figure 2D:
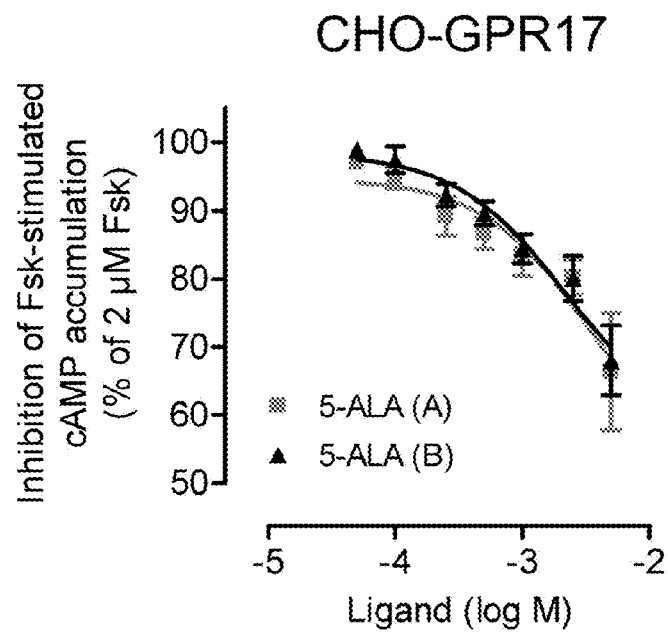
Figure 2E:
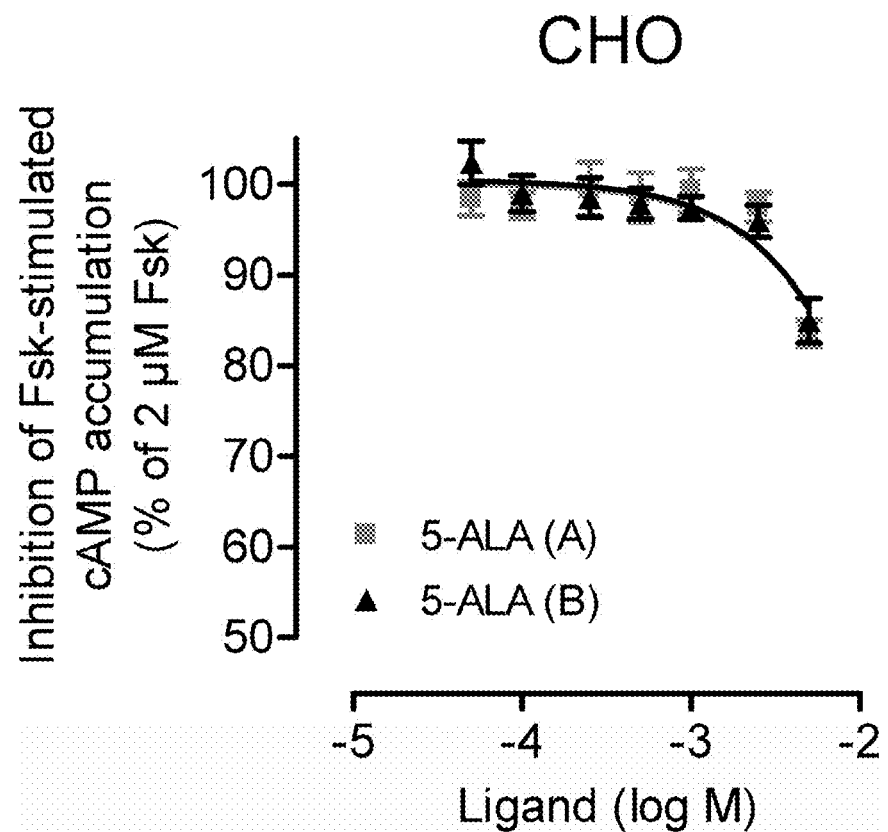
Figure 3:
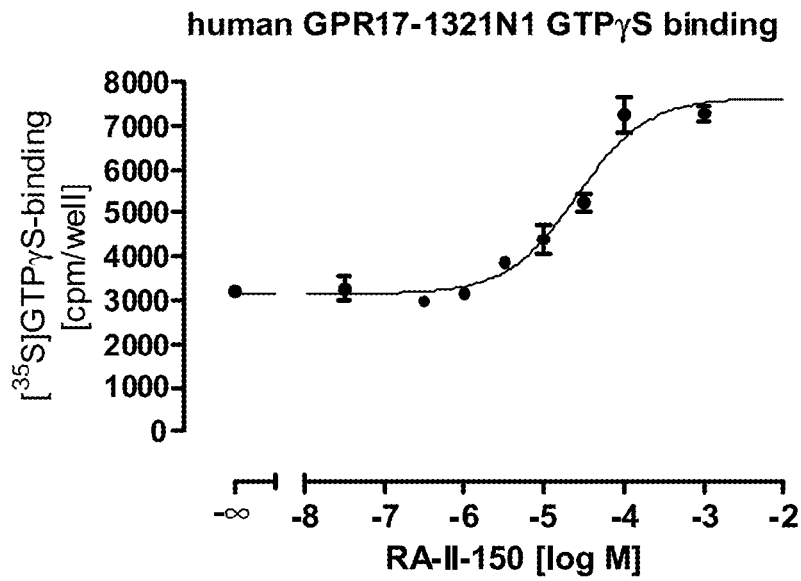
FIG. 3. Concentration-effect curve of RA-II-150 in the $^{35}$SGTPγS binding assays of Example 4 on membranes from 1321N1-GPR17 astrocytoma cells. Data are means (±s.e.m.) of a representative experiment.
Figure 4:
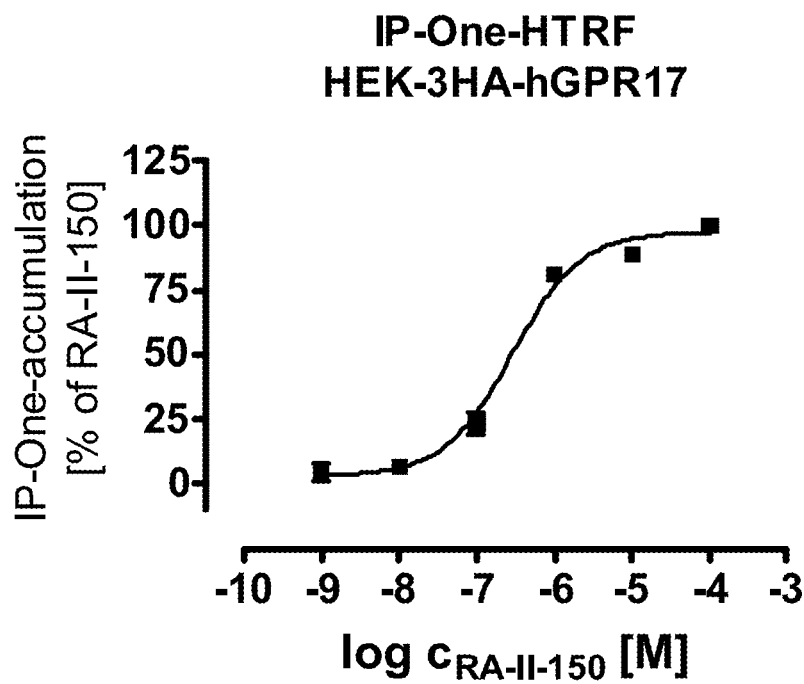
FIG. 4. Concentration-effect curve of RA-II-150 in the inositolphosphate IP1 assays of example 6 in HEK293 cells stably expressing hGPR17 tagged N-terminally with the triple HA epitope tag. Data are means (±s.e.m.) of three independent experiments.
Figure 5:
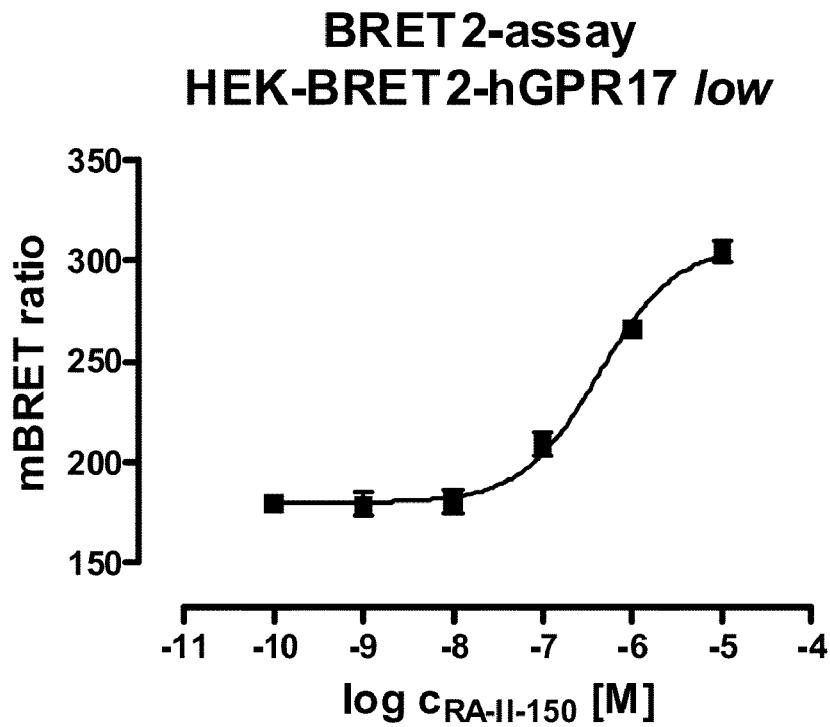
FIG. 5. Concentration-effect curve of RA-II-150 in the β-arrestin translocation assays of Example 5 using HEK293 cells co-expressing GPR17 fused to Renilla Luciferase as energy donor and β-arrestin2 fused to GFP2 as energy acceptor. Data are means (±s.e.m.) of three independent experiments FIG. 6. Concentration-inhibition curve for a GPR17 antagonist, inhibiting functional activity of GPR17 stimulated with the EC$_{80}$ of the small molecule agonist RA-II-150 in the Ca$^{2+}$ mobilization assays of Example 2 on CHO-GPR17 cells. Data are means (±s.e.m.) of five independent experiments

The present invention relates to the compounds of formula I

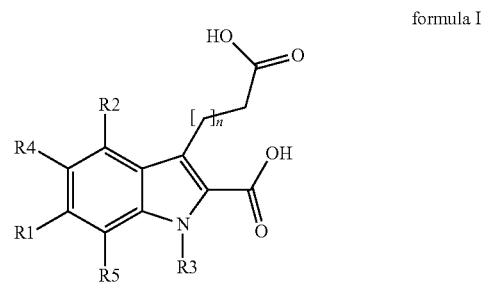

formula I and salts thereof, and methods for their use as further defined herein, wherein in formula I R1 and R2 are independently selected from the group comprising hydrogen, halogen, hydroxy, formyl, oxime, cyano, nitro, NR6R7, carboxy, carbamoyl, (C$_1$-C$_8$)alkyl, (C$_1$-C$_8$)alkyloxy, (C$_1$-C$_8$)alkylthio, (C$_2$-C$_8$)alkenyl, (C$_2$-C$_8$)alkynyl, (C$_3$-C$_8$)cycloalkyl, (C$_3$-C$_8$)cycloalkyloxy, (C$_3$-C$_8$)cycloalkylamino, aryl, heteroaryl, aryloxy, heteroaryloxy, halogen, trifluoromethyl, (C$_1$-C$_8$)alkylcarbonyl, (C$_1$-C$_8$)alkylaminocarbonyl, di($C_1$-$C_8$)alkylaminocarbonyl, arylcarbonyl, heteroarylcarbonyl, aryl($C_1$-$C_8$)alkyl, heteroaryl($C_1$-$C_8$)alkyl, aryl($C_1$-$C_8$)alkyloxy, heteroaryl($C_1$-$C_8$) alkyloxy, aryl($C_1$-$C_8$)alkylcarbonyl, heteroaryl($C_1$-$C_8$)alkylcarbonyl, aryl($C_1$-$C_8$)alkyloxycarbonyl, heteroaryl($C_1$-$C_8$) alkyloxycarbonyl, ($C_1$-$C_8$)alkyloxycarbonyl, ($C_1$-$C_8$) alkylsulfonyl, arylsulfonyl, heteroarylsulfonyl, sulfamoyl, sulfonylamino, ($C_1$-$C_8$)alkylaminosulfonyl, di($C_1$-$C_8$)alkylaminosulfonyl, arylsulfonylamino, heteroarylsulfonylamino and ($C_1$-$C_8$)alkylsulfonylamino; wherein each alkyl, alkenyl, alkynyl or cycloalkyl may be unsubstituted or substituted with one or more residues selected from among hydroxyl, ($C_1$-$C_5$)alkyloxy, ($C_1$-$C_3$)alkyloxy($C_1$-$C_3$)alkyloxy, halogen, and NR6R7; and wherein each aryl or heteroaryl can be unsubstituted or substituted with one or more residues selected from among hydroxyl, ($C_1$-$C_5$)alkyloxy, halogen, ($C_1$-$C_8$)alkyl, ($C_3$-$C_8$)cycloalkyl, carboxy, NR6R7, cyano, trifluormethyl and nitro;

R3 is selected from hydrogen, a group —(CH$_2$)$_m$CH$_2$—COOH, OH, NH, and ($C_1$-$C_5$)alkyl which is optionally substituted with one or more halogens, one or two hydroxyl groups or ($C_1$-$C_3$)alkoxy;

R4 is hydrogen or fluoro, and is preferably hydrogen;

R5 is selected from hydrogen, halogen, ($C_1$-$C_3$)alkyl, ($C_1$-$C_3$)alkyloxy, ($C_1$-$C_3$)alkylthio, ($C_2$-$C_4$)alkenyl, ($C_2$-$C_4$)alkynyl, and NR6R7;

R6 and R7 are independently selected from hydrogen, ($C_1$-$C_6$)alkyl, ($C_3$-$C_7$)cycloalkyl, phenyl, heteroaryl, phenyl($C_1$-$C_6$)alkyl, heteroaryl($C_1$-$C_6$)alkyl, ($C_1$-$C_6$)alkylsulfonyl, phenylsulfonyl, heteroarylsulfonyl, ($C_1$-$C_8$)alkylcarbonyl, ($C_1$-$C_8$)alkoxycarbonyl, aminocarbonyl, ($C_1$-$C_6$)alkylaminocarbonyl, phenylcarbonyl, and heteroarylcarbonyl; wherein each alkyl may be unsubstituted or substituted with one or more residues selected from among hydroxyl, ($C_1$-$C_3$)alkyloxy, phenyl, halo, carboxy, and NR8R9; and wherein R6 and R7 may form a 5- to 7-membered cycle; and wherein phenyl or heteroaryl can be unsubstituted or substituted with one or more residues selected from among hydroxyl, ($C_1$-$C_3$)alkyloxy, halogen, ($C_1$-$C_3$) alkyl, carboxy, NR8R9, cyano, trifluormethyl and nitro;

R8 and R9 are independently selected from among hydrogen and ($C_1$-$C_3$)alkyl;

n and m are independently 0, 1 or 2.

In one preferred aspect, R1 in formula I is not hydrogen.

In one aspect, R1 and R2 are independently selected from the group comprising hydrogen, halogen, hydroxyl, cyano, nitro, NR6R7, carboxy, ($C_1$-$C_5$)alkyl, ($C_1$-$C_5$)alkyloxy, ($C_1$-$C_5$)alkylthio, ($C_2$-$C_5$)alkenyl, ($C_2$-$C_5$)alkynyl, ($C_3$-$C_6$)cycloalkyl, ($C_3$-$C_6$)cycloalkyloxy, ($C_3$-$C_6$)cycloalkylamino, phenyl, $C_5$-$C_6$heteroaryl, phenyloxy $C_5$-$C_6$ heteroaryloxy, halogen, trifluoromethyl, ($C_1$-$C_5$)alkylcarbonyl, ($C_1$-$C_5$) alkylaminocarbonyl, di($C_1$-$C_5$)alkylaminocarbonyl, phenylcarbonyl, heteroarylcarbonyl, phenyl($C_1$-$C_3$)alkyl, heteroaryl($C_1$-$C_3$)alkyl, phenyl($C_1$-$C_3$)alkyloxy, heteroaryl($C_1$-$C_3$)alkyloxy, phenyl($C_1$-$C_3$)alkylcarbonyl, heteroaryl($C_1$-$C_3$) alkylcarbonyl, phenyl($C_1$-$C_3$)alkyloxycarbonyl, heteroaryl ($C_1$-$C_3$)alkyloxycarbonyl, ($C_1$-$C_5$)alkyloxycarbonyl, ($C_1$-$C_5$)alkylsulfonyl, phenylsulfonyl, heteroarylsulfonyl, sulfamoyl, sulfonylamino, ($C_1$-$C_5$)alkylaminosulfonyl, di($C_1$-$C_5$)alkylaminosulfonyl, phenylsulfonylamino, heteroarylsulfonylamino and ($C_1$-$C_5$)alkylsulfonylamino; wherein each alkyl, alkenyl, alkynyl or cycloalkyl may be unsubstituted or substituted with one or more residues selected from among hydroxyl, ($C_1$-$C_3$)alkyloxy, ($C_1$-$C_3$)alkyloxy($C_1$-$C_3$)alkyloxy, halogen, and NR6R7; and wherein each phenyl or heteroaryl can be unsubstituted or substituted with one or more residues selected from among hydroxyl, ($C_1$-$C_3$)alkyloxy, halogen, ($C_1$-$C_3$)alkyl, ($C_3$-$C_6$)cycloalkyl, carboxy, NR6R7, cyano, trifluormethyl and nitro, wherein R1 is not hydrogen.

In one preferred aspect, R5 is hydrogen, halogen, methyl or methoxy. In one aspect, R5 is fluoro or hydrogen, and particularly hydrogen.

In one aspect, R6 and R7 are independently selected from hydrogen, ($C_1$-$C_4$)alkyl, ($C_3$-$C_7$)cycloalkyl, phenyl, heteroaryl, phenyl($C_1$-$C_3$)alkyl, heteroaryl($C_1$-$C_3$)alkyl, ($C_1$-$C_3$)alkylsulfonyl, phenylsulfonyl, heteroarylsulfonyl, ($C_1$-$C_3$)alkylcarbonyl, ($C_1$-$C_3$)alkoxycarbonyl, aminocarbonyl, ($C_1$-$C_3$)alkylaminocarbonyl, phenylcarbonyl, and h($C_5$-$C_6$) eteroarylcarbonyl; wherein each alkyl may be unsubstituted or substituted with one or more residues selected from among hydroxyl, methoxy, phenyl, fluoro, chloro, bromo, carboxy, and NR8R9; and wherein R6 and R7 may form a 5- to 7-membered cycle; and wherein phenyl or heteroaryl can be unsubstituted or substituted with one or more residues selected from among hydroxyl, ($C_1$-$C_3$)alkyloxy, halogen, ($C_1$-$C_3$) alkyl, carboxy, NR8R9, cyano, trifluormethyl and nitro.

One aspect of the invention relates to compounds of formula I and salts thereof, and methods for their use as further defined herein, wherein R1 is selected from fluoro, chloro, bromo, iodo, ($C_1$-$C_3$)alkyl, ($C_1$-$C_3$)alkoxy, phenyl, phenyl ($C_1$-$C_3$)alkyl, phenyl($C_1$-$C_3$) alkoxy, phenylcarbonyl, ($C_5$-$C_6$)heteroaryl, ($C_5$-$C_6$)heteroaryl-carbonyl, ($C_5$-$C_6$)heteroaryl($C_1$-$C_3$)alkyl and ($C_5$-$C_6$)heteroaryl($C_1$-$C_3$)alkoxy, wherein the alkyl and alkoxy groups are optionally substituted with one or more halogens, ($C_1$-$C_3$)alkoxy, or hydroxyl, and wherein the phenyl and ($C_5$-$C_6$)heteroaryl groups can be substituted with one or more halogens, ($C_1$-$C_3$)alkoxy, ($C_1$-$C_3$)alkyl, NR6R7, or hydroxyl;

R2 is selected from hydrogen, fluoro, chloro, bromo, iodo, ($C_1$-$C_3$)alkyl, ($C_1$-$C_3$)alkoxy, and phenyl, wherein the alkyl and alkoxy groups are optionally substituted with one or more halogens, ($C_1$-$C_3$)alkoxy, or hydroxyl, and wherein the phenyl group can be substituted with one or more halogens, ($C_1$-$C_3$)alkoxy, ($C_1$-$C_3$)alkyl, or hydroxyl, R3 is selected from hydrogen and a group —(CH$_2$)$_m$CH$_2$—COOH;

R4 is hydrogen or fluoro, and is preferably hydrogen;

R5 is selected from hydrogen, halogen, methyl or methoxy, and preferably represents fluoro or hydrogen, and particularly hydrogen;

n and m are independently 0, 1 or 2.

One preferred aspect of the invention relates to compounds of formula I and salts thereof, and methods of their use as further defined herein, wherein R1 is selected from halogen, ($C_1$-$C_3$)alkyl, ($C_1$-$C_3$)alkoxy, phenyl and ($C_5$-$C_6$)heteroaryl, wherein the alkyl and alkoxy groups are optionally substituted with one or more halogens, and wherein the phenyl and ($C_5$-$C_6$)heteroaryl groups are optionally substituted with halogen, ($C_1$-$C_3$)alkyl or ($C_1$-$C_3$) alkoxy;

R2 is selected from hydrogen, halogen, ($C_1$-$C_3$)alkyl, ($C_1$-$C_3$) alkoxy, and phenyl, wherein the alkyl and alkoxy groups are optionally substituted with one or more halogens, and wherein the phenyl group is optionally substituted with halogen, methyl or methoxy;

R3 is selected from hydrogen and a group —(CH$_2$)$_m$CH$_2$—COOH;

R4 is selected from hydrogen and fluoro, preferably hydrogen,

R5 is selected from hydrogen and fluoro, preferably hydrogen;

n and m are independently 0, 1 or 2.

In one preferred aspect, in the compounds of formula I and their salts for use as defined herein, R1 is selected from the group consisting of methyl, $CF_3$, chloro, fluoro, bromo, iodo, phenyl and $(C_5-C_6)$heteroaryl, wherein the phenyl or heteroaryl group is optionally substituted with halogen, methyl or methoxy;
R2 is selected from the group consisting of hydrogen, methyl, $CF_3$, chloro, fluoro, bromo, iodo and phenyl;
R3 is hydrogen, carboxymethyl, or carboxyethyl;
R4 and R5 are both hydrogen; and
n is 1.

Preferred compounds of formula I and their salts are those wherein,

R1 is selected from the group consisting of methyl, methoxy, hydroxy, $CF_3$, chloro, fluoro, bromo, iodo, thienyl, furanyl, pyridyl, and phenyl which is optionally substituted with halogen, methyl or methoxy;
R2 is selected from the group consisting of hydrogen, methyl, methoxy, hydroxyl, $CF_3$, chloro, fluoro, bromo, iodo and phenyl;
R3 is hydrogen, carboxymethyl, or carboxyethyl;
R4 and R5 are independently fluoro or, preferably, hydrogen; and
n is 1.

Particularly preferred compounds for use in the methods of the present invention are 3-(2-carboxyethyl)-4,6-dichloro-1H-indole-2-carboxylic acid, 3-(2-carboxyethyl)-4,6-dichloro-(1-carboxyethyl)-indole-2-carboxylic acid, 3-(2-carboxyethyl)-4,6-dimethyl-1H-indole-2-carboxylic acid, 3-(2-carboxyethyl)-6-chloro-1H-indole-2-carboxylic acid, 3-(2-carboxyethyl)-4,6-difluoro-1H-indole-2-carboxylic acid, 3-(2-carboxyethyl)-4,6-dibromo-1H-indole-2-carboxylic acid, 3-(2-carboxyethyl)-6-bromo-1H-indole-2-carboxylic acid, 3-(2-carboxyethyl)-6-iodo-1H-indole-2-carboxylic acid, 3-(2-carboxyethyl)-4,6-diiodo-1H-indole-2-carboxylic acid, 3-(2-carboxyethyl)-4,6-diphenyl-1H-indole-2-carboxylic acid, 3-(2-carboxyethyl)-6-phenyl-1H-indole-2-carboxylic acid, 3-(2-carboxyethyl)-6,7-dichloro-1H-indole-2-carboxylic acid, 3-(2-carboxyethyl)-6-chloro-7-fluoro-1H-indole-2-carboxylic acid, 3-(2-carboxyethyl)-6-bromo-2-carboxy-7-fluoro-1H-indole-2-carboxylic acid, 3-(2-carboxyethyl)-4,6-dimethoxy-1H-indole-2-carboxylic acid, 3-(2-carboxyethyl)-6-phenoxy-1H-indole-2-carboxylic acid, 3-(2-carboxyethyl)-6-benzyl-2-carboxy-1H-indole-2-carboxylic acid, 3-(2-carboxyethyl)-4,6-dihydroxy-1H-indole-2-carboxylic acid, 3-(2-Carboxyethyl)-6-(4-fluorophenyl)-1H-indol-2-carboxylic acid, 3-(2-carboxyethyl)-6-furanyl-1H-indole-2-carboxylic acid, 3-(2-carboxyethyl)-6-thienyl-1H-indole-2-carboxylic acid, 3-(2-carboxyethyl)-7-fluoro-6-phenyl-1H-indole-2-carboxylic acid, 3-(2-carboxyethyl)-6-(4-fluorophenyl)-7-fluoro-1H-indol-2-carboxylic acid, 3-(2-carboxyethyl)-6-furanyl-7-fluoro-1H-indole-2-carboxylic acid, 3-(2-carboxyethyl)-6-thienyl-7-fluoro-1H-indole-2-carboxylic acid, and salts thereof.

One aspect relates to a novel compound selected from 3-(2-carboxyethyl)-4,6-dibromo-1H-indole-2-carboxylic acid, 3-(2-carboxyethyl)-4,6-dichloro-(1-carboxyethyl)-indole-2-carboxylic acid, 3-(2-carboxyethyl)-6-bromo-1H-indole-2-carboxylic acid, 3-(2-carboxyethyl)-6-iodo-1H-indole-2-carboxylic acid, 3-(2-carboxyethyl)-4,6-diiodo-1H-indole-2-carboxylic acid, 3-(2-carboxyethyl)-4,6-diphenyl-1H-indole-2-carboxylic acid, 3-(2-carboxyethyl)-6-phenyl-1H-indole-2-carboxylic acid, 3-(2-carboxyethyl)-6,7-dichloro-1H-indole-2-carboxylic acid, 3-(2-carboxyethyl)-6-chloro-7-fluoro-1H-indole-2-carboxylic acid, 3-(2-carboxyethyl)-6-bromo-2-carboxy-7-fluoro-1H-indole-2-carboxylic acid, 3-(2-carboxyethyl)-6-benzyl-2-carboxy-1H-indole-2-carboxylic acid, 3-(2-carboxyethyl)-4,6-dihydroxy-1H-indole-2-carboxylic acid, 3-(2-carboxyethyl)-6-(4-fluorophenyl)-1H-indol-2-carboxylic acid, 3-(2-carboxyethyl)-6-furanyl-1H-indole-2-carboxylic acid, 3-(2-carboxyethyl)-6-thienyl-1H-indole-2-carboxylic acid, 3-(2-carboxyethyl)-7-fluoro-6-phenyl-1H-indole-2-carboxylic acid, 3-(2-carboxyethyl)-6-(4-fluorophenyl)-7-fluoro-1H-indol-2-carboxylic acid, 3-(2-carboxyethyl)-6-furanyl-7-fluoro-1H-indole-2-carboxylic acid, 3-(2-carboxyethyl)-6-thienyl-7-fluoro-1H-indole-2-carboxylic acid, and salts thereof. Another aspect relates to methods of using said novel compounds in therapy.

In one aspect, the GPR agonists of the present invention can also be used in methods and assays to be used for the identification of other GPR 17 modulators, particularly of GPR 17 antagonists.

One aspect of the present invention relates to a method of identifying a compound that modulates GPR 17 activity, said method (hereafter with or without its various aspects disclosed herein also called "the screening method of the present invention") comprising the steps of
(a) contacting a test compound with GPR17, or a functional GPR17 fragment in the presence of a suitable amount of a GPR17 agonist of formula I

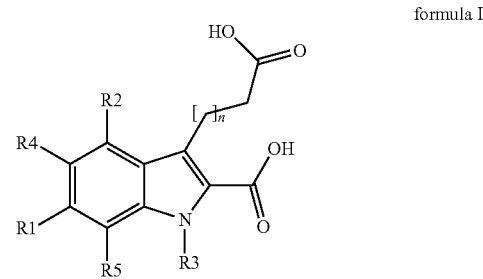

formula I or a salt thereof
(b) determining the biological activity of GPR17 or said functional GPR17 fragment after the addition of said test compound, and
(c) comparing the biological activity determined in step (b) with the activity of GPR17 or said functional GPR17 fragment in the presence of said GPR 17 agonist of formula I without the addition of said test compound, wherein in formula I R1 and R2 are independently selected from the group comprising hydrogen, halogen, hydroxy, formyl, oxime, cyano, nitro, amino, NR6R7, carboxy, carbamoyl, $(C_1-C_8)$alkyl, $(C_1-C_8)$alkyloxy, $(C_1-C_8)$alkylthio, $(C_2-C_8)$alkenyl, $(C_2-C_8)$alkynyl, $(C_3-C_8)$cycloalkyl, $(C_3-C_8)$cycloalkyloxy, $(C_3-C_8)$cycloalkylamino, aryl, heteroaryl, aryloxy, heteroaryloxy, halogen, trifluoromethyl, $(C_1-C_8)$alkylcarbonyl, $(C_1-C_8)$alkylaminocarbonyl, di$(C_1-C_8)$alkylaminocarbonyl, arylcarbonyl, heteroarylcarbonyl, aryl$(C_1-C_8)$alkyl, heteroaryl$(C_1-C_8)$alkyl, aryl$(C_1-C_8)$alkyloxy, heteroaryl$(C_1-C_8)$alkyloxy, aryl$(C_1-C_8)$alkylcarbonyl, heteroaryl$(C_1-C_8)$alkylcarbonyl, aryl$(C_1-C_8)$alkyloxycarbonyl, heteroaryl$(C_1-C_8)$alkyloxycarbonyl, $(C_1-C_8)$alkyloxycarbonyl, $(C_1-C_8)$alkylsulfonyl, arylsulfonyl, heteroarylsulfonyl, sulfamoyl, sulfonylamino, $(C_1-C_8)$alkylaminosulfonyl, di$(C_1-C_8)$alkylaminosulfonyl, arylsulfonylamino, heterosulfonylamino and alkylsulfonylamino; wherein each alkyl, alkenyl, alkynyl or cycloalkyl may be unsubstituted or substituted with one or more residues selected from among hydroxyl, $(C_1\text{-}C_8)$alkyloxy, $(C_1\text{-}C_3)$alkyloxy$(C_1\text{-}C_3)$alkyloxy, halogen, and NR6R7; and wherein each aryl or heteroaryl can be unsubstituted or substituted with one or more residues selected from among hydroxyl, $(C_1\text{-}C_5)$alkyloxy, halogen, $(C_1\text{-}C_5)$ alkyl, $(C_3\text{-}C_8)$cycloalkyl, carboxy, NR6R7, cyano, trifluormethyl and nitro;

R3 is selected from hydrogen, a group —$(CH_2)_m CH_2$—COOH, OH, NH, and $(C_1\text{-}C_5)$alkyl which is optionally substituted with one or more halogens, one or two hydroxyl groups or methoxy, R4 is selected from hydrogen and fluoro;

R5 is selected from hydrogen, halogen, $(C_1\text{-}C_3)$alkyl, $(C_1\text{-}C_3)$alkyloxy, $(C_1\text{-}C_3)$alkylthio, $(C_2\text{-}C_4)$alkenyl, $(C_2\text{-}C_4)$ alkynyl, and NR6R7;

R6 and R7 are independently selected from hydrogen, $(C_1\text{-}C_6)$alkyl, $(C_3\text{-}C_7)$cycloalkyl, phenyl, heteroaryl, phenyl $(C_1\text{-}C_6)$alkyl, heteroaryl$(C_1\text{-}C_6)$alkyl, $(C_1\text{-}C_6)$alkylsulfonyl, phenylsulfonyl, heteroarylsulfonyl, $(C_1\text{-}C_6)$ alkylcarbonyl, $(C_1\text{-}C_6)$alkoxycarbonyl, aminocarbonyl, $(C_1\text{-}C_6)$alkylaminocarbonyl, phenylcarbonyl, and heteroarylcarbonyl; wherein each alkyl may be unsubstituted or substituted with one or more residues selected from among hydroxyl, $(C_1\text{-}C_3)$alkyloxy, phenyl, halo, carboxy, and NR8R9; and wherein R6 and R7 may form a 5- to 7-membered cycle; and wherein phenyl or heteroaryl can be unsubstituted or substituted with one or more residues selected from among hydroxyl, $(C_1\text{-}C_3)$ alkyloxy, halogen, $(C_1\text{-}C_3)$alkyl, carboxy, NR8R9, cyano, trifluormethyl and nitro;

R8 and R9 are independently selected from hydrogen and $(C_1\text{-}C_3)$alkyl;

n and m are independently 0, 1 or 2.

Preferred compounds for use in the screening method of the present invention are disclosed further above and in the claims.

Another aspect of the present invention relates to a screening assay for the identification of GPR 17 modulators, preferably of GPR antagonists among a multitude of compounds, said screening assay (hereafter with or without its various aspects disclosed herein also called "assay of the present invention") comprising (a) cells or membrane fractions expressing GPR17 or a functional GPR17 fragment and (b) a suitable amount of a GPR17 agonist of formula I

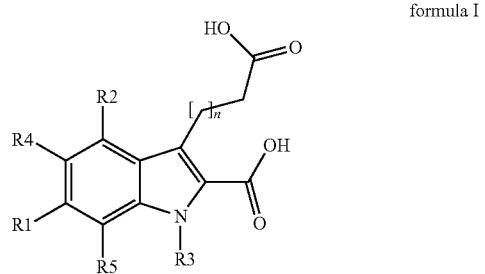

formula I or a salt thereof, wherein in formula I

R1 and R2 are independently selected from the group comprising hydrogen, halogen, hydroxy, formyl, oxime, cyano, nitro, amino, NR6R7, carboxy, carbamoyl, $(C_1\text{-}C_8)$alkyl, $(C_1\text{-}C_8)$alkyloxy, $(C_1\text{-}C_8)$alkylthio, $(C_2\text{-}C_8)$ alkenyl, $(C_2\text{-}C_8)$alkynyl, $(C_3\text{-}C_8)$cycloalkyl, $(C_3\text{-}C_8)$cycloalkyloxy, $(C_3\text{-}C_8)$cycloalkylamino, aryl, heteroaryl, aryloxy, heteroaryloxy, halogen, trifluoromethyl, $(C_1$-$C_8)$alkylcarbonyl, $(C_1\text{-}C_8)$alkylaminocarbonyl, di$(C_1\text{-}C_8)$alkylaminocarbonyl, arylcarbonyl, heteroarylcarbonyl, aryl$(C_1\text{-}C_8)$alkyl, heteroaryl$(C_1\text{-}C_8)$alkyl, aryl$(C_1\text{-}C_8)$alkyloxy, heteroaryl$(C_1\text{-}C_8)$alkyloxy, aryl$(C_1\text{-}C_8)$ alkylcarbonyl, heteroaryl$(C_1\text{-}C_8)$alkylcarbonyl, aryl $(C_1\text{-}C_8)$alkyloxycarbonyl, heteroaryl$(C_1\text{-}C_8)$ alkyloxycarbonyl, $(C_1\text{-}C_8)$alkyloxycarbonyl, $(C_1\text{-}C_8)$ alkylsulfonyl, arylsulfonyl, heteroarylsulfonyl, sulfamoyl, sulfonylamino, $(C_1\text{-}C_8)$alkylaminosulfonyl, di$(C_1\text{-}C_8)$alkylaminosulfonyl, arylsulfonylamino, heterosulfonylamino and alkylsulfonylamino; wherein each alkyl, alkenyl, alkynyl or cycloalkyl may be unsubstituted or substituted with one or more residues selected from among hydroxyl, $(C_1\text{-}C_5)$alkyloxy, $(C_1\text{-}C_3)$alkyloxy$(C_1\text{-}C_3)$alkyloxy, halogen, and NR6R7; and wherein each aryl or heteroaryl can be unsubstituted or substituted with one or more residues selected from among hydroxyl, $(C_1\text{-}C_5)$alkyloxy, halogen, $(C_1\text{-}C_5)$ alkyl, $(C_3\text{-}C_8)$cycloalkyl, carboxy, NR6R7, cyano, trifluormethyl and nitro;

R3 is selected from hydrogen, a group —$(CH_2)_m CH_2$—COOH, OH, NH, and $(C_1\text{-}C_5)$alkyl which is optionally substituted with one or more halogens, one or two hydroxyl groups or $(C_1\text{-}C_3)$alkoxy, R4 is selected from hydrogen and fluoro, and is preferably hydrogen;

R5 is selected from hydrogen, halogen, $(C_1\text{-}C_3)$alkyl, $(C_1\text{-}C_3)$alkyloxy, $(C_1\text{-}C_3)$alkylthio, $(C_2\text{-}C_4)$alkenyl, $(C_2\text{-}C_4)$ alkynyl, and NR6R7, R6 and R7 are independently selected from hydrogen, $(C_1\text{-}C_6)$alkyl, $(C_3\text{-}C_7)$cycloalkyl, phenyl, heteroaryl, phenyl $(C_1\text{-}C_6)$alkyl, heteroaryl$(C_1\text{-}C_6)$alkyl, $(C_1\text{-}C_6)$alkylsulfonyl, phenylsulfonyl, heteroarylsulfonyl, $(C_1\text{-}C_6)$ alkylcarbonyl, $(C_1\text{-}C_6)$alkoxycarbonyl, aminocarbonyl, $(C_1\text{-}C_6)$alkylaminocarbonyl, phenylcarbonyl, and heteroarylcarbonyl; wherein each alkyl may be unsubstituted or substituted with one or more residues selected from among hydroxyl, $(C_1\text{-}C_3)$alkyloxy, phenyl, halo, carboxy, and NR8R9; and wherein R6 and R7 may form a 5- to 7-membered cycle; and wherein phenyl or heteroaryl can be unsubstituted or substituted with one or more residues selected from among hydroxyl, $(C_1\text{-}C_3)$ alkyloxy, halogen, $(C_1\text{-}C_3)$alkyl, carboxy, NR8R9, cyano, trifluormethyl and nitro;

R8 and R9 are independently selected from among hydrogen and $(C_1\text{-}C_3)$alkyl;

n and m are independently 0, 1 or 2.

Preferred compounds for use in the assay of the present invention are disclosed further above and in the claims.

DEFINITIONS

The term "GPR 17" as used herein means a polypeptide showing GPR 17 activity, namely a G protein-coupled receptor having Uracil nucleotide/cysteinyl leukotriene receptor activity.

Preferably, the term "GPR17" as used herein includes but is not limited to the human short splicing variant of GPR 17 (SEQ ID NO 1), the human long splicing variant of GPR 17 (SEQ ID NO 2), the rat GPR 17 (SEQ ID NO 3), the mouse GPR 17 (SEQ ID NO 4), and any other natural occurring GPR 17.

Further, the term also refers to functional fragments, fractions or subsequences of the above discussed polypeptides.

Even more preferred, said polypeptide is at least one selected from the group consisting of
(a) a polypeptide having the amino acid sequence of SEQ ID NO 1 or SEQ ID NO 2,
(b) polypeptides comprising the amino acid sequence of SEQ ID NO 1 or SEQ ID NO 2,
(c) polypeptides having at least about 60%, preferably at least about 70%, more preferably at least about 75%, even more preferably at least 80%, at least about 85%, at least about 90%, at least about 95%, or even at least about 98% sequence identity to SEQ ID NO 1 or SEQ ID NO 2, wherein the sequence identity is preferably determined with one of the methods discussed below,
(d) functional fragments, fractions or subsequences of any of the sequences discussed in (a), (b) or (c), and/or
(e) fusion products which have been obtained after deletion of a fragment, fraction or subsequence from any of the sequences discussed in (a), (b), (c) or (d), and fusion of the remaining sequences.

The sequences set forth under (a)-(e) will also be called "query sequences" in the following.

A "functional fragment, fraction or subsequence" comprises a polypeptide which represents a part of the amino acid sequence of GPR17 as further defined herein, wherein said functional GPR 17 fragment still shows GPR17 activity. One example of a functional GPR 17 fragment can be a truncated GPR 17, wherein a certain number of amino acids is missing at the N' and/or C' terminus of GPR17. Another example of a functional GPR 17 fragment is one of various subsequent parts of a "splitted" GPR 17 receptor, wherein said GPR17 parts are contained on individual expression plasmids and are physiologically inactive when expressed alone, but assemble to a functional GPR 17 receptor in an appropriate environment upon co-transfection of cells. Methods for the expression of "split receptors" are disclosed e.g. in Maggio R et al, FEBS Lett. 1993 Mar. 15; 319(1-2):195-200, and Schoneberg T et al, J Biol. Chem. 1995 Jul. 28; 270(30):18000-6.

The term "% sequence identity" as used herein refers to the identity of one sequence (e.g., sequence A) to another sequence (e.g., sequence B) over the whole length of either of the sequences, i.e., to the percentage of residues that are identical in the two sequences to be compared. In general, the two sequences are aligned to give a maximum correlation between the sequences. If applicable, this may include inserting "gaps" in either one or both sequences, to enhance the degree of alignment.

Further, sequence alignment generally falls into two categories: global alignments and local alignments. Calculating a global alignment is a form of global optimization that "forces" the alignment to span the entire length of all query sequences. By contrast, local alignments identify regions of similarity within long sequences that are often widely divergent overall. In the present invention, either type of alignment can be performed when "% sequence identity" is determined.

Readily available computer programs can be used to aid in the analysis, such as ALIGN, Dayhoff, M. O. in Atlas of Protein Sequence and Structure M. O. Dayhoff ed.,* 5 Suppl. 3:353-358, National biomedical Research Foundation, Washington, D.C., The preferred way to determine "% sequence identity" between two sequences is to count the exact number of matches between two sequences aligned as discussed above, dividing by the length of the shorter sequence, and multiplying the result by 100. This approach is a merely arithmetical approach which does not provide any kind of biological weighing.

Another approach to determine the "% sequence identity" of two sequences which is likewise preferred is the GenePAST™ algorithm provided by GenomeQuest, Inc. This algorithm was formerly called "Kerr", and is discussed, e.g., in Dufresne et al, Nature Biotechnology 20, 1269-1271 (2002), or Andree et al, World Patent Information, 2008, vol. 30, issue 4, pages 300-308. Again, this approach carries out a merely arithmetical determination of "% sequence identity" without any biological weighing.

In an exemplary case where (i) the query sequence has 339 residues (like SEQ ID No 1, which defines one possible GPR 17 polypeptide according to the invention), (ii) the subject sequence has 400 residues, and (iii) an alignment of 200 residues was found between both sequences with 4 mismatches comprised in the alignment (which means that a functional fragment of query sequences aligns with the subject sequence), the following approaches can be used to determine the "% sequence identity" in accordance with the present invention:

1. In a preferred embodiment, the "% sequence identity" is calculated over the length of the entire query sequence (e.g. 339 residues). In this case, 143 mismatches have to be considered, which leads to a % sequence identity of (339-143)/339=57.8%
2. In another preferred embodiment which is used when a fragment of the query sequence is to be compared with a given subject sequence, the "% sequence identity" is calculated over the alignment length of e.g. 200 residues (e.g., the functional fragment of the query sequence which aligns with the subject sequence serves as a basis for sequence identity calculation). In this case, both sequences share a % sequence identity of (200−4)/200=98%
3. In yet another embodiment, the "% sequence identity" can be calculated over the length of the entire subject sequence (400 residues), 204 mismatches have to be considered, which leads to a % sequence identity of (400−204)/400=49%. This option, which takes the subject sequence as a basis for sequence identity calculation, is however less preferred.

An alternative method often used to determine the "% sequence identity" between two polypeptide sequences, and which shall also be considered as an alternative means to determine % sequence identity according to the present invention, uses the BLAST algorithm (Tatusova and Madden, FEMS Microbiol Lett 174, 1999, 247; Altschul, et al, J. Mol. Biol. 215:403-410 (1990)), which is available e.g. through the National Center for Biotechnology Information (NCBI; "blastp"), National Library of Medicine, National Institutes of Health, Building 38A, 8600 Rockville Pike, Bethesda, Md. 30 20894, USA (Wheeler et al., Nucleic Acid Res 35, 2007, D5; Pearson, Methods Enzymol 183, 1990, 63).

However, The BLAST algorithm performs alignment scoring adjustments based on considerations of biological relevance between query and subject sequences. This involves the risk of mismatches between mere arithmetic sequence comparison, as preferred under the above mentioned "% sequence identity" language, and biologically weighted sequence comparison, as performed, e.g., by BLAST. However, as the BLAST algorithm is frequently used, finds wide acceptance and is publicly available, it can as well be used in the context of the present invention to determine "% sequence identity".

Other algorithms which can also be used to determine "% sequence identity" within the meaning of the present invention comprise, but are not restricted to Smith & Waterman (Smith and Waterman, Journal of Molecular Biology 147: 195-197 and BLW (also known as "Fragment Search")).

In a preferred embodiment, the "polypeptide showing GPR 17 activity" shows at least about 20%, more preferably at least about 30%, more preferably at least about 40%, at least about 50%, at least about 60%, at least about 70%, and even more preferably at least about 80% or at least about 90% of the activity of the human GPR 17 receptor having the amino acid sequence of SEQ No1.

The term "identifying a compound that modulates GPR 17 activity" includes determining the GPR17 activity (either wanted or unwanted) of a particular compound, as well as the screening of a multitude of compounds for the identification of GPR 17 antagonists showing a certain threshold of GPR 17 activity, and may also include the confirmatory testing of already known or suggested GPR17 functional activities of a given compound. The term "identifying a compound that modulates GPR 17 activity" also includes the determination or comparison of a test compound's functional activity towards GPR17 in a particular experimental setting, such as e.g. in a particular cell line, in a new experimental setup, or in cells or tissues from a particular disease state.

The term "screening assay" or "screening method" as used herein refers to an assay or method which can be used and/or adapted to determine and/or analyze the GPR17 modulating properties of a single compound and/or of a variety or large number of compounds, such as e.g. in a high throughput screening format.

"Alkyl" includes monovalent saturated aliphatic hydrocarbyl groups. The hydrocarbon chain may be either straight-chained or branched. "Alkyl" has preferably 1-8 carbon atoms ("$(C_1-C_8)$alkyl") or 1-6 carbon atoms ("$(C_1-C_6)$ alkyl"), and in some instances even more preferably 1-5 carbon atoms ("$(C_1-C_5)$alkyl"), 1-4 carbon atoms ("$(C_1-C_4)$ alkyl"), or only 1-3 carbon atoms ("$(C_1-C_3)$alkyl"). This term is exemplified by groups such as methyl, ethyl, n-propyl, isopropyl, n-butyl, iso-butyl, tert-butyl, t-amyl, and the like.

"Alkylsulfonyl" includes a radical-$S(O)_2R$, wherein R is an alkyl group as defined herein. Representative examples include, but are not limited to, methanesulfonyl, ethylsulfonyl, propylsulfonyl, butylsulfonyl and the like.

"Alkylthio" includes a radical-S—R wherein R is an alkyl group as defined herein that may be optionally substituted as defined herein. Representative examples include, but are not limited to, methylthio, ethylthio, propylthio, butylthio, and the like.

"Alkylaminosulfonyl" includes the group —$SO_2$—NH-Alkyl, wherein "alkyl" is preferably selected from the groups specified in the definition of "alkyl" further above. Examples of "alkylaminosulfonyl" are e.g. methylaminosulfonyl, ethylaminosulfonyl or butylaminosulfonyl.

"Dialkylaminosulfonyl" includes the group —$SO_2$—N-dialkyl, wherein each "alkyl" is preferably and independently selected from the groups specified in the definition of "alkyl" further above. Examples of "alkylaminosulfonyl" are e.g. N,N-dimethylaminosulfonyl, N,N-methylethylaminosulfonyl or N,N-methylbutylaminosulfonyl.

"Alkylsulfonylamino" includes the group —NH—$SO_2$-Alkyl, wherein alkyl is preferably selected from the groups specified in the definition of "alkyl" further above. Most preferably "alkyl" in "alkylsulfonylamino" is a $C_1-C_8$-alkyl group, such as e.g. methanesulfonylamino.

"Alkylcarbonyl" includes the group —C(O)-alkyl, wherein alkyl is preferably selected from the groups specified in the definition of "alkyl" further above. "Alkylcarbonyl" is particularly preferably —C(O)—$C_1-C_6$-Alkyl, and most preferably acetyl, propionyl oder butyryl.

"Alkylaminocarbonyl" includes the groups —C(O)—NH-alkyl wherein "alkyl" is preferably selected from the groups specified in the definition of "alkyl" further above.

"Alkylaminocarbonyl" is particularly preferably —C(O)—NH—$(C_1-C_6)$Alkyl

"Dialkylaminocarbonyl" includes the group —CO—N-dialkyl, wherein each "alkyl" is preferably and independently selected from the groups specified in the definition of "alkyl" further above.

"Dialkylaminocarbonyl" is particularly preferably —C(O)—N-di$(C_1-C_6)$alkyl

"Alkyloxy" or "alkoxy" includes the group —OR wherein R is "alkyl" as defined further above. Particular alkyloxy groups include, by way of example, methoxy, ethoxy, n-propoxy, isopropoxy, n-butoxy, tert-butoxy, sec-butoxy, n-pentoxy, 1,2-dimethylbutoxy, and the like.

"Alkyloxyalkyloxy" refers to the group —OROR', wherein R and R' are the same or different "alkyl" groups as defined further above.

"Alkyloxycarbonyl" refer to the radical —C(=O)—O—R, wherein R is an alkyl group as defined herein.

"Alkenyl" includes monovalent olefinically unsaturated hydrocarbyl groups being straight-chained or branched and having at least 1 double bond. "Alkenyl" has preferably 2-8 carbon atoms ("$C_2-C_8$ alkenyl") morr preferably 2-6 carbon atoms ("$(C_2-C_6)$alkenyl"), and in some instances even more preferably 2-5 carbon atoms ("$(C_2-C_5)$alkenyl"), 2-4 carbon atoms ("$(C_2-C_4)$alkenyl"), or only 2-3 carbon atoms ("$(C_2-C_3)$alkenyl"). Particular alkenyl groups include ethenyl (—CH=CH2), n-propenyl (—CH2CH=CH2), isopropenyl (C(CH3)=CH2), and the like.

"Alkynyl" includes unsaturated hydrocarbyl groups being straight-chained or branched and having at least 1 triple bond. "Alkynyl" has preferably 2-8 carbon atoms ("$(C_2-C_8)$alkynyl") more preferably 2-6 carbon atoms ("$(C_2-C_6)$alkynyl"), and in some instances even more preferably 2-5 carbon atoms ("$(C_1-C_5)$alkynyl"), 2-4 carbon atoms ("$(C_2-C_4)$alkynyl"), or only 2-3 carbon atoms ("$(C_2-C_3)$alkynyl"). A preferred alkynyl group is ethynyl (acetylenyl).

"Amino" refers to the radical-$NH_2$.

"Aryl" refers to an aromatic hydrocarbyl radical. Examples of "aryl" radicals are phenyl, naphthyl, indenyl, azulenyl, fluorine or anthracene, wherein phenyl is preferred. "Arylalkyl" comprises the group -alkyl-aryl, wherein "aryl" and "alkyl" have the meaning as defined further above. Examples of arylalkyl groups are phenylpropyl, phenylethyl and benzyl, wherein benzyl is a particularly preferred arylalkyl group.

"Arylalkyloxy" comprises the group —O-alkyl-aryl, wherein "aryl" and "alkyl" have the meaning as defined further above, and wherein aryl is preferably phenyl. Examples of arylalkyloxy groups are pehnylethyloxy and benzyloxy.

"Aryloxy" comprises the group-O-aryl, wherein "aryl" has the meaning as defined further above, and wherein aryl is preferably phenyl "Arylcarbonyl" is —C(O)-aryl, wherein "aryl" has the meaning as defined further above, and wherein aryl is preferably phenyl "Arylalkylcarbonyl" is —C(O)-alkyl-aryl, wherein "aryl" and "alkyl" have the meaning as defined further above, and wherein aryl is preferably phenyl "Arylalkyloxycarbonyl" is the group —C(O)—O-alkyl-aryl, wherein "aryl" and "alkyl" have the meaning as defined further above, and wherein aryl is preferably phenyl "Arylsulfonyl" is —$SO_2$-aryl, wherein aryl" has the meaning as defined further above, and wherein aryl is preferably phenyl "Arylsulfonylamino" refers to the group —NH—SO$_2$-aryl, wherein "aryl" has the meaning as defined further above, and wherein aryl is preferably phenyl "Carbamoyl" refers to the group —C(=O)NH$_2$ "Carboxy" refers to the radical —C(=O)OH.

"Cycloalkyl" refers to cyclic saturated aliphatic hydrocarbyl groups. The numbers of C-atoms referenced in connection with a given cycloalkyl group corresponds to the number of ring forming carbon atoms, e.g. "(C$_3$-C$_6$)cycloalkyl" refers to a cycloalkyl with between three and six ring-forming C atoms. Examples of "cycloalkyl" are (C$_3$-C$_5$)cycloalkyls, (C$_3$-C$_7$)cycloalkyls, or more specifically (C$_3$-C$_6$)cycloalkyls such as e.g. cyclopropyl, cyclobutyl, cyclopentyl, cyclohexyl etc. If a "cycloalkyl" carries more than one substituent, e.g. one or more alkyl substituent these substituents may be attached to the same or to different ring-forming carbon atoms.

"Cycloalkyloxy" refers to the group —OR, wherein R is "cycloalkyl" group as defined further above.

"Cycloalkylamino" refers to the group —NHR, wherein R is "cycloalkyl" group as defined further above.

"Cyano" refers to the radical —C≡N.

"Formyl" refers to the group —C(=O)H

"Halo" or "halogen" refers to fluoro, chloro, bromo and iodo.

"Heteroaryl" refers to aromatic ring system containing at least one heteroatom such as O, S or N. Examples of heteroaryl radicals are furanyl, thienyl, pyrollyl, thiazolyl, oxazolyl, imidazolyl, pyrazolyl, isoxazolyl, isothiazolyl, triazolyl, oxadiazolyl, thiadiazolyl, pyranyl, pyridinyl, pyridazinyl, pyrimidinyl, pyrazinyl, triazinyl, tetrazinyl, indolinyl, indolyl, isoindolyl, benzofuranyl, benzothiophenyl, benzoimidazolyl, benzthiazolyl, purinyl, quinazolinyl, quinolinyl, isoquinolinyl, quinolizinyl, pteridinyl, carbazolyl, wherein one-ring systems, in particular one ring-systems with 5 to 6 ring atoms ("C$_5$-C$_6$ heteroaryl") such as e.g. pyridinyl, thienyl, oxazolyl, triazolyl, pyrimidinyl, imidazolyl, and the like are preferred.

"Heteroarylalkyl" comprises the group -alkyl-heteroaryl, wherein "heteroaryl" and "alkyl" have the meaning as defined further above. Examples of heteroarylalkyl groups are heteroarylethyl and benzyl, wherein benzyl is a particularly preferred heteroarylalkyl group.

"Heteroarylalkyloxy" comprises the group —O-alkyl-heteroaryl, wherein "heteroaryl" and "alkyl" have the meaning as defined further above. Examples of heteroarylalkyloxy groups are heteroarylethyloxy and benzyloxy.

"Heteroaryloxy" comprises the group-O-heteroaryl, wherein heteroaryl" has the meaning as defined further above "Heteroarylcarbonyl" is —C(O)-heteroaryl, wherein heteroaryl" has the meaning as defined further above "Heteroarylalkylcarbonyl" is —C(O)-alkyl-heteroaryl, wherein "heteroaryl" and "alkyl" have the meaning as defined further above "Heteroarylalkyloxycarbonyl" is the group —C(0)-O-alkyl-heteroaryl, wherein "heteroaryl" and "alkyl" have the meaning as defined further above "Heteroarylsulfonyl" is —SO$_2$-heteroaryl, wherein heteroaryl" has the meaning as defined further above "Heteroarylsulfonylamino" refers to the group —NH—SO$_2$-heteroaryl, wherein "heteroaryl" has the meaning as defined further above "Heteroarylcarbonyl" refers to the group —CO-heteroaryl.

"Hydroxy" refers to the radical —OH.

"Nitro" refers to the radical-NO$_2$.

"Oxime" refers to the group —CH=N—OH.

"Phenyl" is the aromatic radical —C$_6$H$_5$. Whether a phenyl group is substituted with one or more substituents, is specified throughout this specification and the claims.

"Phenylalkyl" comprises the group -alkyl-phenyl, wherein "phenyl" and "alkyl" have the meaning as defined further above. Examples of phenylalkyl groups are phenylethyl and benzyl, wherein benzyl is a particularly preferred phenylalkyl group.

"Phenylalkyloxy" comprises the group —O-alkyl-phenyl, wherein "phenyl" and "alkyl" have the meaning as defined further above. Examples of phenylalkyloxy groups are phenylethyloxy and benzyloxy.

"Phenoxy" comprises the group-O-phenyl, wherein phenyl" has the meaning as defined further above "Phenylcarbonyl" is —C(O)-phenyl, wherein phenyl" has the meaning as defined further above "Phenylalkylcarbonyl" is —C(O)-alkyl-phenyl, wherein "phenyl" and "alkyl" have the meaning as defined further above "Phenylalkyloxycarbonyl" is the group —C(O)—O-alkyl-phenyl, wherein "phenyl" and "alkyl" have the meaning as defined further above "Phenylsulfonyl" is —SO$_2$-phenyl, wherein phenyl" has the meaning as defined further above "Phenylsulfonylamino" refers to the group —NH—SO$_2$-phenyl, wherein "phenyl" has the meaning as defined further above "Sulfamoyl" includes the group —SO$_2$—NH$_2$.

"Sulfonylamino" includes the group —NH—SO$_2$H.

"Trifluormethyl" refers to the group —CF$_3$.

The term "GPR17 antagonists" as used herein includes compounds which decrease the GPR17 activity to 70% or less, 60% or less, 50% or less, preferably 40% or less, more preferably 30% or less, or even 20% or less at the highest applied concentration compared to the GPR17 activity after activation by RA 11-150; the term "GPR17 antagonist" includes full antagonists, partial agonists, and inverse agonists, which may be competitive or non-competitive in nature.

A preferred aspect of the invention relates to the method or assay as hereinbefore described, wherein in formula I R1 is selected from the group consisting of methyl, CF$_3$, chloro, fluoro, bromo, iodo, phenyl and (C$_5$-C$_6$)heteroaryl, wherein the phenyl or heteroaryl group is optionally substituted with halogen, methyl or methoxy;

R2 is selected from the group consisting of hydrogen, methyl, CF$_3$, chloro, fluoro, bromo, iodo and phenyl;

R3 is hydrogen, carboxymethyl, or carboxyethyl;

R4 and R5 are both hydrogen; and n is 1.

In a particular preferred aspect, the GPR 17 agonist used in the screening method and/or the assay of the present invention is selected from the group comprising 3-(2-carboxyethyl)-4,6-dichloro-1H-indole-2-carboxylic acid, 3-(2-carboxyethyl)-4,6-dichloro-(1-carboxyethyl)-indole-2-carboxylic acid, 3-(2-carboxyethyl)-4,6-dimethyl-1H-indole-2-carboxylic acid, 3-(2-carboxyethyl)-6-chloro-1H-indole-2-carboxylic acid, 3-(2-carboxyethyl)-4,6-difluoro-1H-indole-2-carboxylic acid, 3-(2-carboxyethyl)-4,6-dibromo-1H-indole-2-carboxylic acid, 3-(2-carboxyethyl)-6-bromo-1H-indole-2-carboxylic acid, 3-(2-carboxyethyl)-6-iodo-1H-indole-2-carboxylic acid, 3-(2-carboxyethyl)-4,6-diiodo-1H-indole-2-carboxylic acid, 3-(2-carboxyethyl)-4,6-diphenyl-1H-indole-2-carboxylic acid, 3-(2-carboxyethyl)-6-phenyl-1H-indole-2-carboxylic acid, 3-(2-carboxyethyl)-6,7-dichloro-1H-indole-2-carboxylic acid, 3-(2-carboxyethyl)-6-chloro-7-fluoro-1H-indole-2-carboxylic acid, 3-(2-carboxyethyl)-6-Bromo-2-carboxy-7-fluoro- 1H-indole-2-carboxylic acid, 3-(2-carboxyethyl)-4,6-dimethoxy-1H-indole-2-carboxylic acid, 3-(2-carboxyethyl)-6-phenoxyl H-indole-2-carboxylic acid, 3-(2-carboxyethyl)-6-Benzyl-2-carboxy-1H-indole-2-carboxylic acid, 3-(2-carboxyethyl)-4,6-dihydroxy-1H-indole-2-carboxylic acid, 3-(2-Carboxyethyl)-6-(4-fluorophenyl)-1H-indol-2-carboxylic acid, 3-(2-carboxyethyl)-6-furanyl-1H-indole-2-carboxylic acid, 3-(2-carboxyethyl)-6-thienyl-1H-indole-2-carboxylic acid, 3-(2-carboxyethyl)-7-fluoro-6-phenyl-1H-indole-2-carboxylic acid, 3-(2-carboxyethyl)-6-(4-fluorophenyl)-7-fluoro-1H-indol-2-carboxylic acid, 3-(2-carboxyethyl)-6-furanyl-7-fluoro-1H-indole-2-carboxylic acid, 3-(2-carboxyethyl)-6-thienyl-7-fluoro-1H-indole-2-carboxylic acid, and salts thereof.

In one preferred aspect, the biological activity of GPR17 is determined in the method and assays of the present invention by measuring the increase of $^{35}SGTP_\gamma S$ binding to the heterotrimeric G proteins activated by the receptor, the inhibition of cAMP formation and/or the release of calcium from intracellular calcium stores, the increase in inositolphosphates (IP), and/or the recruitment of cytoplasmic R-arrestin proteins, as well as the other methods described herein.

In one aspect, the GPR17 activity is determined in the methods and assays of the present invention by using (a) a transfected cell line, which is preferably selected from transfected CHO cells, astrocytoma cells, COS7 cells or HEK293 cells, or membrane fractions thereof, or (b) native tissue, cells (and membrane fractions thereof), expressing GPR17 to an extent sufficient to achieve functional activation. Examples of naturally GPR17 expressing cells are oligodendrocytic precursor cells which can be gained from newborn animals (P1, P2) as primary cell cultures. Hence, the term "contacting a test compound with GPR 17" or similar phrases used herein include the addition of test compounds or putative GPR17 antagonists to cell systems or cell fragments (over)expressing GPR17.

A variety of methods, means and signals can be used as "read outs systems" in the screening method of the present invention, and are all encompassed by the method of the present invention. Such read out systems will be used to determine the activity of GPR17 or functional fragments thereof after its activation by the agonists of the invention and the response to test compounds, preferably the response to antagonists.

Accordingly, in one aspect the method and/or screening assay (e.g. in form of a kit) of the present invention further comprise means for determining the GPR17 activity ("read out system"). Said means for determining the GPR17 activity are preferentially selected from one or more of
 (a) means for determining the release of calcium from intracellular calcium stores associated with GPR17 activation, preferably a cell membrane permeable indicator, which binds to calcium released in the cell thereby providing a measurable signal, preferably fluorescence or luminescence,
 (b) means for determining GTP$_\gamma$S binding to heterotrimeric G proteins thereby proving a measurable signal, preferably $^{35}SGTP_\gamma S$, the radioactivity of which will be incorporated into heterotrimeric G proteins,
 (c) means for determining the inhibition of cAMP formation or its elevation associated with GPR17 activation, preferably a stimulator of the adenylyl cyclase (e.g. forskolin) and a suitable cAMP indicator system,
 (d) means for determining the increase in inositolphosphates (IP), quantified as IP1, e.g. a suitable IP1 detector system
 (e) means for determining the recruitment of cytoplasmic β-arrestin proteins, preferably detection of β-arrestin translocation to the receptor using fluorescence or bioluminescence resonance energy transfer.

In one preferred aspect of the present invention, the read out system used in the method and/or screening assay of the present invention is based on the measurement of cAMP formation as (inverse) indicator of GPR17 activity and includes forskolin as stimulator of the adenylyl cyclase, and a competitive immunoassay as cAMP indicator system, which preferably provides a fluorescence signal. Such an indicator system is described in more detail in Example 3 herein.

One preferred aspect of the present invention relates to the method or screening assay of the present invention used for identifying antagonists of GPR17.

One preferred aspect of the present invention relates to a method of identifying a GPR17 antagonist.

One preferred aspect of the present invention relates to a method of manufacturing a GPR17 modulator, preferably a GPR17 antagonist comprising the step of determining the compound's ability to modulate the biological activity of GPR17 by subjecting said compound to the method and/or assay of the present invention. For example, a library of new compounds may be selected and screened for the compounds' ability to modify the GPR 17 response by applying the method and/or assay of the present invention.

Hence, one aspect of the present invention relates to a method of manufacturing a GPR 17 modulator, comprising the steps of
 (a) identifying a compound that modulates GPR17 activity by the method described herein, and
 (b) manufacturing a compound identified as GPR17 modulator.

One aspect of the present invention relates to a method of manufacturing a GPR17 antagonist comprising the following subsequent steps:
 (1) selecting at least one compound which acts as a GPR 17 antagonist when tested in the method and/or the assay of the present invention,
 (2) selecting one or more analogs of the GPR 17 antagonist(s) selected in step (1),
 (3) subjecting the one or more GPR 17 antagonist analogs of step (2) to the method and/or assay of the present invention thereby determining the GPR 17 antagonistic properties of said GPR 17 antagonist analogs,
 (4) optionally repeating steps (1) to (3) one or more times by producing further chemical analogs of the GPR 17 antagonist(s) thereby identifying GPR17 antagonists with improved GPR17 antagonistic properties,
 (5) selecting a compound for synthesis, and
 (6) synthesizing or having synthesized the compound selected in step (5).

One preferred aspect of the present invention relates to a method of identifying a GPR17 antagonist useful for the treatment, alleviation or prevention of multiple sclerosis comprising the screening method of the present invention and/or comprising a step of using the screening assay of the present invention.

One aspect of the invention is a method of treating, alleviating or preventing a GPR17 mediated disease, such as spinal cord injury, multiple sclerosis, cerebral, cardiac and renal ischemia, and preferably multiple sclerosis or an ischemic brain insult such as stroke in a patient in need thereof comprising the steps of
 (a) identifying a GPR17 antagonist using the screening method and/or the assay of the present invention, (b) administering said identified GPR17 antagonist in a therapeutically effective concentration, optionally together with one or more pharmaceutically acceptable excipients, to said patient in need thereof.

One aspect of the present disclosure relates to a GPR17 antagonist, which has been identified using the screening method or assay of the present invention, and the use of such GPR17 antagonist in therapy, particularly in the treatment, alleviation or prevention of a GPR17 mediated disease, such as spinal cord injury, multiple sclerosis, cerebral, cardiac and renal ischemia, preferably of multiple sclerosis or stroke.

One aspect of the present invention relates to the use of the GPR17 agonist of the present invention in a screening assay and/or in a method which is suitable to identify GPR17 modulators, preferably GPR17 antagonists. In one aspect said GPR17 agonists may be used to screen for GPR 17 antagonists among a multitude of test compounds for which the GPR17 affinity and/or functional activity at GPR17 are basically unknown. In one aspect of the present invention, said GPR17 agonists may be used to determine (including confirming) the GPR 17 affinity or functional activity towards GPR17 of a single compound or a selected group of compounds.

The present invention is further illustrated by the non-limiting examples below.

EXPERIMENTAL SECTION

Examples

Example (1)

hGPR17 Expressing Cell Systems and Media

The sequence for the human GPR17 (short isoform) was subcloned into the vector pLXSN (Clontech Laboratories, CA 94043, USA), which can be used for retroviral transfection of the human astrocytoma cell line 1321N1. Since it was postulated by Clana et. al. that GPR17 is activated by uracil nucleotides such as UDP, UDP-glucose and UDP-galactose, 1321N1 astrocytoma cells were chosen as an appropriate test system, because it was known that this cell line does not express endogenous nucleotide receptors. For the retroviral transfection of 1321N1 astrocytoma cells the packaging cell line GP+envAM12 was cultivated in HXM medium (50 ml of foetal calf serum (FCS), 5 ml of penicillin G/streptomycin solution (final concentration 100 U/ml penicillin, 100 µg/ml streptomycin), 1% ultra glutamine, 0.75 ml of hypoxanthine (10 mg/ml), 12.5 ml of xanthine (10 mg/ml), 1.25 ml of mycophenolic acid (10 mg/ml) and 2 ml of hygromycin B (50 mg/ml) were added to 500 ml DMEM). One day before transfection $1.5 \times 10^6$ cells were seeded and incubated overnight at 37° C., 5% $CO_2$ and 95% humidity in a 25 $cm^2$ cell culture flask containing medium without antibiotics. For at least two hours before transfection the medium was exchanged for 6.25 ml DMEM medium without any additive. Two solutions were prepared for the transfection. The first solution consisted of 25 µl of Lipofectamine™ 2000 (final concentration 2%) and 600 µl of DMEM medium without any additives while the second solution was composed of 6.25 µg of pLXSN-GPR17 and 3.75 µg of pLXSN-VSV-G vector DNA. The second solution was filled up with DMEM medium without any additives. Solution one was incubated for 5 min at room temperature before both solutions were combined and incubated for 20 min, also at room temperature. Afterwards the sample was added to the packaging cell line and incubated for 12-15 h. The medium was then replaced with 3 ml of fresh medium containing 30 µl of a 500 mM sodium butyrate solution. The virus production was stimulated by sodium butyrate and took place by incubation for 48 h at 32° C. and 95% humidity. One day before infection 500,000 of 1321N1 astrocytoma cells were seeded in a 25 $cm^2$ cell culture flask. After 48 h of virus production, the retroviruses were harvested and sterilised by filtration through a filter with a pore size of 45 µm. The host cell medium was replaced with the sterilized virus supernatant containing 6 µl of polybrene solution (4 mg/ml) and the infection of the host cells took place for further 48 h of incubation at 37° C., 95% humidity and 5% $CO_2$. After incubation, the transfected cells were transferred to a 175 $cm^2$ cell culture flask and selected by adding medium containing G418. The efficiency of infection and stable transfection using this method was up to 95%.

In order to investigate potential differences in receptor signalling as a function of the cellular background, GPR17 was additionally expressed and analysed in a further cell system. Therefore, a recombinant Chinese hamster ovary (CHO) cell line stably expressing GPR17 was generated using the Flp-In™ T-Rex™ expression system. Here, expression of GPR17 was induced after adding doxycycline.

Medium for Retrovirally Transfected 1321N1 Astrocytoma Cells

G418 (800 µg/ml G418) was added to DMEM medium with 10% FCS for preparation of medium to cultivate 1321N1 astrocytoma cells stably expressing GPR17.

Medium for Flp-In T-rex-CHO (FLIPR) Cells (=CHO-GPR17 Cells)

DMEM/F-12 medium with 10% FCS, 30 µg/ml of blasticidin and 500 µg/ml of hygromycin B was used for culturing stable CHO cells generated by using the Flp-In T-rex system. Doxycycline was added up to a concentration of 1 µg/ml for the induction of receptor expression in this cell line.

Example (2)

Measurement of Ligand Activity by Calcium Mobilization Assay

PLC activation and $IP_3$ accumulation result in a release of calcium from intracellular calcium stores, for example the endoplasmic reticulum. In order to detect the released calcium, cells are loaded with a cell membrane permeable dye, which is converted within the cell into its active form by the cleavage of ester bonds. The active form of the dye binds the released calcium. The fluorescence properties of the dye change after calcium binds to the dye. These changes can be detected automatically and represent the ligand-dependent receptor activation. Cells from two confluently grown (80 to 90%) 175 $cm^2$ cell culture flasks were needed for a calcium assay using the NOVOstar microplate reader (approximately 150,000 cells per well). Cells were harvested after removing the medium, washed once with PBS buffer and detached using a trypsin/EDTA solution. After incubation for 45 min at 37° C. and 5% $CO_2$, the cells were pelleted by centrifugation (5 min, 200 g). Cells were resuspended in 994 µl of Krebs HEPES buffer (KHB; 118.6 mM NaCl, 4.7 mM KCl, 1.2 mM $KH_2PO_4$, 4.2 mM $NaHCO_3$, 11.7 mM D-glucose, 10 mM HEPES (free acid), 1.3 mM $MgSO_4$ and 1.2 mM $CaCl_2$, pH 7.4) and loaded in the absence of light with fluorescent, namely Oregon Green 488 BAPTA-1/AM dye, by incubating them for one hour at 28° C. and 700 rpm in an Eppendorf Thermomixer in the presence of Pluronic F-127. Pluronic F-127 was supplemented so that the cells could better absorb the dye. The cells were washed twice with 1 ml of KHB buffer (three centrifugation steps, each for 15 sec at 2700 rpm) before being seeded in a 96-well microplate in a total volume of 180 µl. A 10-fold concentrated agonist solution (35 µl) was added to another 96-well microplate with a V-profile. Both plates were placed into the NOVOstar microplate reader and incubated there for 20 min. After incubation, the required gain was determined by the microplate so that the fluorescence background of the cells was between 38,000 and 42,000 fluorescence units. This background is an optimal range for starting the measurement, because it is in the middle of the reader's detection range. Normally, the background in each well of a microplate should be the same. The background was determined by performing a so-called validation. A validation is performed to detect irregularities in cell densities between different wells, fluorescence or absorption properties as well as unspecific antagonist effects. These irregularities are noticeable when the background is significantly increased or decreased compared to the normal range. Afterwards, 20 µl of agonist were injected from the source plate to the measurement plate by the injector unit of the NOVOstar, and the increase in fluorescence was determined as a function of the calcium efflux resulting from receptor stimulation.

Example (3)

Inhibition of Forskolin-Stimulated Intracellular cAMP Accumulation by Ligand

Two signal transduction pathways that influence the activity of the adenylyl cyclase in oppositional ways can be activated upon receptor activation. Whereas the Gs pathway stimulates the adenylyl cyclase-dependent catalysation of cAMP formation, the Gi pathway inhibits it. The detection of cAMP accumulation is based on the HTRF® technology described above. In this case a monoclonal antibody specific to cAMP was the donor fluorophore while the acceptor fluorophore d2 was fused to cAMP. The analysis of the Gi pathway was based on the direct activation of the adenylyl cyclase, for example, by forskolin. Upon activation, the Gi pathway inhibits the forskolin-dependent activation of the adenylyl cyclase, leading to decreased cAMP accumulation. The inhibition of forskolin-stimulated cAMP accumulation in 1321N1 or CHO cells was performed using the HTRF® cAMP dynamic kit (Cisbio Bioassays, BP 84175, France). Cells were resuspended in assay buffer with 1 mM 3-isobutyl-1-methylxanthine (IBMX) supplemented and dispensed in 384-well microplates at a density of 50,000 cells/well in a volume of 5 µl. After preincubation in assay buffer for 30 min, the cells were stimulated by adding 5 µl of agonist in the respective concentration of forskolin. The final concentration of forskolin was dependent on the cell line which was employed in the assay. Adenylyl cyclase was stimulated with 1 µM forskolin in 1321N1-GPR17 cells and with 10 µM forskolin in CHO-GPR17 cells, followed by incubation for 30 min at room temperature. The reaction was terminated by lysis of the cells, which results from the addition of 5 µl of d2-conjugate followed by the addition of 5 µl of anti-IP1-cryptate (both supplements are diluted in conjugate and lysis buffer). The assay was incubated for 60 min at room temperature and time-resolved FRET signals were measured at an excitation wavelength of 320 nm using the Mithras LB 940 multimode reader (Berthold technologies, D-75323 Bad Wildbad). The evaluation of HTRFR data was performed following the instructions of the kit manufacturer. Data analysis was based on the fluorescence ratio emitted by labeled cAMP (665 nm) over the light emitted by the europium cryptate-labelled anti-cAMP (620 nm). Levels of cAMP were normalized to the amount of cAMP elevated by 10 µM or 1 µM forskolin alone.

Example (4)

Description of $^{35}$SGTP$_\gamma$S Binding Assay

[$^{35}$S]GTPγS binding experiments were carried out in 96-well plates using 5 µg of protein/well. Membranes were added to 400 µl of incubation buffer (10 mM HEPES, 10 mM MgCl$_2$, 100 mM NaCl, pH 7.4) containing 10 µM GDP and RA-II-150 in the indicated concentrations. Reactions were started by adding 50 µl of 0.07 nM [$^{35}$S]GTPγS and then incubated for 60 min at 30° C. Membrane-bound radioactivity was separated by vacuum filtration. After drying; glass fiber filter mats were melted with scintillation wax, and radioactivity was measured by liquid scintillation counting.

Example 5

β-Arrestin Assay

Arrestin recruitment was detected in BRET$^2$ assays using HEK293 cells stably expressing human GPR17-Rluc and GFP2-β-arrestin2.

Cells were detached by trypsinization, counted and washed once in assay buffer (HBSS, 20 mM HEPES (S12), pH 7.0). After centrifugation at 800 rpm for 4 min, the pelleted cells were resuspended in an appropriate volume of assay buffer to a density of 1×10$^6$ cells per ml. In order to stabilize readings, cells were allowed to incubate at 28° C. for 30 min while slowly shaking (180 rpm), prior to experiments.

The coelenterazine 400A stock solution was freshly diluted (3:100) in PBS containing 20% of ethanol to obtain a 30 µM solution, which was always kept in the dark, due to its light-sensitivity.

As a first step, the agonist solutions were prepared and 10 µl of each 8-fold dilution was dispensed in the 384-well assay plate. DMSO concentrations were adjusted and did not exceed 0.1% in final concentrations.

Harvested and stabilized cells were manually distributed (70 µl, 70.000 c/well) to the assay plate containing the agonist dilutions. Cells were stimulated at 28° C. at 450 rpm for 5 min. Following cell stimulation, Coelenterazine 400A (C10, 10 µl) was injected by the Mithras injector 3 at a final concentration of 3.3 µM. Two seconds after the injections, the light output from the well was measured at 400 and 515 nm by use of Mithras LB 940 plate reader, which allows the sequential integration of light signals detected with two filter settings. The BRET signal, milliBRET ratio, was calculated by the quotient of the fluorescence emitted by GFP2-β-arrestin2 (515 nm) over the light emitted by the GPR17-Rluc (400 nm).

Example 6

Inositolphosphate IP1 Assay

Agonist induced IP1 accumulation was determined using the HTRF kit (Cisbio, France) according to manufacturer's instructions. On the day of experiment the required amount of cells were harvested and washed twice in HBSS (20 mM HEPES), including two centrifugation steps for 15 s at 2700 rpm. Pelleted cells were resuspended in appropriate volume of stimulation buffer (containing LiCl) and dispensed at 100.000 cells/7 µl/well in 384-well microtiter plates. Following incubation at 37° C. for 30 min, cells were stimulated by addition of 7 µl 2-fold concentrated agonists diluted in stimulation buffer. If the impact of antagonists was investigated, they were added 30 min prior to agonist addition and incubated at 37° C. After another 30 min incubation at 37° C., the reaction was terminated by addition of 3 μl of IP-d2 followed by 3 μl of europium(Eu)-cryptate-labeled IP1 Mab diluted (1:20) in lysis buffer. The plates were allowed to incubate for 60 min at room temperature and were then read by Mithras LB940 (Berthold) with 100 μs delay and 200 μs window time.

Example 7

GPR17 Antagonist Screening Assay to Identify GPR17 Antagonists

Figure 6:
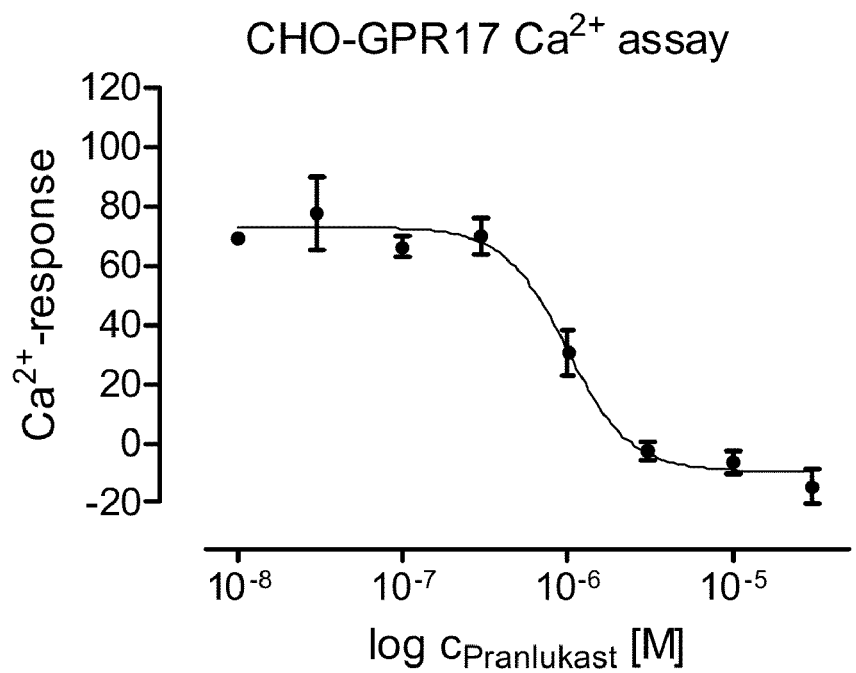

GPR17-expressing cells were pre-incubated with the test compounds for a defined period of time (for example 5-30 minutes, longer and shorter incubations are possible) followed by addition of agonist at a fixed concentration, for example its $EC_{80}$, which is the concentration of agonist producing 80% of its maximal response. Under these conditions, inhibitors of GPR17 function display concentration-dependent inhibition of the agonist signals as exemplified in FIG. 6 with a GPR17 inhibitor.

Example 8

Synthesis of GPR 17 Agonists

A. General Procedure for the Japp-Klingemann Reaction to form Indole Diethyl Esters.

Aniline (1 eq) was dissolved in concentrated HCl (3 eq) diluted with water (~2 mL/mmol of aniline), and cooled to 0° C. Sodium nitrite (2.5 M, 1 eq) in water was added dropwise such that the temperature remained below 5° C. Sodium acetate (4.5 M, 5.5 eq) in water was added to the solution followed by ethyl 2-oxocyclopentanecarboxylate (1 eq). The reaction was stirred at 0° C. for 15 min and then allowed to warm to room temperature over a period of 1 hour. The aqueous solution was extracted with chloroform (~100 mL/mmol of aniline). The organic layer was dried over sodium sulphate, filtered and evaporated under reduced pressure. To the dark oily mixture was added a solution of sodium carbonate (~0.7 M aq., 1.1 eq) and stirred under reflux for 10 min. The mixture was allowed to cool to room temperature and carefully acidified with 6 N HCl. The precipitate was extracted with chloroform, dried over sodium sulphate, filtered and evaporated under reduced pressure. The residue was the dissolved in ethanol (1 mL/mmol of aniline) containing concentrated sulphuric acid (~0.1 mL) and refluxed overnight. The reaction was cooled to room temperature and the solvent concentrated under vacuum. The crude sample was purified by column chromatography using ethyl acetate/hexane 1/4. The desired compound was recrystallized from hot hexane.

B. General Procedure for the Alkylation of the Indole Diester Analogues.

A Mixture of indole diester (1 eq), potassium carbonate (1 eq) and alkylating agent (3 eq) in the appropriate solvent was refluxed overnight. The solvent was evaporated under reduced pressure and the mixture extracted with a mixture of ethyl acetate/saturated $NaHCO_3$ solution. The organic layer was dried over sodium sulphate, filtered and concentrated under vacuum. The resulting crude sample was purified by column chromatography.

C. General Procedure for the Saponification of Indole Diethyl Esters.

The diester was dissolved in THF (10 mL/mmol of indole diethyl ester) and diluted with an equal volume of water and then treated with $LiOH.H_2O$ (10 eq). The reaction mixture was stirred at room temperature overnight, diluted with water, acidified, and extracted with ethyl acetate. The organic layer was dried over sodium sulphate, filtered and concentrated under reduced pressure. The product was recrystallized from hot ethyl acetate/hexane.

D. Synthesis of Example Compounds (a) 3-(2-Carboxyethyl)-4,6-dichloro-1H-indole-2-carboxylic acid

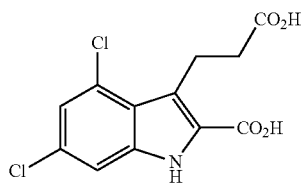 [SMILES: O=C(O)CCc1c(C(=O)O)[nH]c2cc(Cl)cc(Cl)c12]

Reference, Incorporated Herein by Reference in its Entirety: Salituro, Francesco G.; Harrison, Boyd L.; Baron, Bruce M.; Nyce, Philip L.; Stewart, Kenneth T.; Kehne, John H.; White, H. Steven; McDonald, Ian A. 3-(2-Carboxy-1H-indole-2-carboxylic acid-based antagonists of the NMDA (N-methyl-D-aspartic acid) receptor associated glycine binding site. Journal of Medicinal Chemistry (1992), 35, 1791-9.

(b) 3-(2-Carboxyethyl)-4,6-dichloro-(1-carboxyethyl)-indole-2-carboxylic acid (i) 4,6-Dichloro-1,3-bis-(2-ethoxycarbonylethyl)-1H-indole-2-carboxylic acid ethyl ester

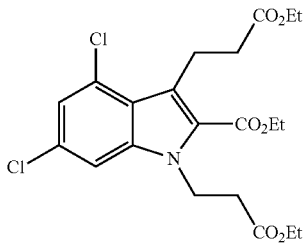 [SMILES: CCOC(=O)CCc1c(C(=O)OCC)n(CCC(=O)OCC)c2cc(Cl)cc(Cl)c12]

The desired compound was obtained using ethyl 3-bromopropionate as alkylating agent and acetonitrile as reaction solvent, and recrystallized from hot methanol (yield 77%). $^1$H NMR (500 MHz, $CDCl_3$) δ 1.2 (t, J=7.25 Hz, 3H), 1.23 (t, J=7.25 Hz, 3H), 1.41 (t, J=7.25 Hz, 3H), 2.64 (m, 2H), 2.77 (t, J=7.25 Hz, 2H), 3.59 (m, 2H), 4.09 (q, J=7.25 Hz, 2H), 4.12 (q, J=7.25 Hz, 2H), 4.41 (q, J=7.25 Hz, 2H), 4.67 (t, J=7.25 Hz, 2H), 7.1 (d, J=1.55 Hz, 1H), 7.31 (d, J=1.6 Hz, 1H) ppm.

(ii) 1,3-Bis-(2-carboxyethyl)-4,6-dichloro-1H-indole-2-carboxylic acid

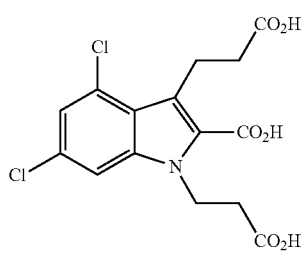 [SMILES: O=C(O)CCc1c(C(=O)O)n(CCC(=O)O)c2cc(Cl)cc(Cl)c12]

(Yield 50%); mp 229° C.; $^1$H NMR (500 MHz, DMSO-$d_6$) δ 2.49 (m, 2H), 2.65 (t, J=7.25 Hz, 2H), 3.44 (t, J=8.1 Hz, 2H), 4.65 (t, J=7.25 Hz, 2H), 7.2 (d, J=1.6 Hz, 1H), 7.76 (d, J=1.55, 1H), 12.69 (br, 3H) ppm; $^{13}C$ NMR (500 MHz, DMSO-$d_6$) 20.63, 34.74, 36.31, 110.47, 121.18, 127.19, 128.75, 129.03, 138.64, 162.92, 172.35, 173.66. EIMS (m/z, %) 374.0 ($M^+$, 100).

(c) 3-(2-Carboxyethyl)-4,6-dimethyl-1H-indole-2-carboxylic acid

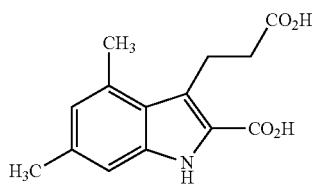 [SMILES: Cc1cc(C)c2c(CCC(=O)O)c(C(=O)O)[nH]c2c1]

Reference Incorporated Herein by Reference in its Entirety:

Takahashi, Kenji; Kasai, Masayasu; Ohta, Masaru; Shoji, Yoshimichi; Kunishiro, Kazuyoshi; Kanda, Mamoru; Kurahashi, Kazuyoshi; Shirahase, Hiroaki Novel Indoline-Based Acyl-CoA:Cholesterol Acyltransferase Inhibitor with Antiperoxidative Activity: Improvement of Physicochemical Properties and Biological Activities by Introduction of Carboxylic Acid. Journal of Medicinal Chemistry (2008), 51, 4823-4833.

(d) 3-(2-Carboxyethyl)-6-chloro-1H-indole-2-carboxylic acid

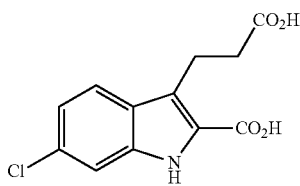 [SMILES: O=C(O)CCc1c(C(=O)O)[nH]c2cc(Cl)ccc12]

Reference

Salituro, Francesco G.; Harrison, Boyd L.; Baron, Bruce M.; Nyce, Philip L.; Stewart, Kenneth T.; Kehne, John H.; White, H. Steven; McDonald, Ian A. 3-(2-Carboxy-1H-indole-2-carboxylic acid-based antagonists of the NMDA (N-methyl-D-aspartic acid) receptor associated glycine binding site. Journal of Medicinal Chemistry (1992), 35, 1791-9.

(e) 3-(2-Carboxyethyl)-4,6-difluoro-1H-indole-2-carboxylic acid

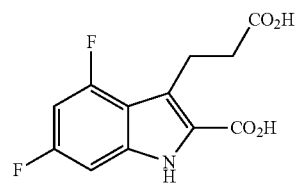 [SMILES: O=C(O)CCc1c(C(=O)O)[nH]c2cc(F)cc(F)c12]

Reference

Salituro, Francesco G.; Harrison, Boyd L.; Baron, Bruce M.; Nyce, Philip L.; Stewart, Kenneth T.; Kehne, John H.; White, H. Steven; McDonald, Ian A. 3-(2-Carboxy-1H-indole-2-carboxylic acid-based antagonists of the NMDA (N-methyl-D-aspartic acid) receptor associated glycine binding site. Journal of Medicinal Chemistry (1992), 35, 1791-9.

(f) 3-(2-Carboxyethyl)-4,6-dibromo-1H-indole-2-carboxylic acid (i) 3,5-Dibromobenzenediazonium salt (Mixture I)

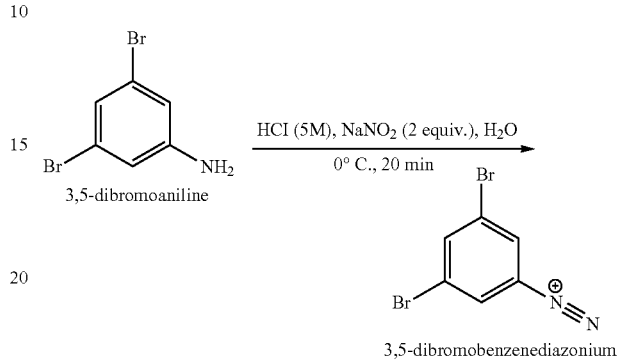

To a well stirred suspension of 3,5-dibromoaniline (2.51 g, 10 mmol) in 16.6 ml HCl (5 M) at 0° C. was dropwise added a solution of sodium nitrite 1.38 g (20 mmol, 2 equiv) in 8 ml water, previously cooled to 0° C. The addition of sodium nitrite solution was slow, in order to keep the temperature of the mixture below 8° C. The resulting orange-red mixture was stirred at 0° C. for further 20 min.

(ii) 2-(Ethoxycarbonyl)cyclopentanone (mixture II)

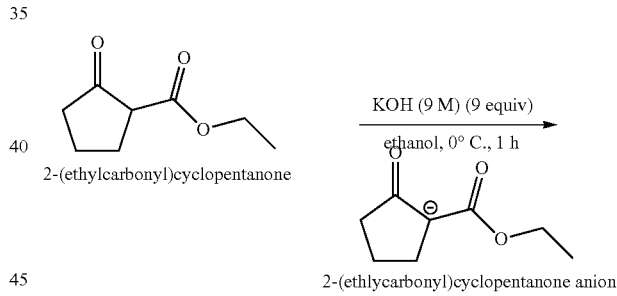

2-(Ethoxycarbonyl)cyclopentanone (2.512 ml, 1.344 g, 15 mmol) was dissolved in ethanol (4.2 ml) and cooled to 0° C. Then, a potassium hydroxide solution (5.040 g, 90 mmol, 6 equiv.) in water (5 ml) previously cooled to 0° C. was added dropwise within ca. 30 min in order to keep the temperature below 8° C. The mixture turned to a white-milky color, and the final mixture was stirred at 0° C. for further 30 min.

(iii) (E/Z)-5-(2-(3,5-Dibromophenyl)hydrazinyl)-6-ethoxy-6-oxohex-4-enoic acid

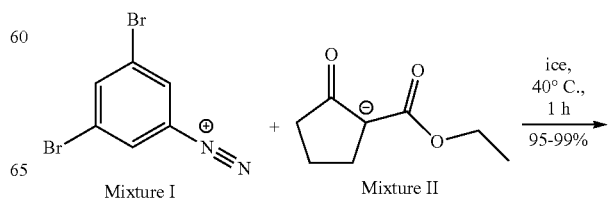

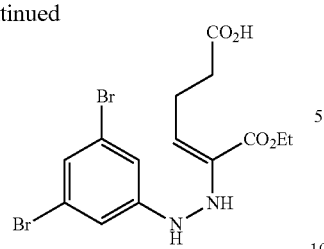

Ice (50 g) was added to mixture II with stirring at 0° C., followed by the addition of mixture I, and stirring continued for 1 h at 40° C. The combined mixtures were then let to cool to rt and the pH was subsequently adjusted to 4-5 by adding 1 M HCl. The desired product was extracted with diethyl ether (3×50 ml). The organic layer was collected, dried over magnesium sulfate, filtered, and the filtrate was evaporated to dryness yielding gummy material (95-99%). This material was used without further purification for the next step.

(iv) (E/Z)-Diethyl 2-(2-(3,5-dibromophenyl)hydrazinyl)hex-2-enedioate

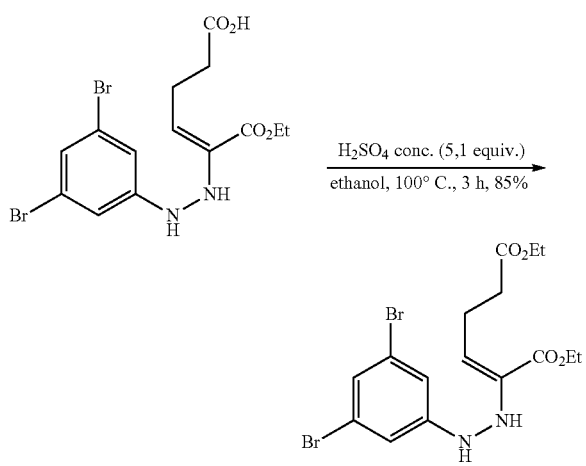

(E/Z)-5-(2-(3,5-Dibromophenyl)hydrazinyl)-6-ethoxy-6-oxohex-4-enoic acid (4.361 g, 10 mmol) was dissolved in absolute ethanol (100 ml) followed by the addition of conc. sulfuric acid (2.7 ml, 50.5 mmol, 5.1 equiv.). The mixture was then allowed to reflux for 1 h at 100° C. Then the ethanol was evaporated and the residue was treated with 100 ml of ice-water. The aqueous solution was extracted with dichloromethane (3×50 ml); the organic layer was dried over magnesium sulfate, filtered and concentrated. The residue was purified by silica gel column chromatography using 20% of ethyl acetate in cyclohexane yielding a white solid in 85% yield.

(v) Ethyl 4,6-dibromo-3-(3-ethoxy-3-oxopropyl)-1H-indole-2-carboxylate

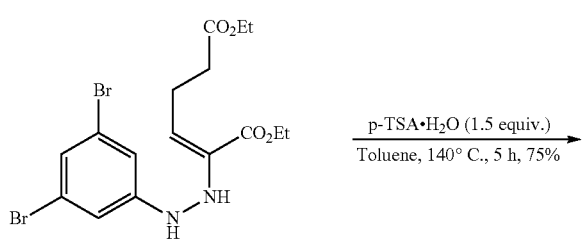

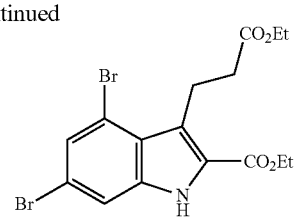

A mixture of p-toluenesulfonic acid (2.954 g, 15 mmol, 1.5 equiv.) and 100 ml of dry toluene was refluxed for 1 h at 140° C.; water was continuously removed by means of a Dean-Stark trap. Subsequently, 4.64 g (10 mmol) of the starting material ((E/Z)-diethyl 2-(2-(3,5-dibromophenyl)hydrazinyl)hex-2-enedioate) dissolved in a minimum amount of dry toluene (ca. 15 ml) was added and the mixture was refluxed for 5 h. Then it was allowed to cool down to rt, and toluene was removed under reduced pressure and the residue was dissolved in dichloromethane and washed with water. The organic layer was dried over magnesium sulfate, filtered, and evaporated to dryness. The residue was purified by silica gel column chromatography using 20% of ethyl acetate/cyclohexane as eluent to yield a light-beige-colored solid in 75%. $^1$H-NMR (DMSO-$d_6$): δ 1.15, 1.34 (each t, 3H, $^3J$=7.1 Hz, CH$_3$); 2.55 (t, 2H, $^4J$=8.2 Hz, 2'-H); 3.54 (t, 2H, $^4J$=8.2 Hz, 1'-H); 4.05, 4.35 (each q, 2H, J=7.1 Hz, CH$_2$); 7.42 (d, 1H, $^4J$=1 Hz, 5-H); 7.60 (d, 1H, $^4J$=1 Hz, 7-H); 12.06 (s, 1H, NH). $^{13}$C-NMR (DMSO-$d_6$): δ 14.17, 14.20 (2CH$_3$, each C=OOCH$_2$CH$_3$); 19.9 (C-2'); 36.0 (C-1'); 59.9, 60.9 (2CH$_2$, each C=OOCH$_2$CH$_3$); 114.9 (C-7); 115.5 (C-4); 117.1 (C-6); 121.6 (C-3); 123.5 (C-2); 125.7 (C-3a); 126.4 (C-5); 138.0 (C-7a); 161.1 (2'-CO$_2$Et); 171.9 (2-CO$_2$Et). LC-MS (m/z): 465 [M+NH$_4^+$]$^+$, 448 [M]$^+$, 446 [M]$^-$. Purity (LC-MS): 98%.

(vi) 3-(2-Carboxyethyl)-4,6-dibromo-1H-indole-2-carboxylic acid

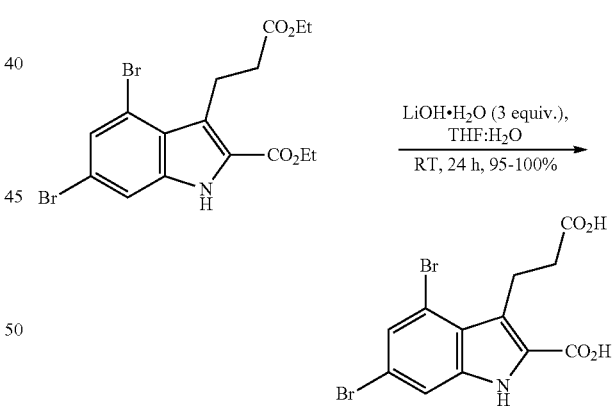

Ethyl 4,6-dibromo-3-(3-ethoxy-3-oxopropyl)-1H-indole-2-carboxylate (4.47 g, 10 mmol) was dissolved in 25 ml tetrahydrofurane (THF) with stirring at rt. Then a solution of 1.26 g of lithium hydroxide trihydrate (3 equiv.) in 25 ml water was added and the resulting mixture was let to stir at rt for 24 h. After completion of the reaction THF was removed under reduced pressure and the pH was adjusted to 4-5, and the product was extracted with diethyl ether (3×30 ml). The organic layers were dried over magnesium sulfate, filtered, and evaporated to dryness to yield a light-beige-colored solid in 95-100% yield. mp. 259° C.; well soluble in methanol, ethanol and ethyl acetate; slightly soluble in petrol ether, water, hexane. $^1$H-NMR (MeOH-$d_4$): δ 2.67 (t, 2H, $^3J$=8.4

Hz, CH$_2$); 3.71 (t, 2H, $^3$J=8.4 Hz, CH$_2$); 7.42 (d, 1H, $^4$J=1.6 Hz, C7-H); 7.62 (d, 1H, $^4$J=1.6 Hz, C5-H). $^{13}$C-NMR (MeOH-d$_4$): δ 21.4 (C-2'); 37.9 (C-1'); 115.9 (C-7); 117.0 (C-4); 118.8 (C-6); 123.9 (C-3); 125.5 (C-2); 127.9 (C-3a); 128.2 (C-5); 139.6 (C-7a); 164.6 (2'-CO$_2$H); 170.1 (2-CO$_2$H). LC-MS (m/z): 392.0 [M]$^+$; 390.0 [M]$^-$. Purity (LC-MS): 99%.

(g) 3-(2-Carboxyethyl)-6-bromo-1H-indole-2-carboxylic acid (i) 3-Bromobenzenediazonium salt (mixture I)

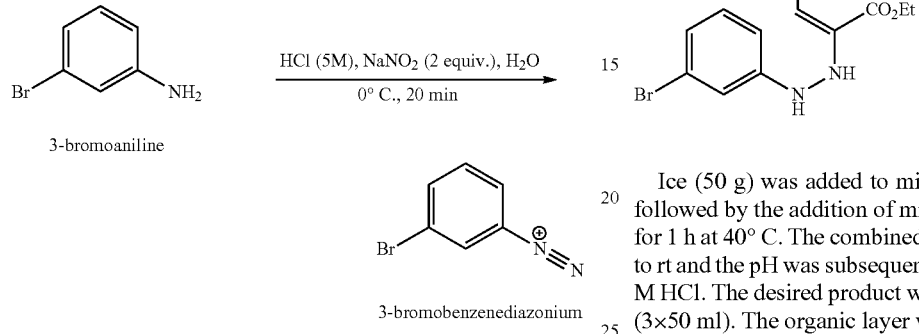

To a well stirred suspension of 3-bromoaniline (1.72 g, 10 mmol) in 16.6 ml HCl (5 M) at 0° C. was dropwise added a solution of sodium nitrite 1.38 g (20 mmol, 2 equiv) in 8 ml water, previously cooled to 0° C. The addition of sodium nitrite solution was slow, in order to keep the temperature of the mixture below 8° C. The resulting orange-red mixture was stirred at 0° C. for further 20 min.

(ii) 2-(Ethoxycarbonyl)cyclopentanone (mixture II)

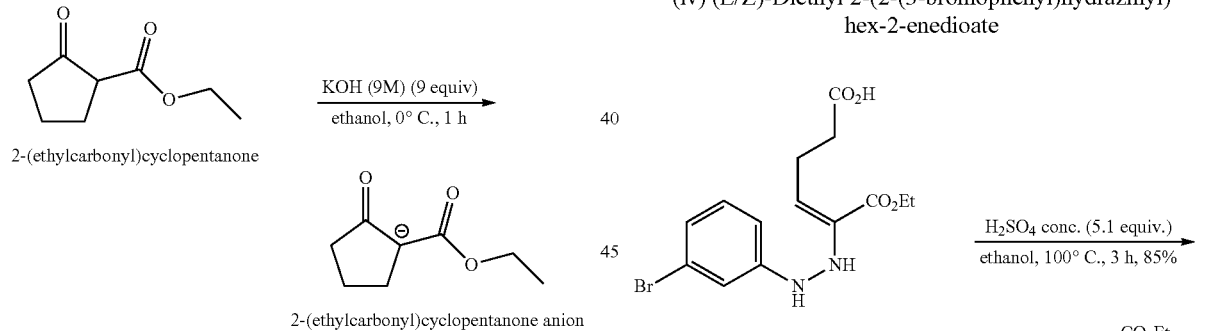

2-(Ethoxycarbonyl)cyclopentanone (2.51 ml, 1.34 g, 15 mmol) was dissolved in ethanol (4.2 ml) and cooled to 0° C. Then, a potassium hydroxide solution (5.04 g, 90 mmol, 9 equiv.) in water (5 ml) previously cooled to 0° C. was added dropwise within ca. 30 min in order to keep the temperature below 8° C. The mixture turned milky-white, and the final mixture was stirred at 0° C. for further 30 min.

(iii) (E/Z)-5-(2-(3-Bromophenyl)hydrazinyl)-6-ethoxy-6-oxohex-4-enoic acid

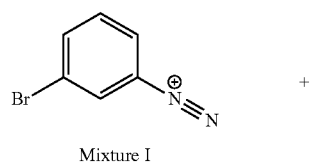 +

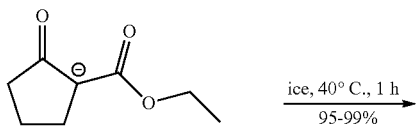

Ice (50 g) was added to mixture II with stirring at 0° C., followed by the addition of mixture I, and stirring continued for 1 h at 40° C. The combined mixtures were then let to cool to rt and the pH was subsequently adjusted to 4-5 by adding 1 M HCl. The desired product was extracted with diethyl ether (3×50 ml). The organic layer was collected, dried over magnesium sulfate, filtered, and the filtrate was evaporated to dryness yielding gummy material (95-99%). This material was used without further purification for the next step.

(iv) (E/Z)-Diethyl 2-(2-(3-bromophenyl)hydrazinyl)hex-2-enedioate

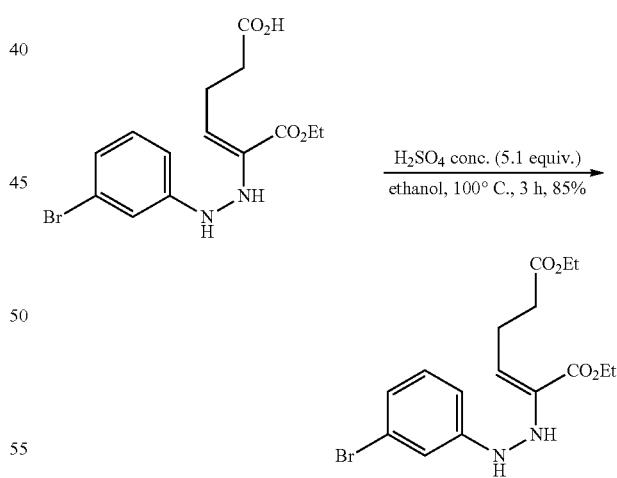

(E/Z)-5-(2-(3-bromophenyl)hydrazinyl)-6-ethoxy-6-oxohex-4-enoic acid (3.57 g, 10 mmol) was dissolved in absolute ethanol (100 ml) followed by the addition of conc. sulfuric acid (2.7 ml, 50.5 mmol, 5.1 equiv.). The mixture was then allowed to reflux for 3 h at 100° C. Then the ethanol was evaporated and the residue was treated with 100 ml of ice-water. The aqueous solution was extracted with dichloromethane (3×50 ml); the organic layer was dried over magnesium sulfate, filtered and concentrated. The residue was purified by silica gel column chromatography using 20% of ethyl acetate in cyclohexane yielding a white solid in 85% yield.

(v) Ethyl 6-bromo-3-(3-ethoxy-3-oxopropyl)-1H-indole-2-carboxylate

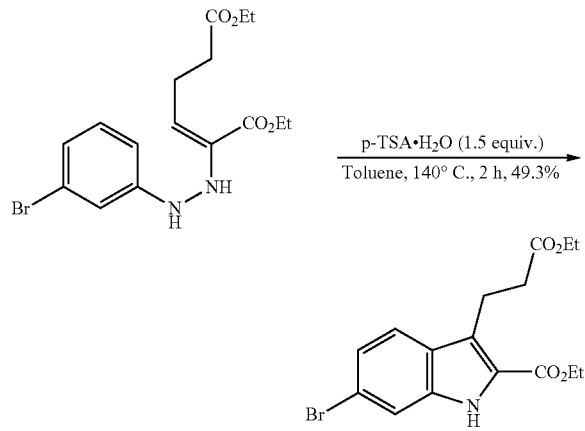

A mixture of p-toluenesulfonic acid (0.60 g, 3.12 mmol, 1.5 equiv.) and 100 ml of dry toluene was refluxed for 1 h at 140° C.; water was continuously removed by means of a Dean-Stark trap. Subsequently, 0.80 g (2.1 mmol) of the starting material ((E/Z)-diethyl 2-(2-(3-bromophenyl)hydrazinyl)hex-2-enedioate) dissolved in a minimum amount of dry toluene (ca. 15 ml) was added and the mixture was refluxed for 2 h. Then it was allowed to cool down to rt, and toluene was removed under reduced pressure and the residue was dissolved in dichloromethane and washed with water. The organic layer was dried over magnesium sulfate, filtered, and evaporated to dryness. The residue was purified by silica gel column chromatography using 20% of ethyl acetate/cyclohexane as eluent to yield a light-beige-colored solid in 49.3%. $^{1}$H-NMR (DMSO-d$_6$) δ 1.09, 1.34 (each t, 3H, $^{3}J$=7.1 Hz, CH$_3$); 2.57 (m, 2H, 2'-H); 3.27 (m, 2H, 1'-H); 3.98, 4.34 (each q, 2H, $^{4}J$=7.1 Hz, CH$_2$); 7.18 (dd, 1H, J=1.8 Hz, 5-H); 7.56 (dd, 1H, J=1.8 Hz, 7-H); 7.64 (dd, 1H, J=8.5 Hz, 4-H); 11.69 (s, 1H, NH). $^{13}$C-NMR (DMSO-d$_6$) δ 14.10, 14.25 (2CH$_3$, each C=OOCH$_2$CH$_3$); 19.9 (C-2'); 35.0 (C-1'); 59.9, 60.6 (2CH$_2$, each C=OOCH$_2$CH$_3$); 114.9 (C-7); 117.9 (C-4), 121.7 (C-3); 122.5 (C-6), 122.7 (C-5), 124.2 (C-2) 126.0 (C-3a) 136.9 (C-7a), 161.39 (2'-CO$_2$Et), 172.29 (2-CO$_2$Et). LC-MS (m/z): 387 [M-NH$_4^+$]$^+$, 370 [M]$^+$, 368 [M]$^-$. Purity (LC-MS): 97%.

(vi) 3-(2-Carboxyethyl)-6-bromo-1H-indole-2-carboxylic acid

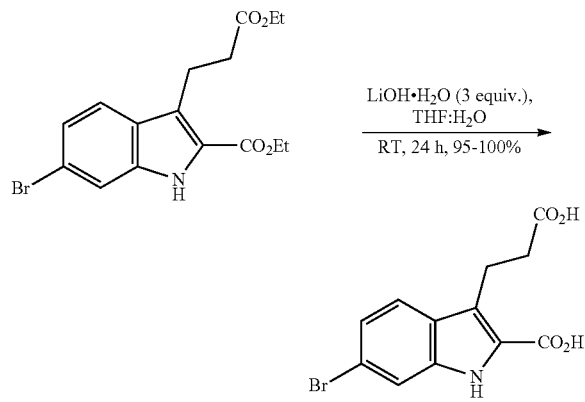

Ethyl 6-bromo-3-(3-ethoxy-3-oxopropyl)-1H-indole-2-carboxylate (3.68 g, 10 mmol) was dissolved in 25 ml tetrahydrofurane (THF) with stirring at rt. Then a solution of 1.26 g of lithium hydroxide trihydrate (3 equiv.) in 25 ml water was added and the resulting mixture was let to stir at rt for 24 h. After completion of the reaction THF was removed under reduced pressure and the pH was adjusted to 4-5, and the product was extracted with diethyl ether (3×30 ml). The organic layers were dried over magnesium sulfate, filtered, and evaporated to dryness to yield a light-beige-colored solid in 95-100% yield. mp. 234-235° C. $^{1}$H-NMR (DMSO-d$_6$) δ 2.50 (m, 2H, 2'-H); 3.23 (m, 2H, 1'-H); 7.16 (dd, 1H, J=1.8 Hz, 5-H); 7.54 (dd, 1H, J=1.8 Hz, 7-H); 7.64 (dd, 1H, J=8.5 Hz, 4-H); 11.57 (s, 1H, NH); 12.54 (b, 1H, 2CO$_2$H). $^{13}$C-NMR (DMSO-d$_6$) δ 19.9 (C-2'); 35.2 (C-1'); 114.9 (C-7); 117.6 (C-4); 121.6 (C-3); 122.5 (C-6, C-5); 125.0 (C-2); 126.2 (C-3a); 136.8 (C-7a); 163.0 (2'-CO$_2$H); 174.0 (2-CO$_2$H). LC-MS (m/z): 329 [M-NH4$^+$]$^+$, 312 [M]$^+$, 312 [M]$^-$. Purity (LC-MS): 99%.

(h) 3-(2-Carboxyethyl)-6-iodo-1H-indole-2-carboxylic acid (i) 3-Iodobenzenediazonium salt (mixture I)

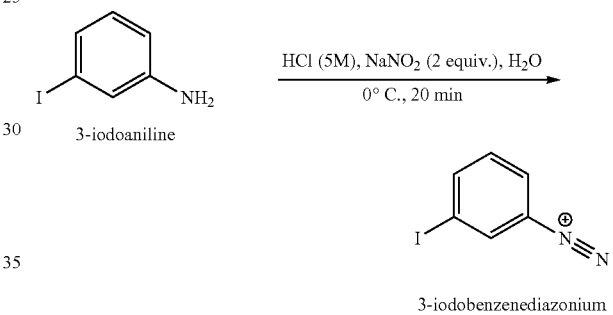

To a well stirred suspension of 3-iodoaniline (2.19 g, 10 mmol) in 16.6 ml HCl (5 M) at 0° C. was dropwise added a solution of sodium nitrite 1.38 g (20 mmol, 2 equiv.) in 8 ml water, previously cooled to 0° C. The addition of sodium nitrite solution was slow, in order to keep the temperature of the mixture below 8° C. The resulting orange-red mixture was stirred at 0° C. for further 20 min.

(ii) 2-(Ethoxycarbonyl)cyclopentanone (mixture II)

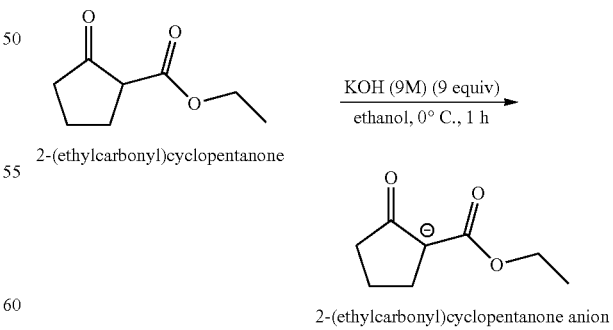

2-(Ethoxycarbonyl)cyclopentanone (2.51 ml, 1.34 g, 15 mmol) was dissolved in ethanol (4.2 ml) and cooled to 0° C. Then, a potassium hydroxide solution (5.04 g, 90 mmol, 9 equiv.) in water (5 ml) previously cooled to 0° C. was added dropwise within ca. 30 min in order to keep the temperature

(iii) (E/Z)-5-(2-(3-Iodophenyl)hydrazinyl)-6-ethoxy-6-oxohex-4-enoic acid

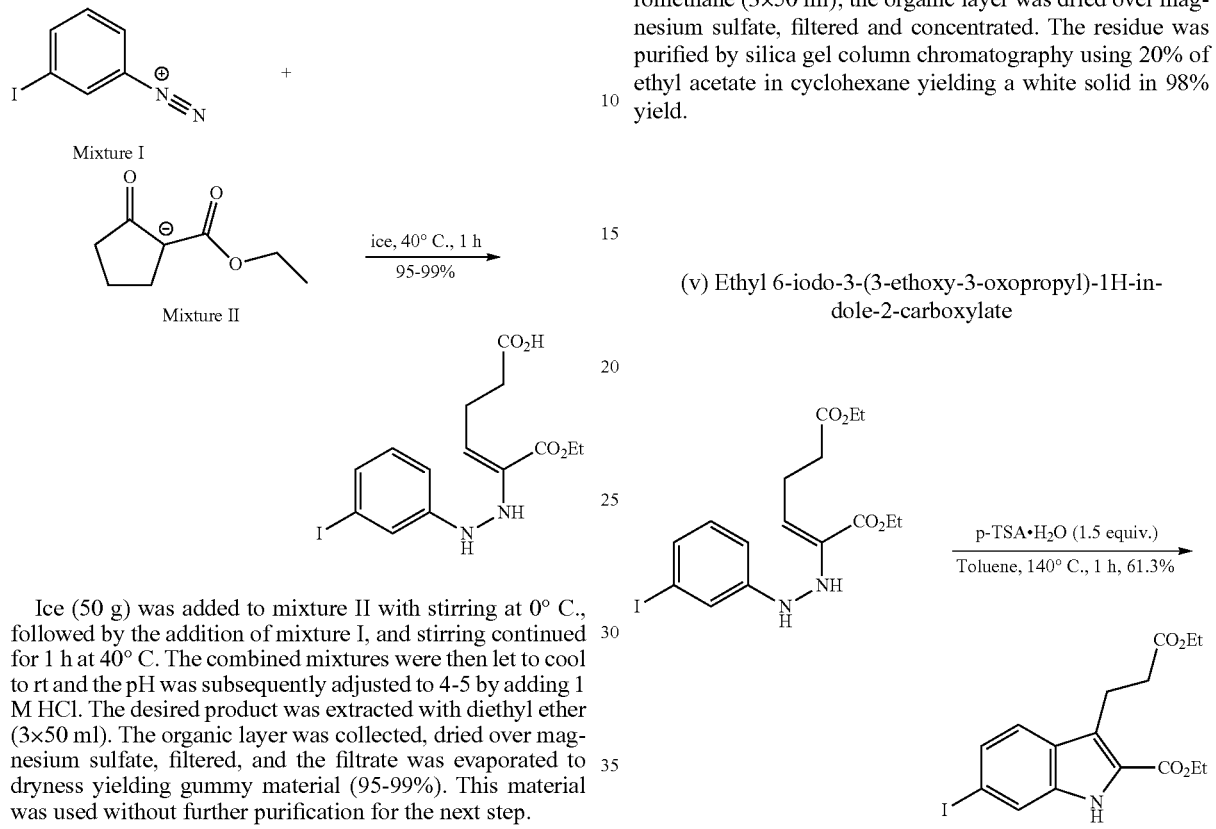

Ice (50 g) was added to mixture II with stirring at 0° C., followed by the addition of mixture I, and stirring continued for 1 h at 40° C. The combined mixtures were then let to cool to rt and the pH was subsequently adjusted to 4-5 by adding 1 M HCl. The desired product was extracted with diethyl ether (3×50 ml). The organic layer was collected, dried over magnesium sulfate, filtered, and the filtrate was evaporated to dryness yielding gummy material (95-99%). This material was used without further purification for the next step.

(iv) (E/Z)-Diethyl 2-(2-(3-iodophenyl)hydrazinyl)hex-2-enedioate

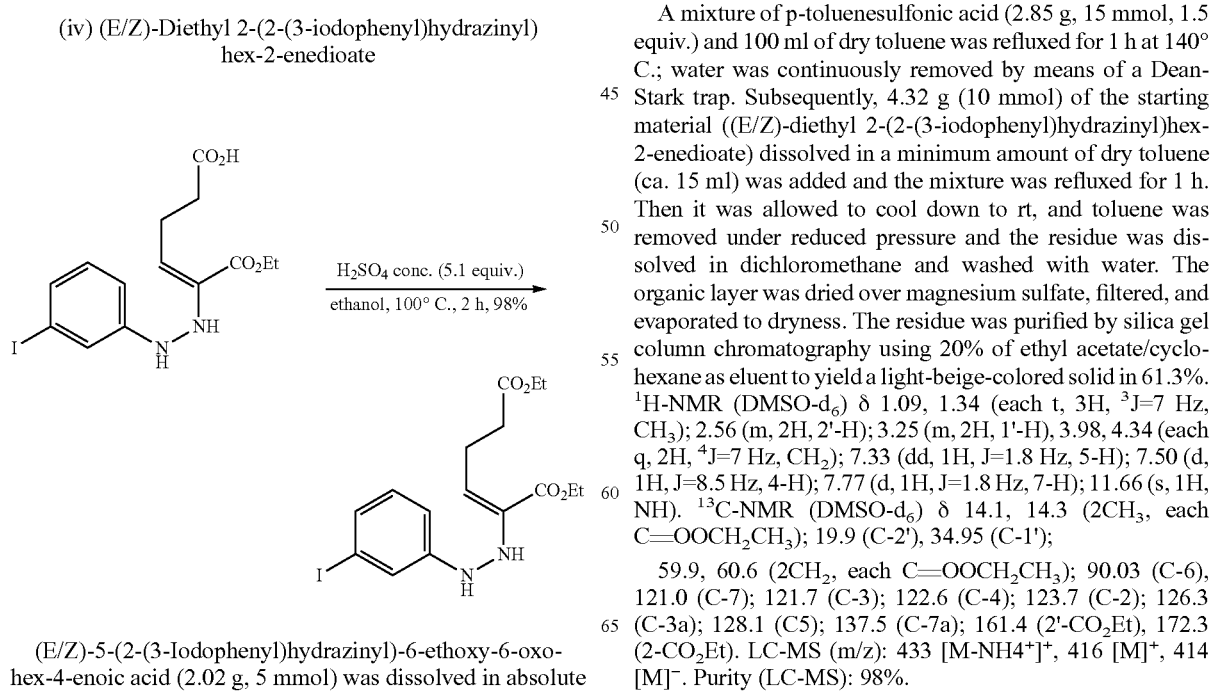

(E/Z)-5-(2-(3-Iodophenyl)hydrazinyl)-6-ethoxy-6-oxohex-4-enoic acid (2.02 g, 5 mmol) was dissolved in absolute ethanol (100 ml) followed by the addition of conc. sulfuric acid (1.35 ml, 25.5 mmol, 5.1 equiv.). The mixture was then allowed to reflux for 2 h at 100° C. Then the ethanol was evaporated and the residue was treated with 100 ml of ice-water. The aqueous solution was extracted with dichloromethane (3×50 ml); the organic layer was dried over magnesium sulfate, filtered and concentrated. The residue was purified by silica gel column chromatography using 20% of ethyl acetate in cyclohexane yielding a white solid in 98% yield.

(v) Ethyl 6-iodo-3-(3-ethoxy-3-oxopropyl)-1H-indole-2-carboxylate

A mixture of p-toluenesulfonic acid (2.85 g, 15 mmol, 1.5 equiv.) and 100 ml of dry toluene was refluxed for 1 h at 140° C.; water was continuously removed by means of a Dean-Stark trap. Subsequently, 4.32 g (10 mmol) of the starting material ((E/Z)-diethyl 2-(2-(3-iodophenyl)hydrazinyl)hex-2-enedioate) dissolved in a minimum amount of dry toluene (ca. 15 ml) was added and the mixture was refluxed for 1 h. Then it was allowed to cool down to rt, and toluene was removed under reduced pressure and the residue was dissolved in dichloromethane and washed with water. The organic layer was dried over magnesium sulfate, filtered, and evaporated to dryness. The residue was purified by silica gel column chromatography using 20% of ethyl acetate/cyclohexane as eluent to yield a light-beige-colored solid in 61.3%. $^1$H-NMR (DMSO-$d_6$) δ 1.09, 1.34 (each t, 3H, $^3J$=7 Hz, $CH_3$); 2.56 (m, 2H, 2'-H); 3.25 (m, 2H, 1'-H); 3.98, 4.34 (each q, 2H, $^4J$=7 Hz, $CH_2$); 7.33 (dd, 1H, J=1.8 Hz, 5-H); 7.50 (d, 1H, J=8.5 Hz, 4-H); 7.77 (d, 1H, J=1.8 Hz, 7-H); 11.66 (s, 1H, NH). $^{13}$C-NMR (DMSO-$d_6$) δ 14.1, 14.3 (2$CH_3$, each C=OO$CH_2CH_3$); 19.9 (C-2'), 34.95 (C-1');

59.9, 60.6 (2$CH_2$, each C=OO$CH_2CH_3$); 90.03 (C-6), 121.0 (C-7); 121.7 (C-3); 122.6 (C-4); 123.7 (C-2); 126.3 (C-3a); 128.1 (C5); 137.5 (C-7a); 161.4 (2'-$CO_2$Et), 172.3 (2-$CO_2$Et). LC-MS (m/z): 433 [M-NH4$^+$]$^+$, 416 [M]$^+$, 414 [M]$^-$. Purity (LC-MS): 98%.

(vi) 3-(2-Carboxyethyl)-6-iodo-1H-indole-2-carboxylic acid

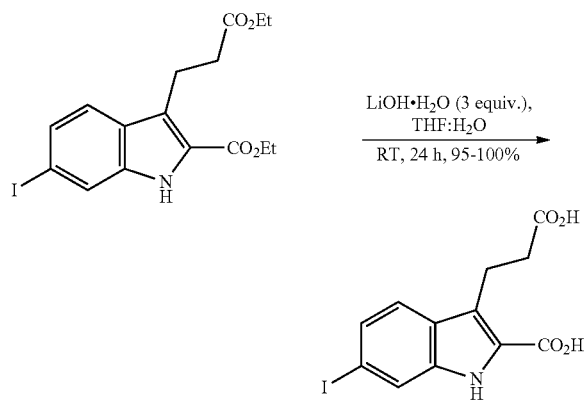

Ethyl 6-iodo-3-(3-ethoxy-3-oxopropyl)-1H-indole-2-carboxylate (4.15 g, 10 mmol) was dissolved in 25 ml tetrahydrofurane (THF) with stirring at rt. Then a solution of 1.26 g of lithium hydroxide trihydrate (3 equiv.) in 25 ml water was added and the resulting mixture was let to stir at rt for 24 h. After completion of the reaction THF was removed under reduced pressure and the pH was adjusted to 4-5, and the product was extracted with diethyl ether (3×30 ml). The organic layers were dried over magnesium sulfate, filtered, and evaporated to dryness to yield a light-beige-colored solid in 95-100% yield. mp. 230-232° C. $^1$H-NMR (DMSO-$d_6$) δ 2.49 (m, 2H, 2'-H); 3.22 (m, 2H, 1'-H); 7.31 (dd, 1H, J=1.8 Hz, 5-H); 7.50 (d, 1H, J=8.5 Hz, 4-H); 7.74 (d, 1H, J=1.8 Hz, 7-H); 11.52 (s, 1H, NH); 12.53 (b, 2H, 2CO$_2$H). $^{13}$C-NMR (DMSO-$d_6$) δ 19.9 (C2'); 35.2 (C1'); 89.6 (C-6); 121.0 (C-7); 121.6 (C-3); 122.7 (C-4); 124.6 (C-2); 126.5 (C-3a); 127.9 (C-5); 137.3 (C-7a); 163.0 (2'-CO$_2$H); 174.0 (2-CO$_2$H). LC-MS (m/z): 377 [M-NH4$^+$]$^+$, 360 [M]$^+$, 358 [M]$^-$. Purity (LC-MS): 98%.

(I) 3-(2-Carboxyethyl)-4,6-diiodo-1H-indole-2-carboxylic acid

(i) 3,5-Diiodobenzenediazonium salt (mixture I)

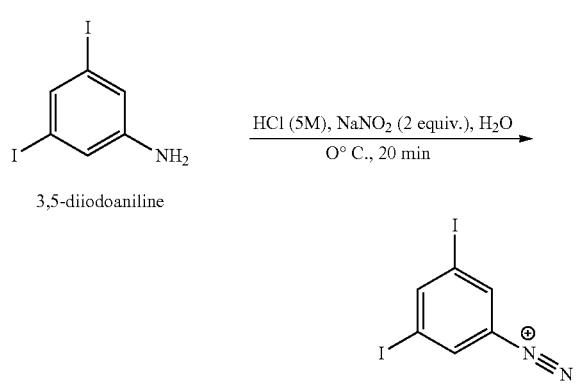

To a well stirred suspension of 3,5-diiodoaniline (3.45 g, 10 mmol) in 16.6 ml HCl (5 M) at 0° C. was dropwise added a solution of sodium nitrite 1.38 g (20 mmol, 2 equiv.) in 8 ml water, previously cooled to 0° C. The addition of sodium nitrite solution was slow, in order to keep the temperature of the mixture below 8° C. The resulting orange-red mixture was stirred at 0° C. for further 20 min.

(ii) 2-(Ethoxycarbonyl)cyclopentanone (mixture II)

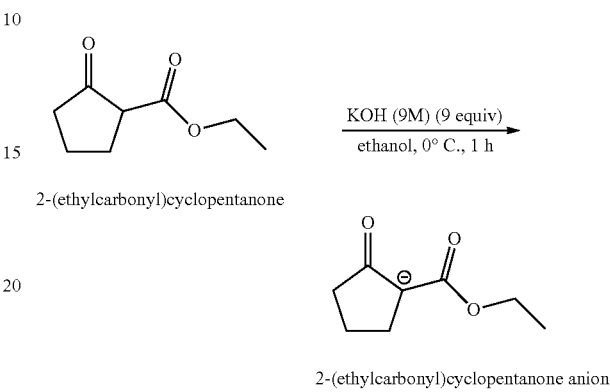

2-(Ethoxycarbonyl)cyclopentanone (2.51 ml, 1.34 g, 15 mmol) was dissolved in ethanol (4.2 ml) and cooled to 0° C. Then, a potassium hydroxide solution (5.04 g, 90 mmol, 6 equiv.) in water (5 ml) previously cooled to 0° C. was added dropwise within ca. 30 min in order to keep the temperature below 8° C. The mixture turned to a white-milky color, and the final mixture was stirred at 0° C. for further 30 min.

(iii) (E/Z)-5-(2-(3,5-Diiodophenyl)hydrazinyl)-6-ethoxy-6-oxohex-4-enoic acid

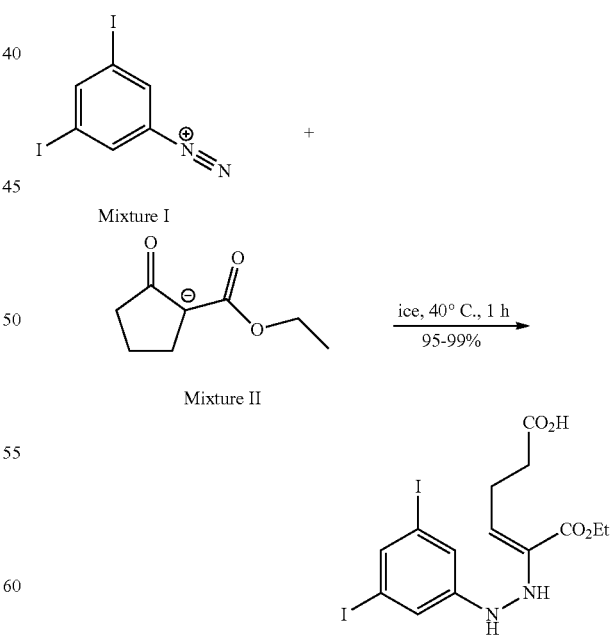

Ice (50 g) was added to mixture II with stirring at 0° C., followed by the addition of mixture I, and stirring continued for 1 h at 40° C. The combined mixtures were then let to cool to rt and the pH was subsequently adjusted to 4-5 by adding 1

M HCl. The desired product was extracted with diethyl ether (3×50 ml). The organic layer was collected, dried over magnesium sulfate, filtered, and the filtrate was evaporated to dryness yielding gummy material (95-99%). This material was used without further purification for the next step.

(iv) (E/Z)-Diethyl 2-(2-(3,5-diiodophenyl)hydrazinyl)hex-2-enedioate

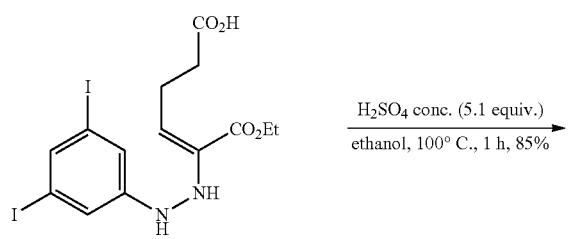

(E/Z)-5-(2-(3,5-Diiodophenyl)hydrazinyl)-6-ethoxy-6-oxohex-4-enoic acid (5.30 g, 10 mmol) was dissolved in absolute ethanol (100 ml) followed by the addition of conc. sulfuric acid (2.7 ml, 50.5 mmol, 5.1 equiv.). The mixture was then allowed to reflux for 1 h at 100° C. Then the ethanol was evaporated and the residue was treated with 100 ml of ice-water. The aqueous solution was extracted with dichloromethane (3×50 ml); the organic layer was dried over magnesium sulfate, filtered and concentrated. The residue was purified by silica gel column chromatography using 20% of ethyl acetate in cyclohexane yielding a white solid in 85% yield.

(v) Ethyl 4,6-diiodo-3-(3-ethoxy-3-oxopropyl)-1H-indole-2-carboxylate

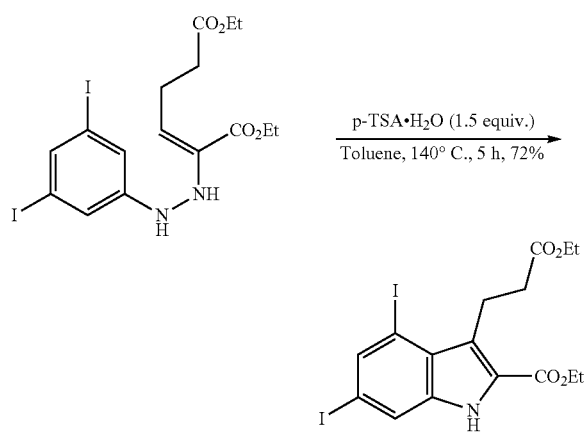

A mixture of p-toluenesulfonic acid (2.43 g, 12.75 mmol, 1.5 equiv.) and 100 ml of dry toluene was refluxed for 1 h at 140° C.; water was continuously removed by means of a Dean-Stark trap. Subsequently, 4.75 g (8.5 mmol) of the starting material ((E/Z)-diethyl 2-(2-(3,5-diiodophenyl)hydrazinyl)hex-2-enedioate) dissolved in a minimum amount of dry toluene (ca. 15 ml) was added and the mixture was refluxed for 5 h. Then it was allowed to cool down to rt, and toluene was removed under reduced pressure and the residue was dissolved in dichloromethane and washed with water. The organic layer was dried over magnesium sulfate, filtered, and evaporated to dryness. The residue was purified by silica gel column chromatography using 20% of ethyl acetate/cyclohexane as eluent to yield a light-beige-colored solid in 72%. $^1$H-NMR (DMSO-$d_6$) δ 1.17, 1.34 (each t, 3H, $^3$J=7.1 Hz, CH$_3$); 2.55 (m, 2H, 2'-H); 3.53 (m, 2H, 1'-H); 4.06, 4.34 (each q, 2H, $^4$J=7.1 Hz, CH$_2$); 7.80 (d, 2H, J=1.7 Hz, 5-H, 7-H), 11.91 (s, 1H, NH). $^{13}$C-NMR (DMSO-$d_6$) δ 14.2 (2CH$_3$, each C=OOCH$_2$CH$_3$); 19.1 (C-2'); 36.1 (C-1'); 59.9, 60.9 (2CH$_2$, each C=OOCH$_2$CH$_3$); 88.3 (C-4); 90.0 (C-6); 121.5 (C-7); 122.1 (C-3); 125.4 (C-2); 126.0 (C-3a); 137.9 (C-7a); 138.4 (C-5); 161.1 (2-CO$_2$Et); 171.9 (2-CO$_2$Et). LC-MS (m/z): 542 [M]$^+$, 559 [M+NH$_4^+$]$^+$, 540 [M]$^-$. purity (LC-SM): 98%.

(vi) 3-(2-Carboxyethyl)-4,6-diiodo-1H-indole-2-carboxylic acid

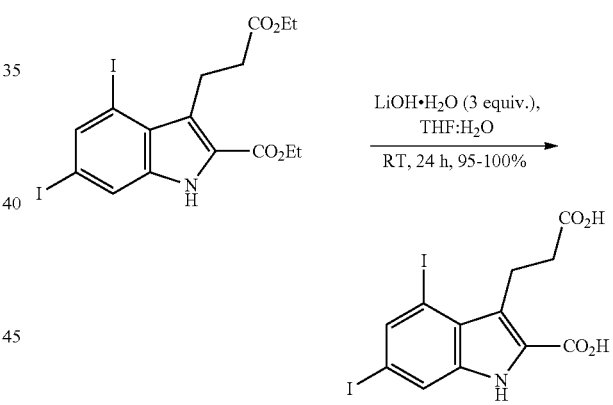

Ethyl 4,6-diiodo-3-(3-ethoxy-3-oxopropyl)-1H-indole-2-carboxylate (1.71 g, 5 mmol) was dissolved in 15 ml tetrahydrofurane (THF) with stirring at rt. Then a solution of 0.63 g of lithium hydroxide trihydrate (3 equiv.) in 15 ml water was added and the resulting mixture was let to stir at rt for 24 h. After completion of the reaction THF was removed under reduced pressure and the pH was adjusted to 4-5, and the product was extracted with diethyl ether (3×15 ml). The organic layers were dried over magnesium sulfate, filtered, and evaporated to dryness to yield a light-beige-colored solid in 95-100% yield. mp. 280-282° C. $^1$H-NMR (DMSO-$d_6$) δ 2.48 (m, 2H, 2'-H); 3.49 (m, 2H, 1'-H); 7.78 (dd, 2H, J=1.7 Hz, 5-H, 7-H); 11.80 (s, 1H, NH); 12.68 (b, 2H, 2CO$_2$H). $^{13}$C-NMR (DMSO-$d_6$) δ 18.9 (C-2'); 36.4 (C-1'); 88.3 (C-4); 89.5 (C-6); 121.4 (C-7); 122.0 (C-3); 126.2 (C-2); 126.4 (C-3a); 137.8 (C-7a); 138.1 (C7); 162.7 (2'-CO$_2$H); 173.58 (2-CO$_2$H). LC-MS (m/z): 503 [M+NH4$^+$]$^+$, 486 [M]$^+$, 484 [M]$^-$. Purity (LC-MS): 98%.

(j) 3-(2-Carboxyethyl)-4,6-dichloro-5-fluoro-1H-indole-2-carboxylic acid

(i) 3,5-Dichloro-4-fluorobenzenediazonium salt (Mixture I)

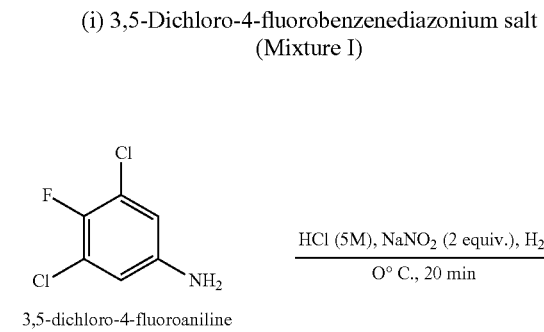

To a well stirred suspension of 3,5-dichloro-4-fluoroaniline (0.90 g, 5 mmol) in 8.3 ml HCl (5 M) at 0° C. was dropwise added a solution of sodium nitrite 0.69 g (10 mmol, 2 equiv.) in 4 ml water, previously cooled to 0° C. The addition of sodium nitrite solution was slow, in order to keep the temperature of the mixture below 8° C. The resulting orange-red mixture was stirred at 0° C. for further 20 min.

(ii) 2-(Ethoxycarbonyl)cyclopentanone (mixture II)

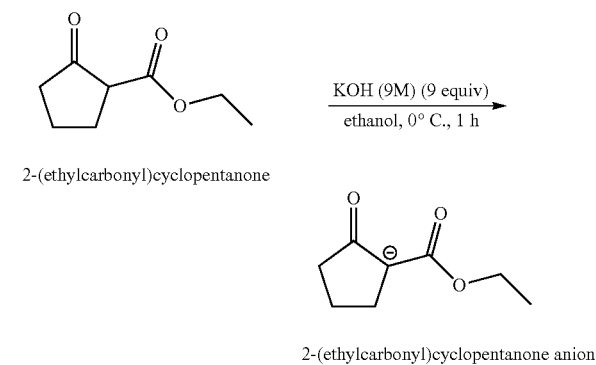

2-(Ethoxycarbonyl)cyclopentanone (1.26 ml, 0.67 g, 7.5 mmol) was dissolved in ethanol (4.2 ml) and cooled to 0° C. Then, a potassium hydroxide solution (2.52 g, 45 mmol, 9 equiv.) in water (5 ml) previously cooled to 0° C. was added dropwise within ca. 30 min in order to keep the temperature below 8° C. The mixture turned milky-white and the final mixture was stirred at 0° C. for further 30 min.

(iii) (E/Z)-5-(2-(3,5-Dichloro-5-fluorophenyl)hydrazinyl)-6-ethoxy-6-oxohex-4-enoic acid

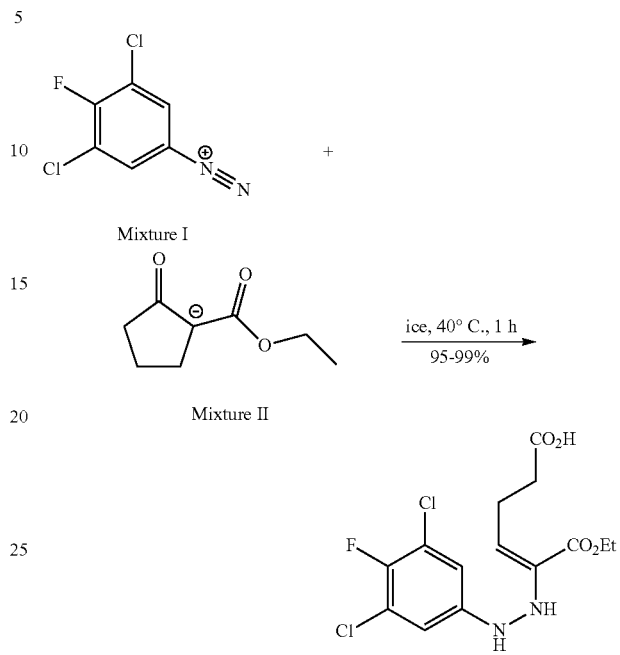

Ice (50 g) was added to mixture II with stirring at 0° C., followed by the addition of mixture I, and stirring continued for 1 h at 40° C. The combined mixtures were then let to cool to rt and the pH was subsequently adjusted to 4-5 by adding 1 M HCl. The desired product was extracted with diethyl ether (3×50 ml). The organic layer was collected, dried over magnesium sulfate, filtered, and the filtrate was evaporated to dryness yielding gummy material (95-99%). This material was used without further purification for the next step.

(iv) (E/Z)-Diethyl 2-(2-(3,5-dichloro-4-fluorophenyl)hydrazinyl)hex-2-enedioate

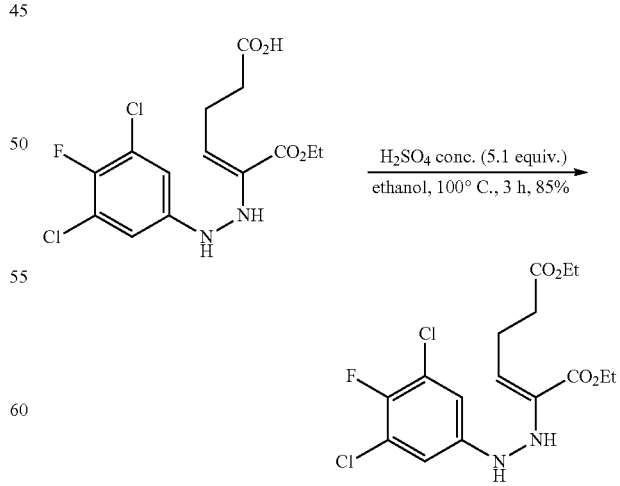

(E/Z)-5-(2-(3,5-Dichloro-4-fluorophenyl)hydrazinyl)-6-ethoxy-6-oxohex-4-enoic acid (1.83 g, 5 mmol) was dissolved in absolute ethanol (100 ml) followed by the addition of conc. sulfuric acid (1.35 ml, 25.3 mmol, 5.1 equiv.). The mixture was then allowed to reflux for 1 h at 100° C. Then the ethanol was evaporated and the residue was treated with 100 ml of ice-water. The aqueous solution was extracted with dichloromethane (3×50 ml); the organic layer was dried over magnesium sulfate, filtered and concentrated. The residue was purified by silica gel column chromatography using 20% of ethyl acetate in cyclohexane yielding a white solid in 85% yield.

(v) Ethyl 4,6-dichloro-4-fluoro-3-(3-ethoxy-3-oxopropyl)-1H-indole-2-carboxylate

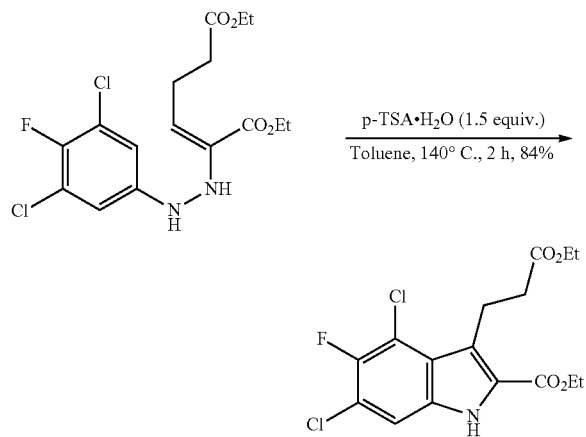

A mixture of p-toluenesulfonic acid (1.22 g, 6.4 mmol, 1.5 equiv.) and 60 ml of dry toluene was refluxed for 1 h at 140° C.; water was continuously removed by means of a Dean-Stark trap. Subsequently, 1.67 g (4.25 mmol) of the starting material ((E/Z)-diethyl 2-(2-(3,5-dibromophenyl)hydrazinyl)hex-2-enedioate) dissolved in a minimum amount of dry toluene (ca. 15 ml) was added and the mixture was refluxed for 2 h. Then it was allowed to cool down to rt, and toluene was removed under reduced pressure and the residue was dissolved in dichloromethane and washed with water. The organic layer was dried over magnesium sulfate, filtered, and evaporated to dryness. The residue was purified by silica gel column chromatography using 20% of ethyl acetate/cyclohexane as eluent to yield a light-beige-colored solid in 84%. $^1$H-NMR (DMSO-d$_6$) δ 1.14, 1.34 (each t, 3H, $^3$J=7.1 Hz, CH$_3$); 2.54 (m, 2H, 2'-H); 3.48 (m, 2H, 1'-H); 4.04, 4.35 (each q, 2H, $^4$J=7.1 Hz, CH$_2$); 7.50 (d, 1H, $^2$J=6 Hz, 7-H); 12.08 (s, 1H, NH). $^{13}$C-NMR (DMSO-d$_6$) δ 14.1 (2CH$_3$, each C=OOCH$_2$CH$_3$); 20.1 (C-2'); 35.9 (C-1'); 59.9, 61.0 (2CH$_2$, each C=OOCH$_2$CH$_3$); 112.6 (C-7); 113.0, 113.2, 117.9, 188.1, 121.4, 121.5 (C-5); 122.1 (C-4); 126.8 (C-6); 132.7 (C-3); 147.3 (C-3a); 149.1 (C-2); 160.9 (2'-CO$_2$Et), 171.9 (2-CO$_2$Et). LC-MS (m/z): 377 [M-NH4$^+$]$^+$, 360 [M]$^+$, 358 [M]$^-$. Purity (LC-MS): 96%.

(vi) 3-(2-Carboxyethyl)-4,6-dichloro-4-fluoro-1H-indole-2-carboxylic acid

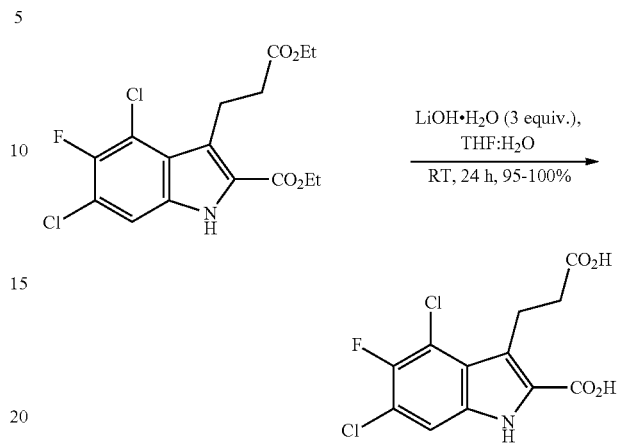

Ethyl 4,6-dichloro-4-fluoro-3-(3-ethoxy-3-oxopropyl)-1H-indole-2-carboxylate (1.13 g, 3 mmol) was dissolved in 15 ml tetrahydrofurane (THF) with stirring at rt. Then a solution of 0.38 g of lithium hydroxide trihydrate (3 equiv.) in 15 ml water was added and the resulting mixture was let to stir at rt for 24 h. After completion of the reaction THF was removed under reduced pressure and the pH was adjusted to 4-5, and the product was extracted with diethyl ether (3×15 ml). The organic layers were dried over magnesium sulfate, filtered, and evaporated to dryness to yield a light-beige-colored solid in 95-100% yield. mp. 292-294° C. $^1$H-NMR (DMSO-d$_6$) δ 2.48 (m, 2H, 2'-H); 3.48 (m, 2H, 1'-H); 7.49 (dd, 1H, $^2$J=6 Hz, 7-H); 11.98 (s, 1H, NH); 12.72 (b, 2H, 2CO$_2$H). $^{13}$C-NMR (DMSO-d$_6$) δ 20.1 (C-2'); 36.1 (C-1'); 112.5 (C-7); 113.0, 113.2, 117.6, 117.7, 121.3, 121.4 (C-5); 122.3 (C-4); 127.7 (C-6); 132.5 (C-3); 147.2 (C-3a); 149.0 (C-2); 162.5 (2'-CO$_2$H), 173.6 (2-CO$_2$H). LC-MS (m/z): 337 [M-NH4$^+$]$^+$, 320 [M]$^+$, 318 [M]$^-$. Purity (LC-MS): 98.6%.

(I) 3-(2-Carboxyethyl)-4,6-diphenyl-1H-indole-2-carboxylic acid

(i) Ethyl 4,6-diphenyl-3-(3-ethoxy-3-oxopropyl)-1H-indole-2-carboxylate

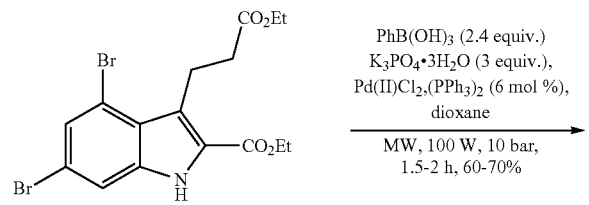

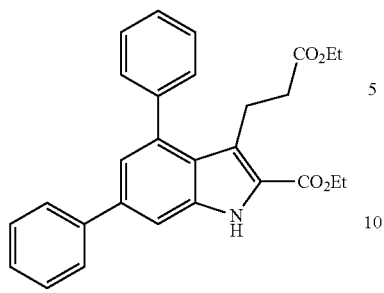

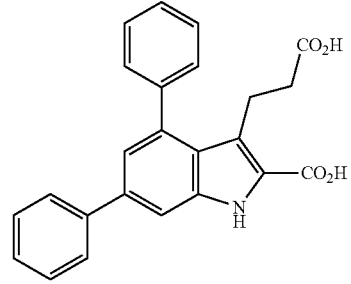

Ethyl 4,6-dibromo-3-(3-ethoxy-3-oxopropyl)-1H-indole-2-carboxylate (0.244 g, 0.5 mmol), phenylboronic acid (0.147 g, 1.2 mmol, 2.4 equiv.) and potassium phosphate trihydrate (0.400 g, 1.5 mmol, 3.0 equiv.) were mixed together in a 10 ml microwave vial. The vial was purged with Argon and trans-dichlorobis(triphenylphosphine)-palladium (II) (0.021, 0.03 mmol, 6 mol %) and 5 ml of dry dioxane were added to the mixture. The microwave vial was capped and irradiated at 100 watt, 150° C., under pressure up to 10 bars. Then it was allowed to cool down to rt, and toluene was removed under reduced pressure and the residue was dissolved in dichloromethane and washed with water. The organic layer was dried over magnesium sulfate, filtered, and evaporated to dryness. The residue was purified by silica gel column chromatography using 20% of ethyl acetate/cyclohexane as eluent to yield a light-beige-colored solid in 60-70%. $^1$H-NMR (DMSO-d$_6$) δ 1.09, 1.32 (each t, 3H, $^3$J=7.1 Hz, CH$_3$); 2.11 (m, 2H, 2'-H); 2.84 (m, 2H, 1'-H); 3.89, 4.33 (each q, 2H, $^4$J=7.1 Hz, CH$_2$); 7.12 (d, 1H, $^2$J=1.6 Hz, 7-H); 7.35 (t, 1H, $^3$J=7.4 Hz, Ph-ring); 7.43 (m, 7H, Ph-ring); 7.67 (d, 1H, $^2$J=0.9 Hz, 5-H); 7.68 (d, 1H, $^2$J=1.6 Hz, Phenyl-ring); 11.84 (s, 1H, NH). $^{13}$C-NMR (DMSO-d$_6$) δ 14.2, 14.3 (2CH$_3$, each C=OOCH$_2$CH$_3$); 20.5 (C-2'); 34.8 (C-1'); 59.5, 60.5 (2CH$_2$, each C=OOCH$_2$CH$_3$); 109.6 (C-5); 121.1 (C-7); 121.8 (C-3); 123.6 (C-2); 124.7 (C-3a); 127.0 (C-2", C-6"); 127.4 (C-4'''); 127.5 (C-4"); 128.0 (C-3''', C-5'''); 129.0 (C-3", C-5"); 129.1 (C-2''', C-6'''); 136.7 (C-7a); 137.4 (C-4), 137.6 (C-6); 140.7 (C-1"); 140.8 (C-1'''); 161.5 (2'-CO$_2$Et); 171.7 (2-CO$_2$Et). LC-MS (m/z): 442 [M]$^+$, 440 [M]$^-$. Purity (LC-MS): 96%.

(ii) 3-(2-Carboxyethyl)-4,6-diphenyl-1H-indole-2-carboxylic acid

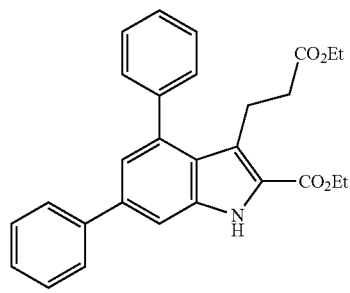

Ethyl 4,6-diphenyl-3-(3-ethoxy-3-oxopropyl)-1H-indole-2-carboxylate (4.42 g, 10 mmol) was dissolved in 25 ml tetrahydrofurane (THF) with stirring at rt. Then a solution of 1.26 g of lithium hydroxide trihydrate (3 equiv.) in 25 ml water was added and the resulting mixture was let to stir at rt for 24 h. After completion of the reaction THF was removed under reduced pressure and the pH was adjusted to 4-5, and the product was extracted with diethyl ether (3×25 ml). The organic layers were dried over magnesium sulfate, filtered, and evaporated to dryness to yield a light-beige-colored solid in 95-100% yield. mp. 243-245° C. $^1$H-NMR (DMSO-d$_6$) δ 2.07 (m, 2H, 2'-H); 2.83 (m, 2H, 1'-H); 7.09 (d, 1H, $^2$J=1.6 Hz, 7-H); 7.34 (t, 1H, $^3$J=7.4 Hz, ph-ring), 7.44 (m, 7H, Ph-ring), 7.66 (d, 2H, $^2$J=0.9 Hz, 5-H); 7.68 (d, 1H, 1.6 Hz, Ph-ring); 11.72 (s, 1H, NH); 12.33 (b, 2H, 2CO$_2$H). $^{13}$C-NMR (DMSO-d$_6$) δ 20.3 (C-2'); 34.9 (C-1'); 109.5 (C-4); 120.9 (C-6); 121.7 (C-3); 123.8 (C-2); 125.5 (C-3a); 127.0 (C-2", C-6"); 127.3 (C-4'''); 127.5 (C-4"); 128.0 (C-3''', C-5'''); 129.0 (C-3", C-5"); 129.1 (C-2''', C-6'''); 135.4 (C-7a); 137.3 (C-4), 137.4 (C-6); 140.8 (C-1"); 141.0 (C-1'''); 163.1 (2'-CO$_2$H); 173.4 (2-CO$_2$H). LC-MS (m/z): 386 [M-NH$_4^+$]$^+$, 366 [M]$^+$, 384 [M]$^-$. Purity (LC-MS): 95%.

(k) 3-(2-Carboxyethyl)-6-phenyl-1H-indole-2-carboxylic acid (i) Ethyl 6-phenyl-3-(3-ethoxy-3-oxopropyl)-1H-indole-2-carboxylate

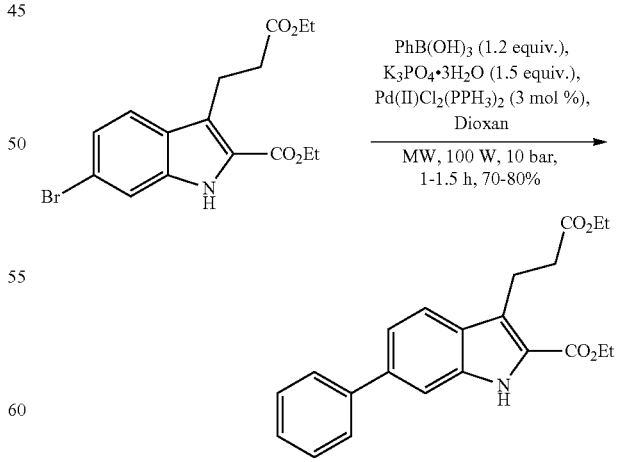

Ethyl 6-bromo-3-(3-ethoxy-3-oxopropyl)-1H-indole-2-carboxylate (0.185 g, 0.500 mmol), phenylboronic acid (0.76 g, 0.625 mmol, 1.2 equiv.) and potassium phosphate trihydrate (0.200 g, 0.750 mmol, 1.5 equiv.) were mixed together in a 10 ml microwave vial. The vial was purged with Argon and trans-dichlorobis(triphenylphosphine)-palladium (II) (0.0105 g, 0.015 mmol, 3 mol %) and 5 ml of dry dioxane were added to the mixture. The microwave vial was capped and irradiated at 100 watt, 150° C., under pressure up to 10 bars. Then it was allowed to cool down to rt, and toluene was removed under reduced pressure and the residue was dissolved in dichloromethane and washed with water. The organic layer was dried over magnesium sulfate, filtered, and evaporated to dryness. The residue was purified by silica gel column chromatography using 20% of ethyl acetate/cyclohexane as eluent to yield a light-beige-colored solid in 70-80%. $^1$H-NMR (DMSO-d$_6$) δ 1.11, 1.35 (each t, 3H, $^3$J=7.1 Hz, CH$_3$); 2.60 (m, 2H, 2'-H); 3.31 (m, 2H, 1'-H); 3.99, 4.35 (each q, 2H, $^4$J=7.1 Hz, CH$_2$); 7.35 (m, 2H, 4-H, 5-H); 7.46 (m, 2H, 2"-H, 6"-H); 7.62 (dd, 1H, 4"-H); 7.65 (m, 2H, 3"-H, 5"-H); 7.75 (dd, 1H, 7-H); 11.63 (s, 1H, NH). $^{13}$C-NMR (DMSO-d$_6$) δ 14.9, 15.1 (2CH$_3$, each C=OOCH$_2$CH$_3$); 20.90 (C-2'); 35.9 (C-1'); 60.7, 61.2 (2CH$_2$, each C=OOCH$_2$CH$_3$); 111.0 (C-7); 120.1 (C-4); 121.8 (C-3); 122.3 (C-3a); 124.8 (C-5) 127.2 (C-2", C-6"); 127.7 (C-4"); 128.0 (C-3", C-5"); 129.8 (C-2); 137.7 (C-7a); 138.2 (C-6); 141.9 (C-1"); 162.3 (2'-CO$_2$Et); 173.1 (2-CO$_2$Et). LC-MS (m/z): 383 [M-NH$_4^+$]$^+$, 366 [M]$^+$, 364 [M]$^-$. Purity LC-MS: 96%.

(ii) 3-(2-Carboxyethyl)-6-phenyl-1H-indole-2-carboxylic acid

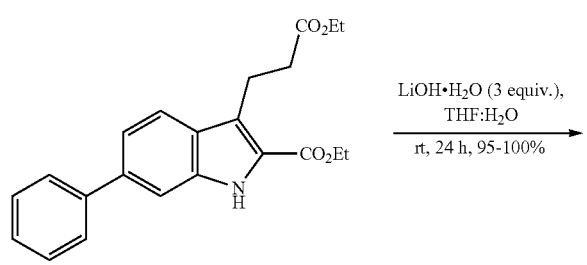

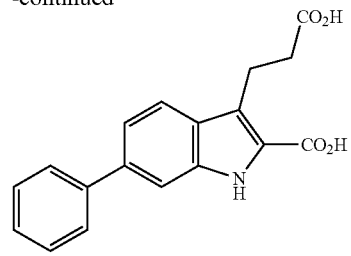

Ethyl 6-phenyl-3-(3-ethoxy-3-oxopropyl)-1H-indole-2-carboxylate (3.65 g, 10 mmol) was dissolved in 25 ml tetrahydrofurane (THF) with stirring at rt. Then a solution of 1.26 g of lithium hydroxide trihydrate (3 equiv.) in 25 ml water was added and the resulting mixture was let to stir at rt for 24 h. After completion of the reaction THF was removed under reduced pressure and the pH was adjusted to 4-5, and the product was extracted with diethyl ether (3×25 ml). The organic layers were dried over magnesium sulfate, filtered, and evaporated to dryness to yield a light-beige-colored solid in 95-100% yield. mp. 238-239° C. $^1$H-NMR (DMSO-d$_6$) δ 2.54 (m, 2H, 2'-H); 3.28 (m, 2H, 1'-H); 7.35 (m, 2H, 4-H, 5-H); 7.46 (m, 2H, 2"-H, 6"-H); 7.60 (dd, 1H, 4"-H); 7.63 (m, 2H, 3"-H, 5"-H); 7.75 (dd, 1H, 7-H); 11.55 (s, 1H, NH); 12.50 (b, 2H, 2CO$_2$H). $^{13}$C-NMR (DMSO-d$_6$) δ 20.1 (C2'); 35.3 (C1'); 110.2 (C-7); 119.2 (C-5), 121.1 (C-4); 121.4 (C-3); 124.8 (C-3a); 126.6 (C-2); 127.0 (C-3", C-5"); 127.2 (C-4"); 129.1 (C-3", C-6"); 136.8 (C-7a); 137.6 (C-6); 141.3 (C-1"); 163.1 (2'-CO$_2$H); 174.1 (2-CO$_2$H). LC-MS (m/z): 310 [M]$^+$, 308 [M]$^-$. Purity (LC-MS): 98%.

The compounds listed in Table 2 can be produced using the methods and manufacturing routes similar to and based on the manufacturing schemes disclosed in the experimental section hereinbefore, which can be adapted by one skilled in the art, accordingly.

---

What is claimed is:

1. A method of identifying a compound that modulates GPR 17 biological activity comprising the steps of
   (a) contacting a compound with a GPR17, or a functional GPR17 fragment in the presence of a suitable amount of a GPR17 agonist of formula I

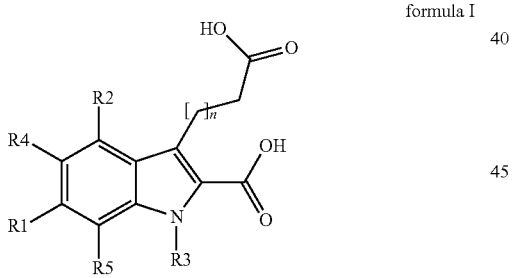

formula I or a salt thereof,
   (b) measuring the biological activity of said GPR17 or said functional GPR17 fragment after addition of said compound, and
   (c) comparing the biological activity measured in step (b) with the biological activity of said GPR17 or said functional fragment thereof in the presence of said GPR 17 agonist of formula I without the addition of said compound to identify whether the compound is one that modulates GPR17 activity,
wherein in formula I
   R1 and R2 are independently selected from the group comprising hydrogen, halogen, hydroxy, formyl, oxime, cyano, nitro, amino, NR6R7, carboxy, carbamoyl, $(C_1\text{-}C_8)$alkyl, $(C_1\text{-}C_8)$alkyloxy, $(C_1\text{-}C_8)$alkylthio, $(C_2\text{-}C_8)$alkenyl, $(C_2\text{-}C_8)$alkynyl, $(C_3\text{-}C_8)$cycloalkyl, $(C_3\text{-}C_8)$cycloalkyloxy, $(C_3\text{-}C_8)$cycloalkylamino, aryl, heteroaryl, aryloxy, heteroaryloxy, halogen, trifluoromethyl, $(C_1\text{-}C_8)$alkylcarbonyl, $(C_1\text{-}C_8)$alkylaminocarbonyl, di$(C_1\text{-}C_8)$alkylaminocarbonyl, arylcarbonyl, heteroarylcarbonyl, aryl$(C_1\text{-}C_8)$alkyl, heteroaryl$(C_1\text{-}C_8)$alkyl, aryl$(C_1\text{-}C_8)$alkyloxy, heteroaryl$(C_1\text{-}C_8)$alkyloxy, aryl$(C_1\text{-}C_8)$alkylcarbonyl, heteroaryl$(C_1\text{-}C_8)$alkylcarbonyl, aryl $(C_1\text{-}C_8)$alkyloxycarbonyl, heteroaryl$(C_1\text{-}C_8)$alkyloxycarbonyl, $(C_1\text{-}C_8)$alkyloxycarbonyl, $(C_1\text{-}C_8)$alkylsulfonyl, arylsulfonyl, heteroarylsulfonyl, sulfamoyl, sulfonylamino, $(C_1\text{-}C_8)$alkylaminosulfonyl, di$(C_1\text{-}C_8)$alkylaminosulfonyl, arylsulfonylamino, heteroarylsulfonylamino and $(C_1\text{-}C_8)$alkylsulfonylamino; wherein each alkyl, alkenyl, alkynyl or cycloalkyl may be unsubstituted or substituted with one or more residues selected from among hydroxyl, $(C_1\text{-}C_5)$alkyloxy, $(C_1\text{-}C_3)$alkyloxy$(C_1\text{-}C_3)$alkyloxy, halogen, and NR6R7; and wherein each aryl or heteroaryl can be unsubstituted or substituted with one or more residues selected from among hydroxyl, $(C_1\text{-}C_5)$alkyloxy, halogen, $(C_1\text{-}C_5)$alkyl, $(C_3\text{-}C_8)$cycloalkyl, carboxy, NR6R7, cyano, trifluormethyl and nitro;

R3 is selected from hydrogen, a group —$(CH_2)_m CH_2$—COOH, OH, NH, and $(C_1\text{-}C_5)$alkyl which is optionally substituted with one or more halogens, one or two hydroxyl groups or $(C_1\text{-}C_3)$alkoxy;

R4 is selected from hydrogen and fluoro;

R5 is selected from hydrogen, halogen, $(C_1\text{-}C_3)$alkyl, $(C_1\text{-}C_3)$alkyloxy, $(C_1\text{-}C_3)$alkylthio, $(C_2\text{-}C_4)$alkenyl, $(C_2\text{-}C_4)$alkynyl, and NR6R7;

R6 and R7 are independently selected from hydrogen, $(C_1\text{-}C_6)$alkyl, $(C_3\text{-}C_7)$cycloalkyl, phenyl, heteroaryl, phenyl $(C_1\text{-}C_6)$alkyl, heteroaryl$(C_1\text{-}C_6)$alkyl, $(C_1\text{-}C_6)$alkylsulfonyl, phenylsulfonyl, heteroarylsulfonyl, $(C_1\text{-}C_6)$alkylcarbonyl, $(C_1\text{-}C_6)$alkoxycarbonyl, aminocarbonyl, $(C_1\text{-}C_6)$alkylaminocarbonyl, phenylcarbonyl, and heteroarylcarbonyl; wherein each alkyl may be unsubstituted or substituted with one or more residues selected from among hydroxyl, $(C_1-C_3)$alkyloxy, phenyl, halo, carboxy, and NR8R9; and wherein R6 and R7 may form a 5- to 7-membered cycle; and wherein phenyl or heteroaryl can be unsubstituted or substituted with one or more residues selected from among hydroxyl, $(C_1-C_3)$ alkyloxy, halogen, $(C_1-C_3)$alkyl, carboxy, NR8R9, cyano, trifluormethyl and nitro;

R8 and R9 are independently selected from among hydrogen and $(C_1-C_3)$alkyl;

n and m are independently 0, 1 or 2.

2. The method according to claim 1, wherein in formula I

R1 is selected from fluoro, chloro, bromo, iodo, $(C_1-C_3)$alkyl, $(C_1-C_3)$alkoxy, phenyl, phenyl$(C_1-C_3)$alkyl, phenyl$(C_1-C_3)$alkoxy, phenylcarbonyl, $(C_5-C_6)$heteroaryl, $(C_5-C_6)$heteroarylcarbonyl, $(C_5-C_6)$heteroaryl$(C_1-C_3)$alkyl and $(C_5-C_6)$heteroaryl$(C_1-C_3)$alkoxy, wherein the alkyl and alkoxy groups are optionally substituted with one or more halogens, $(C_1-C_3)$alkoxy, or hydroxyl, and wherein the phenyl and $(C_5-C_6)$heteroaryl groups can be substituted with one or more halogens, $(C_1-C_3)$alkoxy, $(C_1-C_3)$alkyl, NR6R7, or hydroxyl;

R2 is selected from hydrogen, fluoro, chloro, bromo, iodo, $(C_1-C_3)$alkyl, $(C_1-C_3)$alkoxy, and phenyl, wherein the alkyl and alkoxy groups are optionally substituted with one or more halogens, $(C_1-C_3)$alkoxy, or hydroxyl, and wherein the phenyl group can be substituted with one or more halogens, $(C_1-C_3)$alkoxy, $(C_1-C_3)$alkyl, or hydroxyl;

R3 is selected from hydrogen and a group —$(CH_2)_mCH_2$—COOH;

R4 is hydrogen or fluoro, and is preferably hydrogen;

R5 is selected from hydrogen, halogen, methyl or methoxy, and preferably represents fluoro or hydrogen, and particularly hydrogen;

n and m are independently 0, 1 or 2.

3. The method according to claim 1, wherein in formula I

R1 is selected from the group consisting of methyl, methoxy, hydroxy, $CF_3$, chloro, fluoro, bromo, iodo, thienyl, furanyl, pyridyl, and phenyl which is optionally substituted with halogen, methyl or methoxy;

R2 is selected from the group consisting of hydrogen, methyl, methoxy, hydroxyl, $CF_3$, chloro, fluoro, bromo, iodo and phenyl;

R3 is hydrogen, carboxymethyl, or carboxyethyl;

R4 and R5 are both hydrogen; and n is 1.

4. The method according to claim 1 wherein the GPR 17 agonist of formula I is selected from the group consisting of 3-(2-carboxyethyl)-4,6-dichloro-1H-indole-2-carboxylic acid, 3-(2-carboxyethyl)-4,6-dichloro-(1-carboxyethyl)-indole-2-carboxylic acid, 3-(2-carboxyethyl)-4,6-dimethyl-1H-indole-2-carboxylic acid, 3-(2-carboxyethyl)-6-chloro-1H-indole-2-carboxylic acid, 3-(2-carboxyethyl)-4,6-difluoro-1H-indole-2-carboxylic acid, 3-(2-carboxyethyl)-4,6-dibromo-1H-indole-2-carboxylic acid, 3-(2-carboxyethyl)-6-bromo-1H-indole-2-carboxylic acid, 3-(2-carboxyethyl)-6-iodo-1H-indole-2-carboxylic acid, 3-(2-carboxyethyl)-4,6-diiodo-1H-indole-2-carboxylic acid, 3-(2-carboxyethyl)-4,6-dichloro-1H-indole-2-carboxylic acid, 3-(2-carboxyethyl)-4,6-diphenyl-1H-indole-2-carboxylic acid, 3-(2-carboxyethyl)-6-phenyl-1H-indole-2-carboxylic acid, 3-(2-carboxyethyl)-6,7-dichloro-1H-indole-2-carboxylic acid, 3-(2-carboxyethyl)-6-chloro-7-fluoro-1H-indole-2-carboxylic acid, 3-(2-carboxyethyl)-6-bromo-2-carboxy-7-fluoro)-1H-indole-2-carboxylic acid, 3-(2-carboxyethyl)-4,6-dimethoxy-1H-indole-2-carboxylic acid, 3-(2-carboxyethyl)-6-phenoxy-1H-indole-2-carboxylic acid, 3-(2-carboxyethyl)-6-benzyl-2-carboxy-1H-indole-2-carboxylic acid, 3-(2-carboxyethyl)-4,6-dihydroxy-1H-indole-2-carboxylic acid, 3-(2-carboxyethyl)-6-(4-fluorophenyl)-1H-indol-2-carboxylic acid, 3-(2-carboxyethyl)-6-furanyl-1H-indole-2-carboxylic acid, 3-(2-carboxyethyl)-6-thienyl-1H-indole-2-carboxylic acid, 3-(2-carboxyethyl)-7-fluoro-6-phenyl-1H-indole-2-carboxylic acid, 3-(2-carboxyethyl)-6-(4-fluorophenyl)-7-fluoro-1H-indol-2-carboxylic acid, 3-(2-carboxyethyl)-6-furanyl-7-fluoro-1H-indole-2-carboxylic acid, 3-(2-carboxyethyl)-6-thienyl-7-fluoro-1H-indole-2-carboxylic acid or a salt thereof.

5. The method according to claim 1, wherein the biological activity of GPR17 is determined by measuring one or more of the following parameters: $^{35}SGTP_\gamma S$ binding, the inhibition of cAMP formation, the release of calcium from intracellular calcium stores, the increase in inositolphosphates (IP), and/or the recruitment of cytoplasmic β-arrestin proteins.

6. The method according to claim 1, wherein the activity of GPR17 is measured in a transfected cell line or membrane fragments thereof, which is preferably selected from transfected CHO cells, astrocytoma cells, COS7 cells or HEK293 cells and/or in naturally expressing tissue or cells and membrane fragments thereof.

7. The method, according to claim 1, comprising the additional steps of (d) selecting one or more analogs of the GPR 17 modulating compound(s) identified in steps (a) to (c), (e) subjecting the one or more GPR 17 modulating compound analogs of step (d) to the method and/or assay of claim 1 thereby determining the GPR 17 modulating properties of said GPR 17 modulating compound analogs, and (f) optionally repeating steps (d) to (e) one or more times by producing further chemical analogs of the GPR 17 modulating compound(s) thereby identifying one or more GPR17 modulating compound(s) with improved GPR17 modulating properties.

* * * * *